US012201470B2

(12) United States Patent
Mahrooghy et al.

(10) Patent No.: US 12,201,470 B2
(45) Date of Patent: Jan. 21, 2025

(54) SYSTEM AND METHOD FOR FEATURE EXTRACTION AND CLASSIFICATION ON ULTRASOUND TOMOGRAPHY IMAGES

(71) Applicant: Delphinus Medical Technologies, Inc., Novi, CA (US)

(72) Inventors: Majid Mahrooghy, Novi, MI (US); Gursharan Singh Sandhu, Novi, MI (US); Peter Littrup, Novi, MI (US)

(73) Assignee: Delphinus Medical Technologies, Inc., Novi, MI (US)

( * ) Notice: Subject to any disclaimer, the term of this patent is extended or adjusted under 35 U.S.C. 154(b) by 864 days.

(21) Appl. No.: 17/076,384

(22) Filed: Oct. 21, 2020

(65) Prior Publication Data

US 2021/0035296 A1  Feb. 4, 2021

Related U.S. Application Data

(63) Continuation of application No. PCT/US2019/029592, filed on Apr. 29, 2019.
(Continued)

(51) Int. Cl.
*A61B 8/08* (2006.01)
*G06T 7/00* (2017.01)
(Continued)

(52) U.S. Cl.
CPC ............. *A61B 8/08* (2013.01); *A61B 8/0825* (2013.01); *A61B 8/085* (2013.01); *A61B 8/5223* (2013.01);
(Continued)

(58) Field of Classification Search
CPC ......... A61B 8/08; A61B 8/0825; A61B 8/085; A61B 8/5223; A61B 8/4281; A61B 8/469;
(Continued)

(56) References Cited

U.S. PATENT DOCUMENTS 8,663,113 B2   3/2014  Schmidt et al.
9,113,835 B2   8/2015  Li
(Continued)

FOREIGN PATENT DOCUMENTS

CN   105377145 A       3/2016
CN   106778829    *    4/2019    ............. G06F 18/23
(Continued)

OTHER PUBLICATIONS

EP19792932.6 Extended Search Report dated Nov. 26, 2021.
(Continued)

*Primary Examiner* — Jerome Grant, II
(74) *Attorney, Agent, or Firm* — WILSON SONSINI GOODRICH & ROSATI

(57) ABSTRACT

Disclosed herein systems, processors, or computer-readable media configured with instructions to: receive transmission and/or reflection images of a tissue of a subject, wherein the images are generated from acoustic signals derived from acoustic waveforms transmitted through the tissue; provide a set of prognostic parameters associated with a user selected region of interest; wherein the set of prognostic parameters comprises sound propagation metrics characterizing sound propagation within a tissue; wherein the set of prognostic parameters corresponds to inputs into a tissue classifier model; wherein the set of prognostic parameters comprises a plurality of subsets of related feature groupings; and determine a type of tissue of the subject based on said plurality of subsets of related feature groupings using the classifier model, wherein the type of tissue is a cancerous tumor, a fibroadenoma, a cyst, a nonspecific benign mass, and an unidentifiable mass.

19 Claims, 38 Drawing Sheets

Related U.S. Application Data

(60) Provisional application No. 62/838,174, filed on Apr. 24, 2019, provisional application No. 62/664,038, filed on Apr. 27, 2018.

(51) Int. Cl.
  *G06V 10/25* (2022.01)
  *G06V 10/26* (2022.01)
  *G06V 10/44* (2022.01)
  *G06V 10/764* (2022.01)
  *G06V 10/77* (2022.01)
  *G06V 10/82* (2022.01)

(52) U.S. Cl.
  CPC ............ *G06T 7/0012* (2013.01); *G06V 10/25* (2022.01); *G06V 10/26* (2022.01); *G06V 10/44* (2022.01); *G06V 10/764* (2022.01); *G06V 10/7715* (2022.01); *G06V 10/82* (2022.01); *G06T 2207/10132* (2013.01); *G06T 2207/20081* (2013.01); *G06T 2207/30096* (2013.01)

(58) Field of Classification Search
  CPC ......... A61B 8/483; A61B 8/13; G06T 7/0012; G06T 2207/10132; G06T 2207/20081; G06T 2207/30096; G06T 7/10; G06T 15/08; G06T 2207/20084; G06T 2207/30068; G06V 10/25; G06V 10/26; G06V 10/44; G06V 10/764; G06V 10/7715; G06V 10/82; G06V 2201/03; G06F 18/259; G06F 18/2413; G06F 18/24323; G06F 18/2135; G16H 30/40; G16H 50/20
  USPC ........................................................ 382/128
  See application file for complete search history.

(56) References Cited

U.S. PATENT DOCUMENTS

| | | | |
|---|---|---|---|
| 9,763,641 | B2 | 9/2017 | West et al. |
| 10,076,304 | B2 | 9/2018 | Tesic et al. |
| 10,123,770 | B2 | 11/2018 | Szpak et al. |
| 10,143,443 | B2 | 12/2018 | Duric et al. |
| 10,285,667 | B2 | 5/2019 | Duric et al. |
| 10,368,831 | B2 | 8/2019 | Duric et al. |
| 10,743,837 | B2 | 8/2020 | Sandhu et al. |
| 11,350,905 | B2 | 6/2022 | Duric et al. |
| 2003/0007598 | A1* | 1/2003 | Wang .............. A61B 6/463 378/37 |
| 2009/0016586 | A1 | 1/2009 | Gardner et al. |
| 2011/0201932 | A1 | 8/2011 | Duric et al. |
| 2012/0243757 | A1 | 9/2012 | Funka-Lea et al. |
| 2013/0204136 | A1 | 8/2013 | Duric et al. |
| 2013/0204137 | A1 | 8/2013 | Roy et al. |
| 2013/0251222 | A1 | 9/2013 | Huang |
| 2013/0315465 | A1 | 11/2013 | Cosatto et al. |
| 2014/0018682 | A1 | 1/2014 | Baba et al. |
| 2015/0025388 | A1 | 1/2015 | Huang et al. |
| 2015/0297173 | A1 | 10/2015 | Klock et al. |
| 2015/0297174 | A1* | 10/2015 | Duric .............. A61B 8/461 600/442 |
| 2016/0038123 | A1 | 2/2016 | Duric et al. |
| 2016/0317121 | A1 | 11/2016 | Frenz et al. |
| 2017/0337687 | A1 | 11/2017 | Wang et al. |
| 2020/0022672 | A1 | 1/2020 | Duric et al. |
| 2021/0390701 | A1* | 12/2021 | Fan ............... G06T 7/0012 |

FOREIGN PATENT DOCUMENTS

| | | | | |
|---|---|---|---|---|
| EP | 2533684 | A1 | 12/2012 | |
| JP | 2003116855 | A | 4/2003 | |
| JP | 2008541889 | A | 11/2008 | |
| JP | 2012239546 | A | 12/2012 | |
| JP | 2013519455 | * | 5/2013 | ........... A61B 8/0825 |
| JP | 2013519455 | A | 5/2013 | |
| JP | 2013244218 | A | 12/2013 | |
| JP | 2015154918 | A | 8/2015 | |
| JP | 6468179 | * | 2/2019 | |
| WO | WO-2017040866 | A1 | 3/2017 | |
| WO | WO-2017139389 | A1 | 8/2017 | |
| WO | WO2017079843 | * | 5/2018 | ............... A61B 8/00 |
| WO | WO-2018/102776 | | 6/2018 | |
| WO | WO-2019210292 | A1 | 10/2019 | |

OTHER PUBLICATIONS

U.S. Appl. No. 16/443,993 Notice of Allowance dated Feb. 2, 2022.
U.S. Appl. No. 16/443,993 Office Action dated Jul. 8, 2021.
Cosman, Pamela. Gray-Level Co-occurrence Matrices (GLCMs). Available at http://www.code.ucsd.edu/pcosman/glcm.pdf; Accessed on Jan. 19, 2021.
Duric et al. Breast imaging with ultrasound tomography: clinical results at the karmanos cancer institute; Biomedical Engineering and Informatics, 2008; IEEE International Conference, pp. 713-717 (2008).
Duric et al., In-vivo imaging of breast cancer with ultrasound tomography: probing the tumor environment, Medical Imaging 2011: Ultrasonic Imaging, Tomography, and Therapy, vol. 7968, No. 1, pp. 1-7 (2011).
EP17876240.7 European Search Report dated Jun. 4, 2020.
Honda, et al., Computer-Aided Diagnosis Scheme for Distinguishing Between Benign and Malignant Masses in Breast DCE-MRI. J Digit Imaging. Jun. 2016; 29(3): 388-393.
PCT/US2017/064350 International Search Report and Written Opinion dated Mar. 22, 2018.
PCT/US2019/029592 International Search Report & Written Opinion dated Sep. 11, 2019.
U.S. Appl. No. 15/829,748 Office Action dated Oct. 1, 2018.
U.S. Appl. No. 15/829,748 Notice of Allowance dated Mar. 20, 2019.

* cited by examiner (a) Sound speed (b) Reflection (c) Wafer (d) Segmentation by MMF (e) Manual segmentation by a radiologist (f) Manual (gray) and Auto (white) segmentaion (c) Wafer (f) Manual (gray) and Auto (white) segmentaion (b) Reflection (e) Manual segmentation by a radiologist (a) Sound speed (d) Segmentation by GMF (a) Sound speed (b) Reflection (c) Wafer (d) Segmented by GMM (e) Manual segmentation by a radiologist (f) Manual (gray) and Auto (white) segmentation 1. Find thin sub-λ feature 2. Generate cross cut 3. Measure full width - half max

SYSTEM AND METHOD FOR FEATURE EXTRACTION AND CLASSIFICATION ON ULTRASOUND TOMOGRAPHY IMAGES

CROSS-REFERENCE

This is a continuation application, which claims priority to International Patent Application No.: PCT/US2019/029592, filed Apr. 29, 2019, which claims benefit of U.S. Provisional Ser. No. 62/664,038, filed on Apr. 27, 2018, and U.S. Provisional Ser. No. 62/838,174, filed Apr. 24, 2019, both of which are incorporated herein by this reference in their entireties.

BACKGROUND

Breast cancer may be one of the leading causes of cancer mortality among women. Early detection of breast disease can lead to a reduction in the mortality rate. However, problems exist with the sensitivity and specificity of current standards for breast cancer screening. These problems are substantial within the subset of young women with dense breasts who are at an increased risk for cancer development.

The prior approaches to ultrasound imaging to identify tissue types can be less than ideal and may not accurately identify tissue types in at least some instances. For example, the reliance on a skilled technician or operator can be somewhat time consuming. Also, the prior use of imaging modalities may convey less information than would be ideal. In a clinical setting, a radiologist or other medical professional may review the images (e.g., ultrasound tomography images) of a scanned patient and make a diagnosis based on what is seen. In particular, radiologists rely on their experience and training to make decisions on the presence of any focal imaging abnormalities. However, these decisions may not always be correct. Radiologists may review the same image differently, and such differences may be further exaggerated when the radiologists have different levels of training or are trained differently. This reliance on the knowledge and skill of an operator rather than objective data can provide less than ideal results.

Although machine learning has been proposed to determine tissue types, the prior uses of machine learning can provide less than ideal results in at least some instances. For example, the input data may be less than ideal, and may not be fully or appropriately utilized. Also, some of the prior approaches with machine learning can rely on less accurate input parameters, thereby producing less than ideal accuracy, sensitivity and specificity in at least some instances. Further the combinations of input data can be less than ideally utilized, thereby decreasing the accuracy, sensitivity and specificity in at least some instances.

In light of the above, there is a need for improved methods and apparatus to evaluate the tissue of ultrasound images with improved accuracy.

SUMMARY

The methods and apparatus disclosed herein provide improved identification of lesions in a volume of tissue. The methods and apparatus can use feature extraction and characterization aided by machine learning using a plurality of related features as input parameters, such as subsets of related features. The use of subsets of related feature grouping can provide improved accuracy, sensitivity and specificity. The plurality of subsets of related features may comprise related sound speed features, related sound attenuation features, and related reflection features. The related sound speed features may comprise a mean, a standard deviation, a skewness and kurtosis. The related attenuation features, generated through the imaginary component of sound speed or through bulk measurements, may comprise a mean, a standard deviation, a skewness and kurtosis. The related reflection features may comprise a mean, standard of deviation, a skewness and a kurtosis of the reflection features. The related derived imaging modalities such as waveform enhanced sound speed or stiffness imaging may comprise a mean, standard of deviation, a skewness and a kurtosis of the reflection features. Each of the subsets corresponding to sound speed features, attenuation features, reflection features and derived features can be input into the classifier in order to obtain improved accuracy of the determination of the tissue type. These features can be used with image data segmentation, feature extraction, feature selection, and tissue classification based on machine learning algorithm(s). In some embodiments, the methods and apparatus are configured for the selection of feature subsets (e.g., a single feature class or features from multiple classes) in order to improve the classification accuracy.

The methods and apparatus disclosed herein can be configured to perform tissue characterization of ultrasound images (e.g., ultrasound tomography) using machine learning techniques with a series of steps in response to the sound speed features, the reflection features, the attenuation features, and derived imaging modality features. In some embodiments, a set of images comprising examples of different types of tissues and masses can be generated. A trained radiologist can then locate and segment the tissue of interest by generating a region-of-interest (ROI) mask (e.g., binary). Features can then be extracted from the ROI with the related subsets. Using feature selection technique(s), the most relevant features are then fed to train a machine learning classifier model. The trained classifier can then be fed features from an unknown tissue sample to determine a label or classification for the unknown tissue sample in response to the related feature subsets.

In an aspect, a computer implemented method for characterizing a lesion in a volume of tissue is provided. The method may comprise: receiving a plurality of acoustic renderings, the acoustic renderings comprising a representation of sound propagation through the volume of tissue, wherein the plurality of acoustic renderings comprises at least a transmission rendering and a reflection rendering; determining a set of prognostic parameters, wherein the set of prognostic parameters comprises one or a plurality of sound propagation metrics that are derived from the plurality of acoustic renderings; assigning each element of the set of prognostic parameters a predictive value, wherein the predictive value is based on a plurality of classified acoustic renderings; forming a classifier model from a subset of the set of prognostic parameters, the subset determined based on the predictive value of each of at least a subset of the set of the prognostic parameters; and calculating a score using the classifier model, the score relating to a probability that the lesion is of a classification.

In some embodiments, the lesion comprises a cancer, a fibroadenoma, a cyst, a nonspecific benign mass, or an unidentifiable mass. In some embodiments, the plurality of acoustic renderings comprises combined acoustic renderings. In some embodiments, the combined acoustic renderings comprise a plurality of reflection renderings. In some embodiments, the combined renderings comprise a plurality of transmission renderings. In some embodiments, the combined renderings comprise at least one reflection rendering and at least one transmission rendering. In some embodiments, a transmission rendering comprises a sound speed rendering or an attenuation rendering. In some embodiments, the prognostic parameters comprise sound speed metrics relating to a region of interest. In some embodiments, the region of interest is a user selected region of interest. In some embodiments, the region of interest comprises at least a portion of the lesion. In some embodiments, the region of interest comprises a two-dimensional region of interest. In some embodiments, the region of interest is at least partially determined via edge detection. In some embodiments, the region of interest is at least partially selected using the set of prognostic parameters. In some embodiments, the two-dimensional region of interest is used to generate a three-dimensional region of interest. In some embodiments, a mask is generated based on said region of interest. In some embodiments, the set of prognostic parameters is based on said region of interest. In some embodiments, the set of prognostic parameters comprises a user-assigned classification of the region of interest. In some embodiments, the user-assigned classification is a mass boundary score. In some embodiments, the set of prognostic parameters comprises at least one morphological metric of the lesion. In some embodiments, the morphological metric comprises at least one of a roundness, an irregularity of a shape, an irregularity of a margin, and a smoothness of a margin. In some embodiments, the set of prognostic parameters comprises fuzziness. In some embodiments, said fuzziness is of a boundary of the lesion. In some embodiments, the set of prognostic parameters comprises crispiness. In some embodiments, said crispiness is of a margin of the lesion. In some embodiments, the set of prognostic parameters comprises at least one texture metric of the region of interest. In some embodiments, the texture metric comprises at least one of an edgeness, a grey level co-occurrence matrix, and a Law's texture map. In some embodiments, the one or a plurality of sound propagation metrics characterizes sound propagation interior to a region of interest. In some embodiments, the one or a plurality of sound propagation metrics characterizes sound propagation exterior to a region of interest. In some embodiments, the first sound propagation metric characterizes sound propagation interior to a region of interest and a second sound propagation metric characterizes sound propagation exterior to a region of interest. In some embodiments, the one or a plurality of sound propagation metrics comprises at least one of a mean, a standard deviation, a skewness, and a kurtosis. In some embodiments, the one or a plurality of sound propagation metrics characterizes at least one of sound speed, sound attenuation, and sound reflection. In some embodiments, the one or a plurality of sound propagation metrics comprises at least a sound speed metric and a reflection metric. In some embodiments, the one or a plurality of sound propagation metrics comprises at least a sound speed metric, a reflection metric, and an attenuation metric. In some embodiments, the one or a plurality of sound propagation metrics comprises at least a sound speed metric, a reflection metric, an attenuation metric, and a user defined score. In some embodiments, the one or a plurality of sound propagation metrics comprises at least a sound speed metric, a reflection metric, an attenuation metric, and morphological metric. In some embodiments, the one or a plurality of sound propagation metrics comprises at least a sound speed metric, a reflection metric, an attenuation metric, a morphological metric, and a user defined score. In some embodiments, the set of prognostic parameters is trimmed. In some embodiments, one of the plurality subsets comprises the one or a plurality of sound propagation metrics characterizing sound speed. In some embodiments, one of the plurality subsets comprises the one or a plurality of sound propagation metrics characterizing sound attenuation. In some embodiments, one of the plurality subsets comprises the one or a plurality of sound propagation metrics characterizing sound reflection. In some embodiments, the classifier model determines a type of tissue with a sensitivity at least 85% and a specificity of at least 84%. In some embodiments, the classifier model determines a threshold value of one or more prognostic parameters sufficient to classify a tissue. In some embodiments, the classifier model determines a relative statistical accuracy of one or more prognostic parameters. In some embodiments, the classifier model determines a threshold value of a said subset prognostic parameters sufficient to classify a tissue. In some embodiments, the classifier determines a likelihood that the lesion is a malignant lesion. In some embodiments, the likelihood that the lesion is a malignant lesion is expressed as a percentage. In some embodiments, the classifier model is generated using a machine learning technique. In some embodiments, the machine learning technique comprises a support vector machine.

In another aspect, a processor comprising a tangible medium is provided. The tangible medium may be configured with instructions to: receive a plurality of acoustic renderings, the acoustic renderings comprising a representation of sound propagation through the volume of tissue, wherein the plurality of acoustic renderings comprises at least a transmission rendering and a reflection rendering; determine a set of prognostic parameters, wherein the set of prognostic parameters comprises one or a plurality of sound propagation metrics that are derived from the plurality of acoustic renderings; assign each element of the set of prognostic parameters a predictive value, wherein the predictive value is based on a plurality of classified acoustic renderings; form a classifier model from a subset of the set of prognostic parameters, the subset determined based on the predictive value of each of at least a subset of the set of the prognostic parameters; and calculate a score using the classifier model, the score relating to a probability that the lesion is of a classification.

In some embodiments, the lesion comprises a cancer, a fibroadenoma, a cyst, a nonspecific benign mass, or an unidentifiable mass. In some embodiments, the plurality of acoustic renderings comprises combined acoustic renderings. In some embodiments, the combined acoustic renderings comprise a plurality of reflection renderings. In some embodiments, the combined renderings comprise a plurality of transmission renderings. In some embodiments, the combined renderings comprise at least one reflection rendering and at least one transmission rendering. In some embodiments, a transmission rendering comprises a sound speed rendering or an attenuation rendering. In some embodiments, the prognostic parameters comprise sound speed metrics relating to a region of interest. In some embodiments, the region of interest is a user selected region of interest. In some embodiments, the region of interest comprises at least a portion of the lesion. In some embodiments, the region of interest comprises a two-dimensional region of interest. In some embodiments, the region of interest is at least partially determined via edge detection. In some embodiments, the region of interest is at least partially selected using the set of prognostic parameters. In some embodiments, the two-dimensional region of interest is used to generate a three-dimensional region of interest. In some embodiments, a mask is generated based on said region of interest. In some embodiments, the set of prognostic parameters is based on said region of interest. In some embodiments, the set of prognostic parameters comprises a user-assigned classification of the region of interest. In some embodiments, the user-assigned classification is a mass boundary score. In some embodiments, the set of prognostic parameters comprises at least one morphological metric of the lesion. In some embodiments, the morphological metric comprises at least one of a roundness, an irregularity of a shape, an irregularity of a margin, and a smoothness of a margin. In some embodiments, the set of prognostic parameters comprises fuzziness. In some embodiments, said fuzziness is of a boundary of the lesion. In some embodiments, the set of prognostic parameters comprises crispiness. In some embodiments, said crispiness is of a margin of the lesion. In some embodiments, the set of prognostic parameters comprises at least one texture metric of the region of interest. In some embodiments, the texture metric comprises at least one of an edgeness, a grey level co-occurrence matrix, and a Law's texture map. In some embodiments, the one or a plurality of sound propagation metrics characterizes sound propagation interior to a region of interest. In some embodiments, the one or a plurality of sound propagation metrics characterizes sound propagation exterior to a region of interest. In some embodiments, the first sound propagation metric characterizes sound propagation interior to a region of interest and a second sound propagation metric characterizes sound propagation exterior to a region of interest. In some embodiments, the one or a plurality of sound propagation metrics comprises at least one of a mean, a standard deviation, a skewness, and a kurtosis. In some embodiments, the one or a plurality of sound propagation metrics characterizes at least one of sound speed, sound attenuation, and sound reflection. In some embodiments, the one or a plurality of sound propagation metrics comprises at least a sound speed metric and a reflection metric. In some embodiments, the one or a plurality of sound propagation metrics comprises at least a sound speed metric, a reflection metric, and an attenuation metric. In some embodiments, the one or a plurality of sound propagation metrics comprises at least a sound speed metric, a reflection metric, an attenuation metric, and a user defined score. In some embodiments, the one or a plurality of sound propagation metrics comprises at least a sound speed metric, a reflection metric, an attenuation metric, and morphological metric. In some embodiments, the one or a plurality of sound propagation metrics comprises at least a sound speed metric, a reflection metric, an attenuation metric, a morphological metric, and a user defined score. In some embodiments, the set of prognostic parameters is trimmed. In some embodiments, one of the plurality subsets comprises the one or a plurality of sound propagation metrics characterizing sound speed. In some embodiments, one of the plurality subsets comprises the one or a plurality of sound propagation metrics characterizing sound attenuation. In some embodiments, one of the plurality subsets comprises the one or a plurality of sound propagation metrics characterizing sound reflection. In some embodiments, the classifier model determines a type of tissue with a sensitivity at least 85% and a specificity of at least 84%. In some embodiments, the classifier model determines a threshold value of one or more prognostic parameters sufficient to classify a tissue. In some embodiments, the classifier model determines a relative statistical accuracy of one or more prognostic parameters. In some embodiments, the classifier model determines a threshold value of a said subset prognostic parameters sufficient to classify a tissue. In some embodiments, the classifier determines a likelihood that the lesion is a malignant lesion. In some embodiments, the likelihood that the lesion is a malignant lesion is expressed as a percentage. In some embodiments, the classifier model is generated using a machine learning technique. In some embodiments, the machine learning technique comprises a support vector machine.

In another aspect, a computer implemented method for classifying a lesion in a volume of tissue is provided. The method may comprise: receiving a plurality of acoustic renderings, the acoustic renderings comprising a representation of sound propagation through the volume of tissue, wherein the plurality of acoustic renderings comprises at least a transmission rendering and a reflection rendering; indicating a region of interest within the volume of tissue, wherein the region is proximate the lesion within the volume of tissue; segmenting a portion of at least one of the plurality of acoustic renderings near the region of interest; providing an indication that the portion is in an interior or an exterior of the lesion; generating a mask, wherein the mask comprises a prediction of a shape of the lesion; and determining a set of prognostic parameters, wherein the set of prognostic parameters comprises one or a plurality of sound propagation metrics that are derived from the plurality of acoustic renderings.

In some embodiments, the segmenting comprises a Markov Random Field, a Gaussian Mixture Model, or an Adaptive Fuzzy C-Mean method. In some embodiments, the segmenting comprises at least two of a Markov Random Field, a Gaussian Mixture Model, or an Adaptive Fuzzy C-Mean method. In some embodiments, the method further comprises, determining that the portion is in an interior or an exterior of a lesion by at least two of the Markov Random Field, the Gaussian Mixture Model, or the Adaptive Fuzzy C-Mean method. In some embodiments, the method further comprises forming a classifier model from the set of prognostic parameters. In some embodiments, the method further comprises classifying a lesion within the volume of tissue as one of a cancer, a fibroadenoma, a cyst, a nonspecific benign mass, or an unidentifiable mass. In some embodiments, the method further comprises calculating a score using the classifier model, the score relating to a probability that the lesion is one of a cancer, a fibroadenoma, a cyst, a nonspecific benign mass, or an unidentifiable mass.

In some embodiments, the lesion comprises a cancer, a fibroadenoma, a cyst, a nonspecific benign mass, or an unidentifiable mass. In some embodiments, the plurality of acoustic renderings comprises combined acoustic renderings. In some embodiments, the combined acoustic renderings comprise a plurality of reflection renderings. In some embodiments, the combined renderings comprise a plurality of transmission renderings. In some embodiments, the combined renderings comprise at least one reflection rendering and at least one transmission rendering. In some embodiments, a transmission rendering comprises a sound speed rendering or an attenuation rendering. In some embodiments, the prognostic parameters comprise sound speed metrics relating to a region of interest. In some embodiments, the region of interest is a user selected region of interest. In some embodiments, the region of interest comprises at least a portion of the lesion. In some embodiments, the region of interest comprises a two-dimensional region of interest. In some embodiments, the region of interest is at least partially determined via edge detection. In some embodiments, the region of interest is at least partially selected using the set of prognostic parameters. In some embodiments, the two-dimensional region of interest is used to generate a three-dimensional region of interest. In some embodiments, a mask is generated based on said region of interest. In some embodiments, the set of prognostic parameters is based on said region of interest. In some embodiments, the set of prognostic parameters comprises a user-assigned classification of the region of interest. In some embodiments, the user-assigned classification is a mass boundary score. In some embodiments, the set of prognostic parameters comprises at least one morphological metric of the lesion. In some embodiments, the morphological metric comprises at least one of a roundness, an irregularity of a shape, an irregularity of a margin, and a smoothness of a margin. In some embodiments, the set of prognostic parameters comprises fuzziness. In some embodiments, said fuzziness is of a boundary of the lesion. In some embodiments, the set of prognostic parameters comprises crispiness. In some embodiments, said crispiness is of a margin of the lesion. In some embodiments, the set of prognostic parameters comprises at least one texture metric of the region of interest. In some embodiments, the texture metric comprises at least one of an edgeness, a grey level co-occurrence matrix, and a Law's texture map. In some embodiments, the one or a plurality of sound propagation metrics characterizes sound propagation interior to a region of interest. In some embodiments, the one or a plurality of sound propagation metrics characterizes sound propagation exterior to a region of interest. In some embodiments, the first sound propagation metric characterizes sound propagation interior to a region of interest and a second sound propagation metric characterizes sound propagation exterior to a region of interest. In some embodiments, the one or a plurality of sound propagation metrics comprises at least one of a mean, a standard deviation, a skewness, and a kurtosis. In some embodiments, the one or a plurality of sound propagation metrics characterizes at least one of sound speed, sound attenuation, and sound reflection. In some embodiments, the one or a plurality of sound propagation metrics comprises at least a sound speed metric and a reflection metric. In some embodiments, the one or a plurality of sound propagation metrics comprises at least a sound speed metric, a reflection metric, and an attenuation metric. In some embodiments, the one or a plurality of sound propagation metrics comprises at least a sound speed metric, a reflection metric, an attenuation metric, and a user defined score. In some embodiments, the one or a plurality of sound propagation metrics comprises at least a sound speed metric, a reflection metric, an attenuation metric, and morphological metric. In some embodiments, the one or a plurality of sound propagation metrics comprises at least a sound speed metric, a reflection metric, an attenuation metric, a morphological metric, and a user defined score. In some embodiments, the set of prognostic parameters is trimmed. In some embodiments, one of the plurality subsets comprises the one or a plurality of sound propagation metrics characterizing sound speed. In some embodiments, one of the plurality subsets comprises the one or a plurality of sound propagation metrics characterizing sound attenuation. In some embodiments, one of the plurality subsets comprises the one or a plurality of sound propagation metrics characterizing sound reflection. In some embodiments, the classifier model determines a type of tissue with a sensitivity at least 85% and a specificity of at least 84%. In some embodiments, the classifier model determines a threshold value of one or more prognostic parameters sufficient to classify a tissue. In some embodiments, the classifier model determines a relative statistical accuracy of one or more prognostic parameters. In some embodiments, the classifier model determines a threshold value of a said subset prognostic parameters sufficient to classify a tissue. In some embodiments, the classifier determines a likelihood that the lesion is a malignant lesion. In some embodiments, the likelihood that the lesion is a malignant lesion is expressed as a percentage. In some embodiments, the classifier model is generated using a machine learning technique. In some embodiments, the machine learning technique comprises a support vector machine.

In another aspect, the processor comprising a tangible medium configured with instructions to perform any embodiment or aspect of method of classifying a lesion within a volume of tissue disclosed herein is provided.

In another aspect, a processor comprising a tangible medium configured with instructions is provided. The tangible medium may be configured with instructions to: receive a plurality of images the tissue of a subject, the plurality of images selected from the group consisting of a transmission image and a reflection image, wherein the plurality of images is generated from a plurality of acoustic signals derived from acoustic waveforms transmitted through the volume of tissue; provide a set of prognostic parameters associated with a user selected region of interest; wherein the set of prognostic parameters comprises one or a plurality of sound propagation metrics characterizing sound propagation within a tissue; wherein the set of prognostic parameters corresponds to inputs into a tissue classifier model; wherein the set of prognostic parameters comprises a plurality of subsets of related feature groupings; and determine a type of tissue of the subject based on said plurality of subsets of related feature groupings using the classifier model, wherein the type of tissue is selected from the group consisting of a cancerous tumor, a fibroadenoma, a cyst, a nonspecific benign mass, and an unidentifiable mass.

In some embodiments, a transmission image comprises a speed image or an attenuation image. In some embodiments, a plurality of images comprises combined images. In some embodiments, a combined image comprises a plurality of reflection images. In some embodiments, a combined image comprises a plurality of transmission images. In some embodiments, a combined image comprises at least one reflection image and at least one transmission image.

In some embodiments, a user selected region of interest comprises a two-dimensional region of interest. In some embodiments, selection of a user-selected two-dimensional region of interest is aided by the processor. In some embodiments, the processor aids selection of a region of interest by edge detection. In some embodiments, the processor aids selection of a region of interest using the set of prognostic parameters. In some embodiments, the user selected region of interest is used to generate a three-dimensional region of interest. In some embodiments, a mask is generated based on said three-dimensional region of interest. In some embodiments, a set of prognostic parameters is generated based on said three-dimensional region of interest. In some embodiments, a mask is generated based on said two-dimensional region of interest. In some embodiments, a set of prognostic parameters is based on said two-dimensional region of interest.

In some embodiments, a set of prognostic parameters comprises a user-assigned classification of a region of interest. In some embodiments, a user-assigned classification comprises a mass boundary score. In some embodiments, a set of prognostic parameters comprises at least one morphological metric of the region of interest. In some embodiments, a morphological metric comprises at least one of a roundness, an irregularity of a shape, an irregularity of a margin, and a smoothness of a margin. In some embodiments, a set of prognostic parameters comprises at least one texture metric of the region of interest. In some embodiments, a texture metric comprises at least one of an edgeness, a grey level co-occurrence matrix, and a Law's texture map.

In some embodiments, one or a plurality of sound propagation metrics characterizes sound propagation interior to a region of interest. In some embodiments, one or a plurality of sound propagation metrics characterizes sound propagation exterior to a region of interest. In some embodiments, a first sound propagation metric characterizes sound propagation interior to a region of interest and a second sound propagation metric characterizes sound propagation exterior to a region of interest. In some embodiments, one or a plurality of sound propagation metrics comprises at least one of a mean, a standard deviation, a skewness, and a kurtosis.

In some embodiments, one or a plurality of sound propagation metrics characterizes at least one of sound speed, sound attenuation, and sound reflection. In some embodiments, one or a plurality of sound propagation metrics comprises at least a sound speed metric and a reflection metric. In some embodiments, one or a plurality of sound propagation metrics comprises at least a sound speed metric, a reflection metric, and an attenuation metric. In some embodiments, one or a plurality of sound propagation metrics comprises at least a sound speed metric, a reflection metric, an attenuation metric, and a user defined score. In some embodiments, one or a plurality of sound propagation metrics comprises at least a sound speed metric, a reflection metric, an attenuation metric, and morphological metric. In some embodiments, one or a plurality of sound propagation metrics comprises at least a sound speed metric, a reflection metric, an attenuation metric, a morphological metric, and a user defined score.

In some embodiments, a set of prognostic parameters is trimmed. In some embodiments, trimming the set of prognostic parameters is aided by the processor. In some embodiments, the processor trims the set of prognostic parameters based on a method selected from the group consisting of: principle component analysis, multilinear principle component analysis, and decision tree analysis. In some embodiments, one of the plurality subsets comprises the one or a plurality of sound propagation metrics characterizing sound speed. In some embodiments, one of the plurality subsets comprises the one or a plurality of sound propagation metrics characterizing sound attenuation. In some embodiments, one of the plurality subsets comprises the one or a plurality of sound propagation metrics characterizing sound reflection.

In some embodiments, a classifier model determines a type of tissue with a sensitivity of at least 85% and a specificity of at least 84%. In some embodiments, a classifier model determines a threshold value of one or more prognostic parameters sufficient to classify a tissue. In some embodiments, a classifier model determines a relative statistical accuracy of one or more prognostic parameters. In some embodiments, a relative statistical accuracy is a specificity or sensitivity of tissue classification.

In some embodiments, a classifier model builds a decision tree based on the accuracy of said one or more prognostic parameters. In some embodiments, a classifier model builds a decision tree based on the accuracy of said subset of prognostic parameters. In some embodiments, a classifier model determines a threshold value of a said subset prognostic parameters sufficient to classify a tissue using said decision tree. In some embodiments, a classifier model determines a threshold value of a said subset prognostic parameters sufficient to classify a tissue.

In some embodiments, a classifier model has been generated with a machine learning technique. In some embodiments, a machine learning technique comprises a support vector machine. In some embodiments, a support vector machine comprises LibSVM. In some embodiments, a machine learning technique comprises a decision tree. In some embodiments, a decision tree comprises J48, C4.5, or ID3. In some embodiments, a decision tree comprises ADABoost or DecisionStump. In some embodiments, a machine learning technique comprises a neural network. In some embodiments, a machine learning technique comprises k-nearest neighbors. In some embodiments, a machine learning technique comprises a Bayes classification.

In another aspect, a non-transitory computer-readable storage medium is provided. In some embodiments, the non-transitory computer-readable storage medium includes instructions stored thereon which instructions are executable by a processor. In some embodiments, the non-transitory computer-readable storage medium comprises instructions stored thereon which instructions are executable by the processor of any of the embodiments provided herein.

In another aspect, a computer system for determining a type of tissue of a subject is provided. In some embodiments, the computer system comprises a non-transitory computer-readable storage medium with instructions stored thereon which instructions are executable by a processor. In some embodiments, the computer system comprises a non-transitory computer-readable storage medium with instructions stored thereon which instructions are executable by the processor of any of the embodiments provided herein.

In another aspect, a system for generating images of a volume of tissue is provided. In some embodiments, the system comprises a transducer array comprising an array of ultrasound emitters and an array of ultrasound receivers, the transducer array configured around a volume of tissue, wherein the array of ultrasound transmitters is configured to emit acoustic waveforms toward the volume of tissue, wherein the array of ultrasound receivers is configured to receive the emitted acoustic waveforms and convert the received acoustic waveforms to a plurality of acoustic signals; a display visible to a user; and any embodiment of the processor disclosed herein.

In another aspect, a system for generating images of a volume of tissue is provided. In some embodiments, the system comprises a transducer array comprising an array of ultrasound emitters and an array of ultrasound receivers, the transducer array configured around a volume of tissue, wherein the array of ultrasound transmitters is configured to emit acoustic waveforms toward the volume of tissue, wherein the array of ultrasound receivers is configured to receive the emitted acoustic waveforms and convert the received acoustic waveforms to a plurality of acoustic signals; a display visible to a user; and any embodiment of the non-transitory computer-readable storage medium disclosed herein.

In another aspect, a method of determining a type of tissue with a classifier model, which method is implemented by a computer comprising one or more processors and computer readable storage media comprising instructions is provided. In some embodiments, the method comprises receiving a plurality of images the tissue of a subject, the plurality of images selected from the group consisting of a transmission image and a reflection image, wherein the plurality of images is generated from a plurality of acoustic signals derived from acoustic waveforms transmitted through the volume of tissue; providing a set of prognostic parameters associated with a user selected region of interest; wherein the set of prognostic parameters comprises one or a plurality of sound propagation metrics characterizing sound propagation within a tissue, wherein the set of prognostic parameters corresponds to inputs into a tissue classifier model, and wherein the set of prognostic parameters comprises a plurality of subsets of related feature groupings; and determining a type of tissue of the subject, wherein the type of tissue is selected from the group consisting of a cancerous tumor, a fibroadenoma, a cyst, a nonspecific benign mass, and an unidentifiable mass using said classifier model.

In another aspect, a non-transitory computer-readable storage medium with instructions stored thereon that, when executed by a processor, cause a processor to perform any embodiment of the method described herein is provided. In another aspect, a computer comprising the non-transitory computer-readable storage medium configured to perform any embodiment of the method described herein is provided.

In some embodiments, a transmission image comprises a speed image or an attenuation image. In some embodiments, a plurality of images comprises combined images. In some embodiments, a combined image comprises a plurality of reflection images. In some embodiments, a combined image comprises a plurality of transmission images. In some embodiments, a combined image comprises at least one reflection image and at least one transmission image.

In some embodiments, a user selected region of interest comprises a two-dimensional region of interest. In some embodiments, selection of a user-selected two-dimensional region of interest is aided by the processor. In some embodiments, the processor aids selection of a region of interest by edge detection. In some embodiments, the processor aids selection of a region of interest using the set of prognostic parameters. In some embodiments, the user selected region of interest is used to generate a three-dimensional region of interest. In some embodiments, a mask is generated based on said three-dimensional region of interest. In some embodiments, a set of prognostic parameters is generated based on said three-dimensional region of interest. In some embodiments, a mask is generated based on said two-dimensional region of interest. In some embodiments, a set of prognostic parameters is based on said two-dimensional region of interest.

In some embodiments, a set of prognostic parameters comprises a user-assigned classification of a region of interest. In some embodiments, a user-assigned classification comprises a mass boundary score. In some embodiments, a set of prognostic parameters comprises at least one morphological metric of the region of interest. In some embodiments, a morphological metric comprises at least one of a roundness, an irregularity of a shape, an irregularity of a margin, and a smoothness of a margin. In some embodiments, a set of prognostic parameters comprises at least one texture metric of the region of interest. In some embodiments, a texture metric comprises at least one of an edgeness, a grey level co-occurrence matrix, and a Law's texture map.

In some embodiments, one or a plurality of sound propagation metrics characterizes sound propagation interior to a region of interest. In some embodiments, one or a plurality of sound propagation metrics characterizes sound propagation exterior to a region of interest. In some embodiments, a first sound propagation metric characterizes sound propagation interior to a region of interest and a second sound propagation metric characterizes sound propagation exterior to a region of interest. In some embodiments, one or a plurality of sound propagation metrics comprises at least one of a mean, a standard deviation, a skewness, and a kurtosis.

In some embodiments, one or a plurality of sound propagation metrics characterizes at least one of sound speed, sound attenuation, and sound reflection. In some embodiments, one or a plurality of sound propagation metrics comprises at least a sound speed metric and a reflection metric. In some embodiments, one or a plurality of sound propagation metrics comprises at least a sound speed metric, a reflection metric, and an attenuation metric. In some embodiments, one or a plurality of sound propagation metrics comprises at least a sound speed metric, a reflection metric, an attenuation metric, and a user defined score. In some embodiments, one or a plurality of sound propagation metrics comprises at least a sound speed metric, a reflection metric, an attenuation metric, and morphological metric. In some embodiments, one or a plurality of sound propagation metrics comprises at least a sound speed metric, a reflection metric, an attenuation metric, a morphological metric, and a user defined score.

In some embodiments, a set of prognostic parameters is trimmed. In some embodiments, trimming the set of prognostic parameters is aided by the processor. In some embodiments, the processor trims the set of prognostic parameters based on a method selected from the group consisting of: principle component analysis, multilinear principle component analysis, and decision tree analysis. In some embodiments, one of the plurality subsets comprises the one or a plurality of sound propagation metrics characterizing sound speed. In some embodiments, one of the plurality subsets comprises the one or a plurality of sound propagation metrics characterizing sound attenuation. In some embodiments, one of the plurality subsets comprises the one or a plurality of sound propagation metrics characterizing sound reflection.

In some embodiments, a classifier model determines a type of tissue with a sensitivity at least 85% and a specificity of at least 84%. In some embodiments, a classifier model determines a threshold value of one or more prognostic parameters sufficient to classify a tissue. In some embodiments, a classifier model determines a relative statistical accuracy of one or more prognostic parameters. In some embodiments, a relative statistical accuracy is a specificity or sensitivity of tissue classification.

In some embodiments, a classifier model builds a decision tree based on the accuracy of said one or more prognostic parameters. In some embodiments, a classifier model builds a decision tree based on the accuracy of said subset of prognostic parameters. In some embodiments, a classifier model determines a threshold value of a said subset prognostic parameters sufficient to classify a tissue using said decision tree. In some embodiments, a classifier model determines a threshold value of a said subset prognostic parameters sufficient to classify a tissue.

In some embodiments, a classifier model has been generated with a machine learning technique. In some embodiments, a machine learning technique comprises a support vector machine. In some embodiments, a support vector machine comprises LibSVM. In some embodiments, a machine learning technique comprises a decision tree. In some embodiments, a decision tree comprises J48, C4.5, or ID3. In some embodiments, a decision tree comprises ADABoost or DecisionStump. In some embodiments, a machine learning technique comprises a neural network. In some embodiments, a machine learning technique comprises k-nearest neighbors. In some embodiments, a machine learning technique comprises a Bayes classification.

BRIEF DESCRIPTION OF THE DRAWINGS

A better understanding of the features and advantages of the present subject matter will be obtained by reference to the following detailed description that sets forth illustrative embodiments and the accompanying drawings of which.

DETAILED DESCRIPTION

Figure 1A:
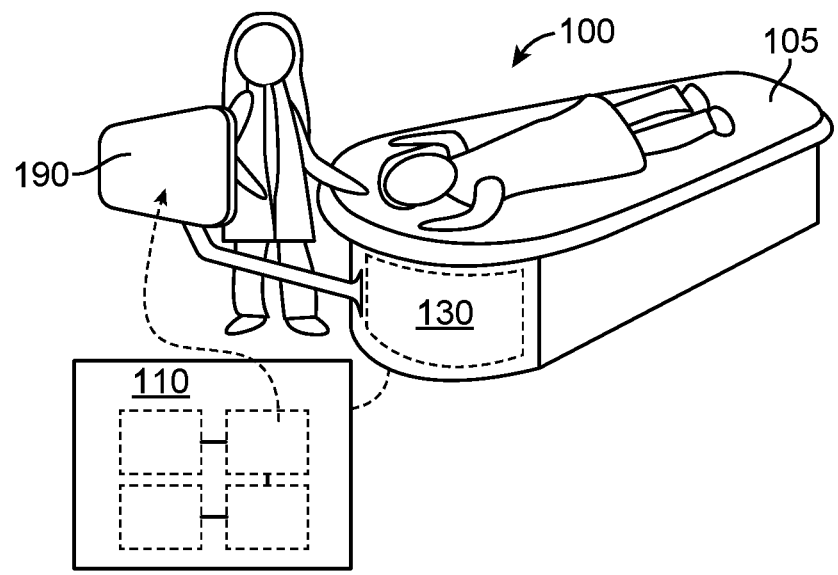
FIG. 1A, FIG. 1B, and FIG. 1C illustrate a schematic of an example ultrasound scanner, a schematic of a patient breast in an example ultrasound scanner, and a schematic of an example ultrasound transducer of an ultrasound scanner, respectively, in accordance with some embodiments.

Disclosed herein are systems and methods for image data segmentation, feature extraction, feature selection, and tissue classification based on machine learning algorithm(s). In some embodiments, disclosed herein are selections of different features subsets (e.g., a single feature class or features from multiple classes) which affect the classification accuracy.

The methods and apparatus disclosed herein are well suited for combination with prior ultrasound tomography (UST) may advantageously provide a remedy to the deficiencies of current standards for breast cancer screening. The methods and apparatus disclosed herein can be combined with ultrasound tomography in a manner that is less operator dependent, has more reproducibility of the data acquisition process, and can utilize both reflection and transmission information. The transmitted portion of an ultrasound signal may contain information about the sound speed and attenuation properties of the insonified medium. These properties can aid in the differentiation of fat, fibroglandular tissues, benign masses, and malignant cancer, and are well suited for combination with the methods and apparatus disclosed herein.

When a radiologist views ultrasound tomography images, they process the data and reach a conclusion on whether the image has some type of breast disease. Disclosed herein are systems and methods that utilize machine learning and data mining techniques to process and classify ultrasound tomography images to reach a conclusion on whether the image shows a specific type of breast abnormality.

Disclosed herein, in some embodiments, tissue characterization of ultrasound images (e.g., ultrasound tomography) using machine learning techniques requires a series of steps. In some cases, a set of images containing examples of different types of tissues and masses can be generated. A trained radiologist can then locate and segment the tissue of interest by generating a region-of-interest (ROI) mask (e.g., binary). Features can then be extracted from the ROI. Using feature selection technique(s), the most relevant features are then fed to train a machine learning classifier model. The trained classifier can then be fed features from an unknown tissue sample to predict a label or classification for the sample. A prediction of a label or a classification may include a probability that a lesion is of a particular type. A predication of a label or a classification may include a score.

In some embodiments, the systems and methods herein using machine learning and data mining techniques on ultrasound tomography images have two different pipelines. The first pipeline is the classifier model generation which is referred to as offline learning. The second pipeline is the actual radiologists' (or other users') use of the classifier model to data mine and classify images which is referred to as online use.

In some embodiments, the offline learning process includes a uniform image generation: all raw data in the training set is reconstructed with specified image reconstruction parameters, e.g., uniform image reconstruction parameters. An aspect of ultrasound tomography is the generation of multiple image stacks, each comprising sequential images through a three-dimensional volume of tissue, e.g. a breast. Each image stack can represent different acoustic components of that three-dimensional volume. In some embodiments, different reflection and transmission components are utilized, with the predominant transmission components including sound speed and attenuation. Various permutations of these combinations can be combined to provide improved tissue differentiation, such as the combination of standard grayscale reflection with color overlays of the thresholded values of sound speed and attenuation in order to better represent tissue stiffness. Similarly, mass effect can be accentuated on reflection by incorporating sound speed data for improved contrast from background normal tissue.

Described herein in some embodiments is a computer implemented method for characterizing a lesion in a volume of tissue. The method may comprise: receiving a plurality of acoustic renderings, the acoustic renderings comprising a representation of sound propagation through the volume of tissue, wherein the plurality of acoustic renderings comprises at least a transmission rendering and a reflection rendering; determining a set of prognostic parameters, wherein the set of prognostic parameters comprises one or a plurality of sound propagation metrics that are derived from the plurality of acoustic renderings; assigning each element of the set of prognostic parameters a predictive value, wherein the predictive value is based on a plurality of classified acoustic renderings; forming a classifier model from a subset of the set of prognostic parameters, the subset determined based on the predictive value of each of at least a subset of the set of the prognostic parameters; and calculating a score using the classifier model, the score relating to a probability that the lesion is of a classification.

Described herein in some embodiments, is a processor comprising a tangible medium. The tangible medium may be configured with instructions to: receive a plurality of acoustic renderings, the acoustic renderings comprising a representation of sound propagation through the volume of tissue, wherein the plurality of acoustic renderings comprises at least a transmission rendering and a reflection rendering; determine a set of prognostic parameters, wherein the set of prognostic parameters comprises one or a plurality of sound propagation metrics that are derived from the plurality of acoustic renderings; assign each element of the set of prognostic parameters a predictive value, wherein the predictive value is based on a plurality of classified acoustic renderings; form a classifier model from a subset of the set of prognostic parameters, the subset determined based on the predictive value of each of at least a subset of the set of the prognostic parameters; and calculate a score using the classifier model, the score relating to a probability that the lesion is of a classification.

Described herein in some embodiments, is a computer implemented method for classifying a lesion in a volume of tissue. The method may comprise: receiving a plurality of acoustic renderings, the acoustic renderings comprising a representation of sound propagation through the volume of tissue, wherein the plurality of acoustic renderings comprises at least a transmission rendering and a reflection rendering; indicating a region of interest within the volume of tissue, wherein the region is proximate the lesion within the volume of tissue; segmenting a portion of at least one of the plurality of acoustic renderings near the region of interest; providing an indication that the portion is in an interior or an exterior of the lesion; generating a mask, wherein the mask comprises a prediction of a shape of the lesion; and determining a set of prognostic parameters, wherein the set of prognostic parameters comprises one or a plurality of sound propagation metrics that are derived from the plurality of acoustic renderings.

Described herein, in some embodiments, is a processor comprising a tangible medium configured with instructions to: receive a plurality of images the tissue of a subject, the plurality of images selected from the group consisting of a transmission image and a reflection image, wherein the plurality of images is generated from a plurality of acoustic signals derived from acoustic waveforms transmitted through the volume of tissue; provide a set of prognostic parameters associated with a user selected region of interest; wherein the set of prognostic parameters comprises one or a plurality of sound propagation metrics characterizing sound propagation within a tissue; wherein the set of prognostic parameters corresponds to inputs into a tissue classifier model; wherein the set of prognostic parameters comprises a plurality of subsets of related feature groupings; and determine a type of tissue of the subject based on said plurality of subsets of related feature groupings using the classifier model, wherein the type of tissue is selected from the group consisting of a cancerous tumor, a fibroadenoma, a cyst, a nonspecific benign mass, and an unidentifiable mass. In some embodiments, a region of interest may be within at least one of a plurality of acoustic renderings. In some embodiments, a user may select a region of interest by selecting a portion of an acoustic rendering, such as by drawing a shape, on at least one acoustic rendering.

Disclosed herein, in some embodiments, is a method of determining a type of tissue with a classifier model, which method is implemented by a computer comprising one or more processors and computer readable storage media comprising instructions, the method comprising: receiving a plurality of images the tissue of a subject, the plurality of images selected from the group consisting of a transmission image and a reflection image, wherein the plurality of images is generated from a plurality of acoustic signals derived from acoustic waveforms transmitted through the volume of tissue; providing a set of prognostic parameters associated with a user selected region of interest; wherein the set of prognostic parameters comprises one or a plurality of sound propagation metrics characterizing sound propagation within a tissue, wherein the set of prognostic parameters corresponds to inputs into a tissue classifier model, and wherein the set of prognostic parameters comprises a plurality of subsets of related feature groupings; and determining a type of tissue of the subject, wherein the type of tissue is selected from the group consisting of a cancerous tumor, a fibroadenoma, a cyst, a nonspecific benign mass, and an unidentifiable mass using said classifier model. In some embodiments, disclosed herein is a non-transitory computer-readable storage medium with instructions stored thereon that, when executed by a processor, cause a processor to perform the method disclosed herein. In some embodiments, disclosed herein is a computer comprising the non-transitory computer-readable storage medium herein.

Definitions

Unless otherwise defined, all technical terms used herein have the same meaning as commonly understood by one of ordinary skill in the art to which this invention belongs.

As used herein, the singular forms "a," "an," and "the" include plural references unless the context clearly dictates otherwise. Any reference to "or" herein is intended to encompass "and/or" unless otherwise stated.

As used herein, the term "about" refers to an amount that is near the stated amount by about 10%, 5%, or 1%, including increments therein.

Ultrasound System

Figure 1B:
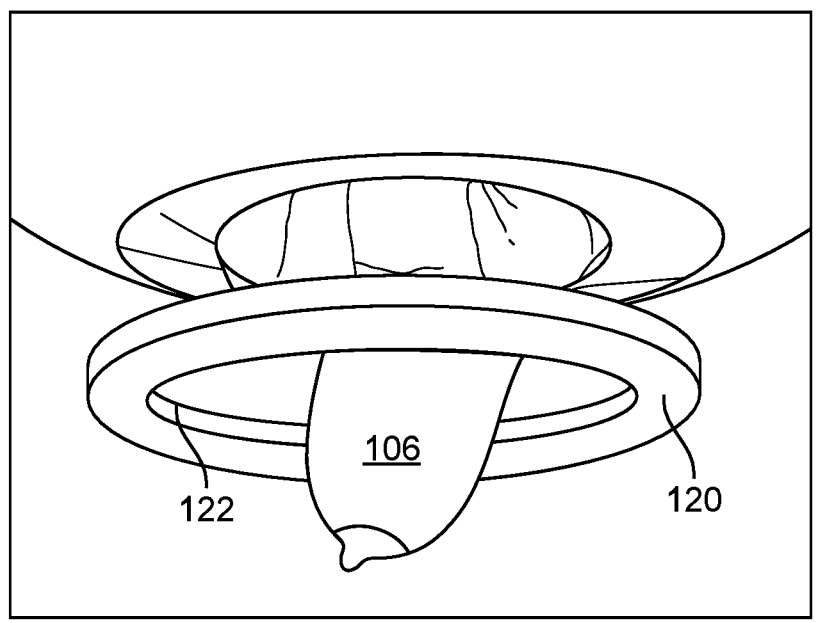
Figure 1C:
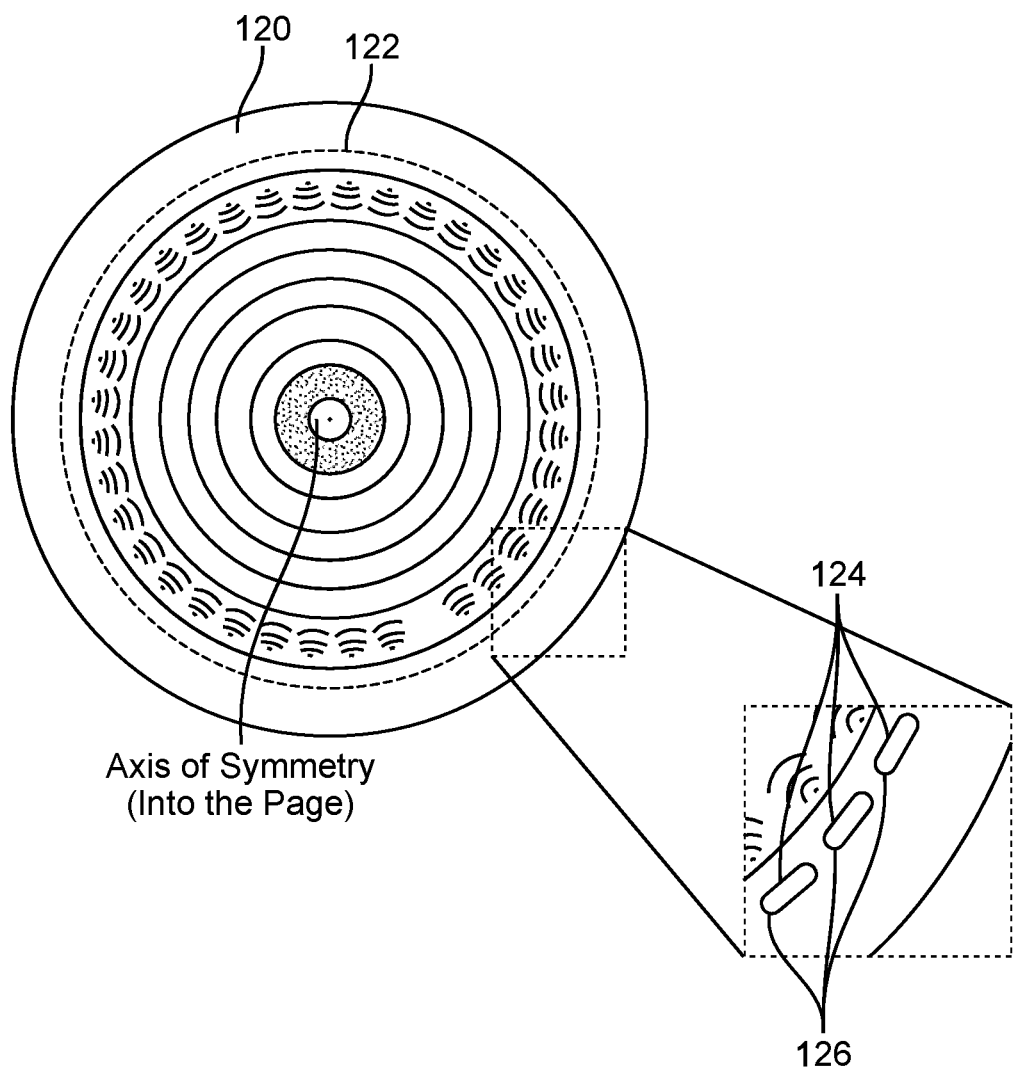

FIG. 1A, FIG. 1B, and FIG. 1C illustrate a schematic of an example ultrasound scanner, a schematic of a patient breast in an example ultrasound scanner, and a schematic of an example ultrasound transducer of an ultrasound scanner, respectively, in accordance with embodiments. As shown in FIG. 1A, FIG. 1B, and FIG. 1C, an ultrasound tomography scanner 100 may comprise a transducer 120 configured to receive the volume of tissue and comprising an array of ultrasound transmitters 124 and an array of ultrasound receivers 126. The array of ultrasound transmitters may be configured to emit acoustic waveforms toward the volume of tissue, and the array of ultrasound receivers 126 may be configured to detect a set of acoustic signals derived from acoustic waveforms transmitted through the volume of tissue. The ultrasound tomography scanner 100 may further comprise a computer 110 (e.g. a digital processing device) in communication with the transducer, comprising one or more processors and non-transitory computer-readable media with instructions stored thereon that when executed may be configured to perform the methods of generating an enhanced image of a volume of tissue, the methods of characterizing a volume of breast tissue, and embodiments and variations described herein. The ultrasound tomography scanner 100 may further comprise a display 190 in communication with the digital processing device 110 and configured to render the enhanced image of the volume of tissue.

The system 100 may function to render ultrasound images and/or generate transformed ultrasound data that may be used to generate a high resolution image of structures present within a volume of tissue. In some embodiments, the system 100 may function to produce images that may be aligned with regulatory standards for medical imaging, as regulated, for instance, by the U.S. Food and Drug Administration (FDA). The system 100 may be configured to implement at least a portion of an embodiment, variation, or example of methods described herein; however, the system 100 may additionally or alternatively be configured to implement any other suitable method.

The transducer 120, the computer processor 110, and the display 190 may be coupled to a scanner table 105, as shown in FIG. 1A and FIG. 1B. The scanner table 105 may have an opening 106 that provides access to the volume of tissue of the patient. The table, which may be made of a durable, flexible material (e.g., flexible membrane, fabric, etc.), may contour to the patient's body, thereby increasing scanning access to the axilla regions of the breast and increasing patient comfort. The opening 106 in the table may allow the breast (or other appendage) to protrude through the table and be submerged in an imaging tank 130 filled with water or another suitable fluid as an acoustic coupling medium that propagates acoustic waves.

FIG. 1B and FIG. 1C show schematics of a patient breast in an example ultrasound scanner and a schematic of an example ultrasound transducer of an ultrasound scanner, in accordance with embodiments. As shown in FIG. 1B and FIG. 1C, a ring-shaped transducer 120 with transducer elements 122 may be located within the imaging tank 130 and encircle or otherwise surround the breast, wherein each of the transducer elements 122 may comprise one of the array of ultrasound transmitters 124 paired with one of the array of ultrasound receivers 126. Multiple ultrasound transmitters 124 that direct safe, non-ionizing ultrasound pulses toward the tissue and multiple ultrasound receivers 126 that receive and record acoustic signals scattering from the tissue and/or transmitted through the tissue may be distributed around the ring transducer 120. In one embodiment, transducer 120 may be organized such that each ultrasound transmitter element may be paired with a corresponding ultrasound receiver element, each ultrasound transmitter element may be surrounded by two adjacent ultrasound transmitter elements, each ultrasound receiver element may be surrounded by two adjacent ultrasound receiver elements, and the transducer may be axially symmetric, as in FIG. 1C.

During the scan, the ring transducer 120 may pass along the tissue, such as in an anterior-posterior direction between the chest wall and the nipple region of the breast to acquire an acoustic data set including measurements such as acoustic reflection, acoustic attenuation, and sound speed. The data set may be acquired at discrete scanning steps, or coronal "slices". The transducer 120 may be configured to scan step-wise in increments from the chest wall towards the nipple, and/or from the nipple towards the chest wall. However, the transducer 120 may additionally and/or alternatively receive data regarding any suitable biomechanical property of the tissue during the scan, and in any suitable direction.

In some embodiments, the scanner table may comprise an embodiment, variation, or example of the patient interface system described in any of the references incorporated herein and additionally or alternatively in U.S. application Ser. No. 14/208,181, entitled "Patient Interface System", U.S. application Ser. No. 14/811,316 entitled "System for Providing Scanning Medium", or P.C.T. International Pat. App. Pub. No. WO2017139389 entitled "System for Shaping and Positioning a Tissue Body", which are each hereby incorporated by reference in their entirety. However, system 100 may additionally or alternatively comprise or be coupled with any other suitable patient interface system.

Image Modalities

Systems and methods of the present disclosure may comprise generating one or a plurality of images of the volume of tissue. The images may be generated by one or more computer processors described herein. The one or a plurality of images may comprise one or more of a reflection image, a speed image, and an attenuation image. In some embodiments, the systems, devices, and methods disclosed herein may comprise generation of a transmission image. A transmission image may comprise one or more of an attenuation image and a sound speed image. In some embodiments, the plurality of images comprises combined images. In some embodiments, a combined image comprises a plurality of reflection images. In some embodiments, a combined image comprises a plurality of transmission images. In some embodiments, a combined image comprises at least one reflection image and at least one transmission image.

Figures 1D, 1E:
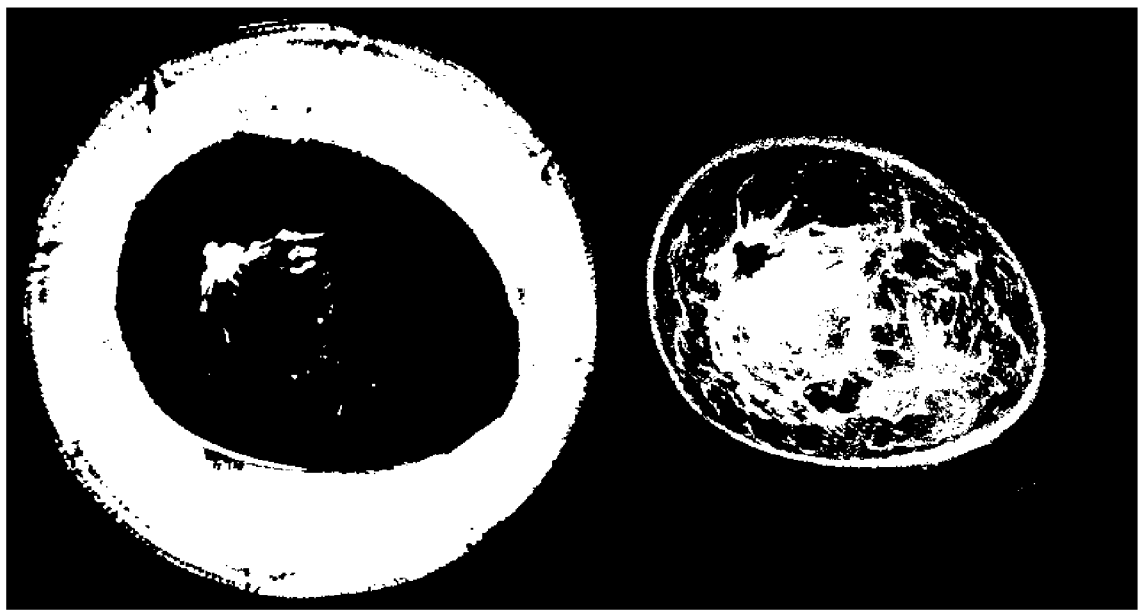
FIG. 1D, FIG. 1E, and FIG. 1F show nonlimiting examples of sound speed, reflection, and attenuation ultrasound tomography images of a breast, respectively, in accordance with some embodiments.
Figure 1F:

The one or a plurality of images may be generated from a three-dimensional rendering of an acoustomechanical parameter characterizing sound propagation within a volume of tissue. An acoustomechanical parameter may comprise at least one of, for example, sound speed, sound attenuation, and sound reflection. Each rendering may be formed from one or more "stacks" of 2D images corresponding to a series of "slices" of the volume of tissue for each measured acoustomechanical parameter at each step in a scan of the volume of tissue. Alternatively or in combination, each rendering may be in response to a model of sound propagation within the volume of tissue generated from the plurality of acoustic data received from the volume of tissue. In some cases, a radiologist uses such multiple image stacks to cross-correlate the detection and characterization of tissue abnormalities to define a mass. FIG. 1D, FIG. 1E, and FIG. 1F show example sound speed, reflection, and attenuation ultrasound tomography images of a breast, respectively.

In some embodiments, systems and methods of the present disclosure may be used to generate one or more renderings that may be used to detect abnormalities (e.g., cancerous tissues) in a human or other animal. As such, in one variation, images generated from the transducer system may be used to characterize the tissue to facilitate diagnoses of cancer, assess its type, and determine its extent (e.g., to determine whether a mass in the tissue may be surgically removable), or to assess risk of cancer development (e.g., measuring breast tissue density). In yet another embodiment, images generated from the transducer system may be used to characterize or investigate particular aspects of the tissue, such as to determine whether a mass in the tissue may be a tumor, cyst, fibroadenoma, or other kind of mass. Characterizing a lesion in a volume of tissue may be implemented, at least in part, by way of an embodiment, variation, or example of the methods in the incorporated references. Alternatively or in combination, characterizing a lesion in response to an image from a transducer system may be implemented using any other suitable method.

Embodiments of transducer systems described herein may be configured to generate a particular type of image. For example, a transducer system may be configured to acquire a particular type of image in response to a particular acoustomechanical parameter. In one embodiment, a transducer system may be configured for transmission imaging (e.g. speed imaging or attenuation imaging) and/or may be configured for reflection imaging. Images formed from the various image modalities may be merged in whole or in part to form combined image modalities. Alternatively or in combination, processing of ultrasound data may be performed using the methods described in the methods in the references incorporated herein. Such methods may include generating a waveform sound speed rendering and generating a reflection rendering.

Generating one or more image modalities may comprise a step wise scan in an anterior-posterior axis of a volume of tissue. At each step in a scan, one or more transducer elements may transmit acoustic waveforms into the volume of tissue. At each step in a scan, one or more transducer elements may receive acoustic waveforms from the tissue from the volume of tissue. The received waveforms may be converted to acoustic data. The received waveforms may be amplified. The received waveforms may be digitized. The acoustic data may comprise a speed of energy, a reflection of energy, and/or an attenuation of energy. A received waveform may be amplified and subsequently converted to acoustic data by any processor and associated electronics described herein. The received waveform may be amplified and subsequently converted to acoustic data by a processor and associated electronics.

FIG. 1D shows an example sound speed image, in accordance with some embodiments. In some embodiments, a speed image may be generated from the plurality of acoustic signals. The sound speed rendering may comprise a distribution of sound speed values across the region of the volume of tissue. Generating an acoustic sound speed rendering may comprise generating one or a plurality of two-dimensional (2D) sound speed renderings. The two-dimensional sound speed renderings may be associated with slices (e.g. coronal slices) through a volume of tissue. Generating an acoustic sound speed rendering may comprise generating a three-dimensional (3D) acoustic sound speed rendering that is a volumetric representation of the acoustic sound speed of the volume of tissue. The sound speed rendering can characterize a volume of tissue with a distribution of one or more of: fat tissue (e.g., fatty parenchyma, parenchymal fat, subcutaneous fat, etc.), parenchymal tissue, cancerous tissue, abnormal tissue (e.g., fibrocystic tissue, fibroadenomas, etc.), and any other suitable tissue type within the volume of tissue.

An image in response to a speed of energy (e.g. a speed image) may be generated using a processor 110 included with or coupled to an ultrasound tomography scanner described herein. Alternatively or in combination, an image in response to a speed of energy may be generated on any suitable processor described herein. An image in response to a speed of energy may be a sound speed rendering in response to the plurality of acoustic signals from received from the volume of tissue. Alternatively or in combination, a sound speed rendering may be generated in response to a plurality of acoustic signals from any suitable data. The sound speed map may be generated in response to a processing of sound transmission signals through the volume of tissue in addition to backscattered signals from the volume of tissue.

The sound speed map may characterize a real part of the complex valued ultrasound impedance of the volume of tissue, the rate of travel of a waveform through the volume of tissue, a ratio of distance of travel through the volume of tissue over time between transmission and detection, or any other suitable acoustic speed parameter. A stack of 2D acoustic sound speed images may be derived from the real portion of the complex-valued impedance of the tissue and may provide anatomical detail of the tissue The sound speed rendering may be generated from a waveform sound speed method. Such a method may comprise generating an initial sound speed rendering in response to simulated waveforms according to a travel time tomography algorithm. Alternatively or in combination, the initial sound speed rendering may be iteratively optimized until ray artifacts are reduced to a pre-determined a threshold for each of a plurality of sound frequency components. Additionally or in combination, the initial method rendering may be iteratively adjusted until the obtained model is good enough as a starting model for the waveform sound speed method to converge to the true model. Such a method may comprise the method described in U.S. application Ser. No. 14/817,470, which is incorporated herein in its entirety by reference.

FIG. 1F shows an example attenuation image, in accordance with some embodiments. In some embodiments, an attenuation image may be generated from the plurality of acoustic signals. The sound attenuation rendering may comprise a distribution of sound attenuation values across the region of the volume of tissue. Generating an acoustic sound attenuation rendering may comprise generating one or a plurality of two-dimensional (2D) sound attenuation renderings. The two-dimensional sound attenuation renderings may be associated with slices (e.g. coronal slices) through a volume of tissue. Generating an acoustic sound attenuation rendering may comprise generating a three-dimensional (3D) acoustic sound attenuation rendering that is a volumetric representation of the acoustic sound attenuation of the volume of tissue. The sound attenuation rendering can characterize a volume of tissue with a distribution of one or more of: fat tissue (e.g., fatty parenchyma, parenchymal fat, subcutaneous fat, etc.), parenchymal tissue, cancerous tissue, abnormal tissue (e.g., fibrocystic tissue, fibroadenomas, etc.), and any other suitable tissue type within the volume of tissue. Additionally or alternatively, generating an acoustic attenuation rendering may comprise a method described in the references incorporated herein.

An image in response to an attenuation of energy (e.g. a speed image) may be generated using a processor 110 included with or coupled to an ultrasound tomography scanner described herein. Alternatively or in combination, an image in response to an attenuation of energy may be generated on any suitable processor described herein. An image in response to an attenuation of energy may be a sound attenuation rendering in response to the plurality of acoustic signals from received from the volume of tissue. Alternatively or in combination, a sound attenuation rendering may be generated in response to a plurality of acoustic signals from any suitable data. The sound attenuation map may be generated in response to a processing of sound transmission signals through the volume of tissue in addition to backscattered signals from the volume of tissue.

The sound attenuation map may characterize an imaginary part of the complex valued ultrasound impedance of the volume of tissue, the absorption of a waveform by the volume of tissue, or any other suitable acoustic attenuation parameter. A stack of 2D acoustic sound attenuation images may be derived from the imaginary portion of the complex-valued impedance of the tissue and may provide anatomical detail of the tissue.

FIG. 1E shows an example reflection image, in accordance with some embodiments. In some embodiments, a reflection image may be generated from the plurality of acoustic signals. The sound reflection rendering may comprise a distribution of sound reflection values across the region of the volume of tissue. Generating an acoustic sound reflection rendering may comprise generating one or a plurality of two-dimensional (2D) sound reflection renderings. The two-dimensional sound reflection renderings may be associated with slices (e.g. coronal slices) through a volume of tissue. Generating an acoustic reflection rendering may comprise generating a three-dimensional (3D) acoustic reflection rendering that is a volumetric representation of the acoustic reflection of the volume of tissue. The sound reflection rendering can characterize a volume of tissue with a distribution of one or more of: fat tissue (e.g., fatty parenchyma, parenchymal fat, subcutaneous fat, etc.), parenchymal tissue, cancerous tissue, abnormal tissue (e.g., fibrocystic tissue, fibroadenomas, etc.), and any other suitable tissue type within the volume of tissue.

An image in response to a reflection of energy (e.g. a reflection image) may be generated using a processor 110 included with or coupled to an ultrasound tomography scanner described herein. Alternatively or in combination, an image in response to a reflection of energy may be generated on any suitable processor described herein. An image in response to a reflection of energy may be a sound reflection rendering in response to the plurality of acoustic signals from received from the volume of tissue. Alternatively or in combination, a sound reflection rendering may be generated in response to a plurality of acoustic signals from any suitable data.

The reflection rendering may utilize envelope detected reflection data (ERF), raw radiofrequency reflection signals (e.g., REF image data, "radiofrequency", or RF data), which can be converted to a flash B-mode ultrasound image, or any suitable ultrasound image. The distribution of acoustic reflection signals may characterize a relationship (e.g., a sum, a difference, a ratio, etc.) between the reflected intensity and the emitted intensity of an acoustic waveform, a change in the acoustic impedance of a volume of tissue, or any other suitable acoustic reflection parameter. A stack of 2D acoustic reflection images may be derived from changes in acoustic impedance of the tissue and may provide echo-texture data and anatomical detail for the tissue.

In some embodiments, the acoustic reflection rendering may be generated from a distribution of acoustic reflection signals received from an array of transducer elements transmitting and receiving at a frequency greater than the frequency of the array of transducer elements used to generate a rendering from another acoustic data type including, for example, the sound speed rendering or the attenuation rendering. In other embodiments, the acoustic reflection rendering may be generated from a distribution of acoustic reflection signals received from an array of transducer elements transmitting and receiving at a frequency less than the frequency of the array of transducer elements used to generate a rendering from another acoustic data type including, for example, the sound speed rendering or the attenuation rendering. The low frequencies (~1 MHz) may provide information on specular reflections (down to ~1 mm); however, imaging at higher frequencies (~1 to 5 MHz) may be better able to image the sub-mm granularity that provides information on speckle patterns. Therefore, it may be beneficial to generate a particular acoustic rendering at a particular frequency.

The 3D renderings of any type of acoustic data may be combined or merged in whole or in part. In one embodiment, a merged rendering may comprise combining 3D renderings of at least two types of image data. In another embodiment, a merged rendering may comprise combining at least a portion of the plurality of 2D images from at least two types of image data. Any suitable formula or algorithm may be used to merge or fuse the various renderings into a single rendering. In some embodiments, the combined image may be an enhanced reflection image. In such embodiments, the processor may be configured to generate an enhanced reflection image from a reflection image and a speed image.

An enhanced image may comprise an embodiment, variation, or example of the system and method for generating an enhanced image of a volume of tissue described in commonly assigned applications: U.S. patent application Ser. No. 15/829,748 and P.C.T. App. No. US2017/064350, which are each incorporated herein by reference in their entirety. Briefly, systems and methods of the cited reference may combine a reflection image generated from detection a reflected signal from a volume of tissue and a speed image to generate an enhanced reflection image. The second reflection image may be generated from a gradient of a sound speed image, and the two reflection images may be combined as described in the incorporated references.

Characterizing a Volume

Figure 2:
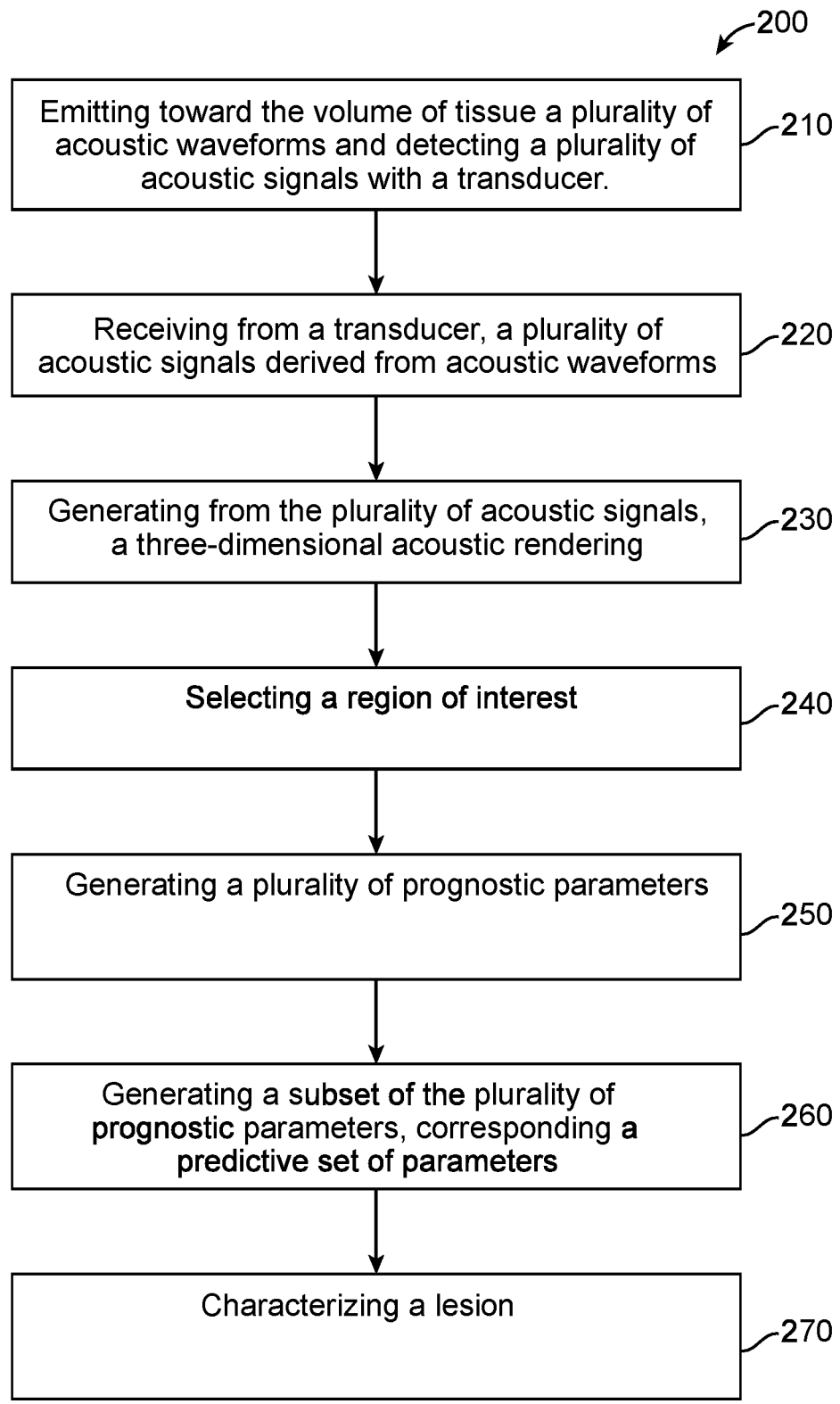
FIG. 2 illustrates an example method for characterizing a volume of breast tissue of a patient, in accordance with some embodiments.

Embodiments of the present disclosure provide a method for characterizing a volume of breast tissue of a patient. The method may be implemented by a computer comprising one or more processors and computer readable media comprising instructions. FIG. 2 shows an example method 200 for characterizing a volume of breast tissue of a patient, in accordance with some embodiments. A method 200 may comprise emitting toward the volume of tissue a plurality of acoustic waveforms and detecting from the volume of tissue a plurality of acoustic signals with a transducer, wherein the transducer may comprise an array of ultrasound transmitters and an array of ultrasound receivers configured to surround the volume of tissue 210. The method 200 may further comprise receiving from a transducer, a plurality of acoustic signals derived from acoustic waveforms transmitted through the volume of tissue 220. The method 200 may further comprise generating from the plurality of acoustic signals, a three-dimensional acoustic rendering that characterizes sound propagation within the volume of tissue 230. The method 200 may further comprise selection of a region of interest 240. The method 200 may further comprise generating from the acoustic rendering a plurality of prognostic parameters corresponding to sound propagation 250. The method 200 may further comprise generating from the acoustic rendering a subset of the plurality of prognostic parameters corresponding to a predictive set of parameters 260. The method 200 may further comprise characterizing a lesion within the volume of tissue using the subset of prognostic parameters 270.

In some embodiments, method 200 may function to characterize a volume of tissue (e.g., a whole breast, another organ) according to a rendering of ultrasound images that enhance target objects within a field of view. Additionally or alternatively, the volume of tissue may comprise a distribution of one or more of: fat tissue (e.g., fatty parenchyma, parenchymal fat, subcutaneous fat, etc.), parenchymal tissue, cancerous tissue, abnormal tissue (e.g., fibrocystic tissue, fibroadenomas, etc.), and any other suitable tissue type within the volume of tissue. Method 200 may be used to characterize tissue of a human breast, but may additionally or alternatively be used to characterize tissue of an arm, leg, other appendage, and/or any suitable volume of tissue in a human or other animal. In relation to current ultrasound methods and systems, method 200 may improve specificity in characterization of types of masses by up to 10%, for example, within a range defined between any two of the following values: about 0.1%, about 1%, about 5%, and about 10%. Such masses may include but are not limited to: a cancerous tumor, a fibroadenoma, a cyst, a nonspecific benign mass, and an unidentifiable mass. Method 200 may, however, function to enable diagnosis, monitoring, and/or characterization of a volume of tissue in any other suitable manner.

In some embodiments, method 700 may be used to characterize the tissue to facilitate diagnoses of cancer, assess its type and determine its extent (e.g., to determine whether a mass in the tissue may be surgically removable), or to assess risk of cancer development (e.g., measuring breast tissue density). In yet another embodiment, method 200 may be used to characterize and/or investigate particular aspects of the tissue, such as to determine whether a mass in the tissue may be a tumor, cyst, fibroadenoma, or other kind of mass. Method 200 may be used in any suitable application for imaging a volume of tissue or other suitable object. Method 200 may be implemented, at least in part, by way of an embodiment, variation, and/or example of the system 100 described in the section titled "Ultrasound System" elsewhere herein; however, method 200 may additionally or alternatively be implemented using any other suitable system.

While FIG. 2 shows a method of generating an enhanced image of a volume of tissue, in accordance with embodiments, a person of ordinary skill in the art will recognize many adaptations and variations. Further, one or more steps shown in FIG. 2 may be deleted or repeated, additional steps can be added, and the steps can be performed in any order.

At a step 210 of the method 200, a plurality of acoustic waveforms may be emitted toward the volume of tissue and a plurality of acoustic signals may be detected from the volume of tissue with a transducer. The transducer may comprise an array of ultrasound transmitters and an array of ultrasound receivers configured to surround the volume of tissue. At a step 220 of the method 200, a plurality of acoustic signals derived from acoustic waveforms transmitted through the volume of tissue may be received by a computer from a transducer. Steps 210 and 220 function to gather acoustic data from which renderings of the volume of tissue may be derived in other steps of the method 200. At step 210 of the method 200, emitting acoustic waveforms and detecting a set of acoustic signals may be performed with an ultrasound tomographic scanner 100, for example as described in the section titled "Ultrasound System", and using methods similar to those described in the incorporated references. However, any suitable ultrasound device or scanner may be used.

At a step 230 of the method 200, a three-dimensional acoustic rendering that characterizes sound propagation within the volume of tissue may be generated from the plurality of acoustic signals. The acoustic signals may be processed by a computer as acoustic data. Acoustic data may be used to generate one or more "stacks" of 2D images corresponding to a series of "slices" of the volume of tissue for each measured acoustomechanical parameter. Each stack of 2D image data may comprise acoustic data associated with a particular parameter or property of the tissue, for example, any type of acoustic data such as acoustic reflection, acoustic sound speed, and acoustic attenuation. The processor 110 may additionally or alternatively generate a three-dimensional volumetric rendering based on the stack of two-dimensional images, and/or generate a three-dimensional volumetric rendering directly based on the received acoustic data. An image representation of any portion of the volume of tissue may depict any one or more acoustomechanical properties of the volume of tissue. For example, an image representation may depict acoustic attenuation, acoustic reflection, acoustic speed, and/or any suitable property of the tissue.

Additionally or alternatively, a step 230 may be performed using a method 200 for method of characterizing a volume of tissue described herein. Additionally or alternatively, a step 230 may be performed using the methods described herein in the section titled "Image Modalities" and in the methods in the incorporated references. Such methods may include generating a waveform sound speed rendering and generating a first reflection rendering.

In one embodiment, a slice may correspond to regions of a volume of tissue scanned in an anterior to posterior manner (e.g., in coronal slices); however, the slices may correspond to slices in any other direction (e.g., at any angle relative to the anterior-posterior direction, in an inferior-superior direction, at any angle relative to the inferior-superior direction, in a medial-lateral direction, at any angle relative to the medial-lateral direction, etc.). Each acoustic data point within an acoustic slice may be associated with a particular value on a grid, including a position along the sliced axis, such that slices and the data may be ordered relative to each other to image the volume of tissue.

Region of Interest Selection

A region of interest (ROI) may be identified by a user based on the 3D renderings of any form acoustic data including acoustic attenuation, acoustic sound speed, and acoustic reflection and additionally including combined or merged renderings. A user selected ROI can be a two-dimensional ROI or a three-dimensional ROI. The ROI may correspond to a mass within for example a breast tissue. The mass may be for example, a cancerous mass, a benign fibroadenoma, a cyst, another benign finding, an unidentifiable mass (for example, there may be no finding), or any suitable characterization or classification. In one embodiment, the ROI may be selected by a user, for example, by tracing the ROI "free-hand" or drawing a simple shape such as a circle or ellipse. In some embodiments, selection of a region of interest is performed without the aid of a user. In some embodiments, a user place a mouse on a point in an image and a region of interest is generated by a processor.

The selection of a user selected region of interest, such as a two-dimensional region of interest, can be aided by a processor. Additionally or alternatively, the selection of an ROI may be aided or optimized by a computer-implemented algorithm, wherein the computer comprises a processor with instructions to implement the algorithm. The processor may aid or optimize selection of an ROI based on threshold values of any acoustic data type and/or multiples of data types including combinations of data types. The processor may aid or optimize selection of an ROI based on a known morphology, such as through the use of image recognition algorithms. For example, the processor may aid or optimize selection of the ROI using a machine learning algorithm trained from a set of images of any acoustic data type exhibiting variously classified lesions. In another example, the machine learning algorithm may be trained on a set image data including qualitative morphological features (e.g., a user-assessed score based on shape), quantitative morphological features (e.g., calculated ellipticity, spiculation), and quantitative features (speed, attenuation, reflection, etc.). In some cases, a processor can aid selection of a region of interest by using an edge detection algorithm. In some cases, a processor can aid selection of a region of interest using a set of prognostic parameters. In some cases, a processor can use a combination of an edge detection algorithm and a set of prognostic parameters to aid in selection of a region of interest.

A three-dimensional region of interest can be used to generate a three-dimensional region of interest. This can be accomplished for example by using a processor. In some cases, a mask can be generated based on a region of interest. A mask can be of a two-dimensional region of interest or of a three-dimensional region of interest.

In some embodiments, a set of prognostic parameters can be provided based on a region of interest, such as a two-dimensional region of interest or a three-dimensional region of interest. In some cases, the set of prognostic parameters can be determined by a processor. A set of prognostic parameters provided can comprise at least 1, 2, 5, 10, 15, 20, 25, 30, 35, 40, 45, 50, or 100 prognostic parameters.

Identification of a particular two-dimensional region-of-interest (ROI) may be done in several manners, such as hand-drawn by the operator/radiologist to carefully trace the boundaries of the potential mass. In some embodiments, a user draws a region-of-interest (ROI) on one or more images of the multiple image stacks to segment out a particular type of tissue, including but not limited to cysts, fibroadenomas, cancers, peritumoral tissue, parenchymal tissues, adipose tissues, and skin. In some embodiments, the region of interest may be a three-dimensional region of interest, such as volume of interest formed from stacks of two-dimensional regions of interest.

Figure 3A:
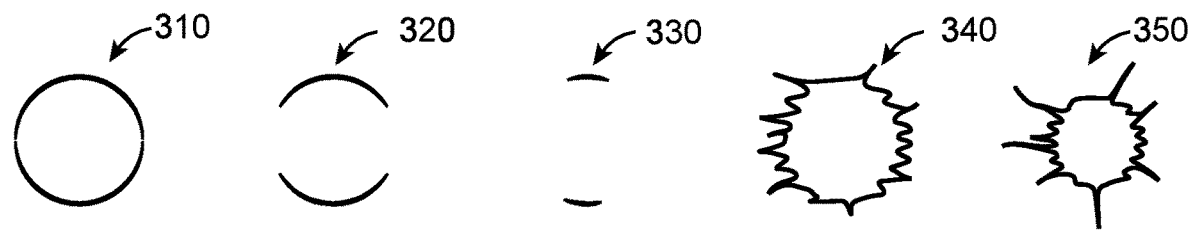
FIG. 3A illustrates example regions of interest comprising various user selected and/or computer selected margin boundaries and additionally comprising varying boundary morphologies, in accordance with some embodiments.

The ROI may comprise a margin boundary between the ROI and the surrounding tissue. FIG. 3A shows example ROIs comprising various user-selected and/or computer selected margin boundaries and additionally comprising varying boundary morphologies, in accordance with embodiments. The margin boundary may be completely identified at the start of analysis; however, additionally or alternatively, the margin boundary may be incomplete at the start of analysis and optimized by a computer program. In FIG. 3A, the left three margin boundaries show various degrees of completeness at the start of analysis. The margin boundary 310 is greater than two-thirds complete; margin boundary 320 is between one-third and two-thirds complete; margin boundary 330 is less than ⅓ complete.

The margin boundary may also comprise a morphology which may be used in a classifier model. Such morphologies may comprise, for example, those with smooth edges, those with irregular and/or rough edges, for example, those which have one or a plurality of elongate elements or those which may be speculated, those which may be predominantly round or ellipsoid, or any other shape which a lesion in a tissue may reasonably take. Margin boundaries 340 and 350 are complete and show example morphologies of the margin boundary. Margin boundary 340 shows an irregular margin boundary. Margin boundary 350 shows significant speculation, such as may indicate a cancerous lesion.

From a selected ROI with an identified margin boundary, one or a plurality of interior and exterior regions of interest may be identified. The interior region(s) of interest may comprise one or a plurality of layers starting at the margin boundary and continuing further inside the ROI. The exterior regions of interest may comprise one or a plurality of layers starting at the margin boundary and continuing further outside the ROI. The interior and exterior layers of the ROI may each comprise layers classified as "near" and "distant". The "near" layers may be classified as being close to the boundary. The "distant" layers may be classified as being far from the boundary. For example, the interior layers of the region of interest may comprise layers near the boundary and distant from the boundary. For example, the external layers of the region of interest may comprise layers near the boundary and distant from the boundary.

Figure 3B:
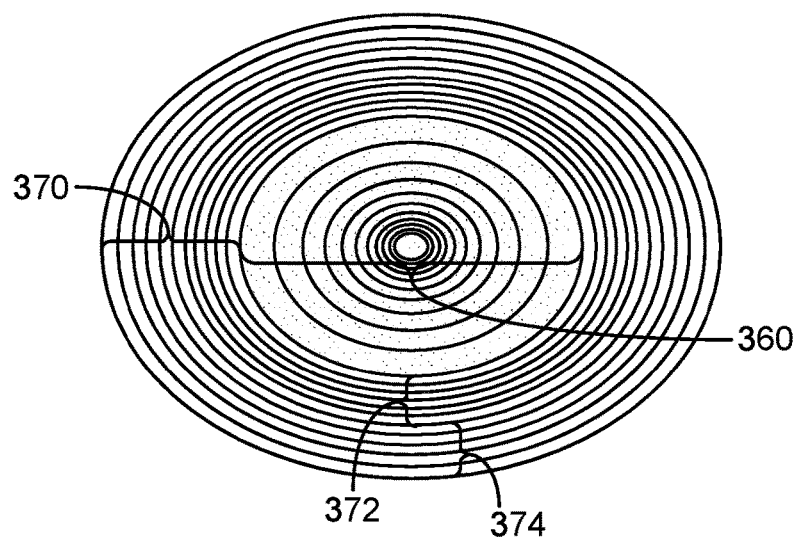
FIG. 3B illustrates an example of an ellipsoidal region of interest with a margin boundary and internal and external layers, in accordance with some embodiments.

FIG. 3B shows an exemplary ellipsoidal ROI 360 with a margin boundary and internal and external layers, in accordance with embodiments. The margin boundary may be selected by a user and additionally or alternatively selected by a user and optimized with the aid of a computer implemented algorithm. The exemplary ROI in FIG. 3B is ellipsoidal; however, an ROI may have any morphology that a lesion may take, some of which are listed with reference to FIG. 3A. Additionally or alternatively, the ROI in FIG. 3B may correspond to an initial ROI selected by a user to be optimized or assisted by a computer program. ROI 360 has an interior in grey and an exterior 370 in white. The exterior of the ROI may extend further than the lines drawn around the ROI in FIG. 3B.

In some embodiments, the interior of ROI 360 may be segmented into layers shown with solid lines drawn inside the grey area. FIG. 3B shows an interior of a region of interest which has been segmented into 10 layers; however, the interior of the ROI can be segmented into any number of layers. The layers maybe evenly spaced or may get smaller or larger from interior to exterior. Additionally or alternatively, the exterior of ROI 360 may be segmented into layers shown with solid lines drawn outside of ROI 360. FIG. 3B shows an exterior of a region of interest which has been segmented into 10 layers; however, the exterior of the ROI can be segmented into any number of layers. The layers maybe evenly spaced or may get smaller or larger from interior to exterior. The ROI can be segmented into layers before or after finalization of an ROI.

Additionally or alternatively, a set of layers interior or exterior to the region of interest may be classified as "near" or "distant". Exterior region 370 in FIG. 3B has five layers classified as "near" 372 and five layers classified as "distant" 374. The number of layers classified as near or distant may comprise any subset of layers interior or exterior to the region of interest. Additionally or alternatively, the layers may be divided evenly into near and distant or unevenly. Additionally or alternatively, the layers classified near and distant may overlap such that an individual layer may fall into both the near and distant classification. The layers may be classified as near or distant before or after finalization of the ROI.

Figure 4A:
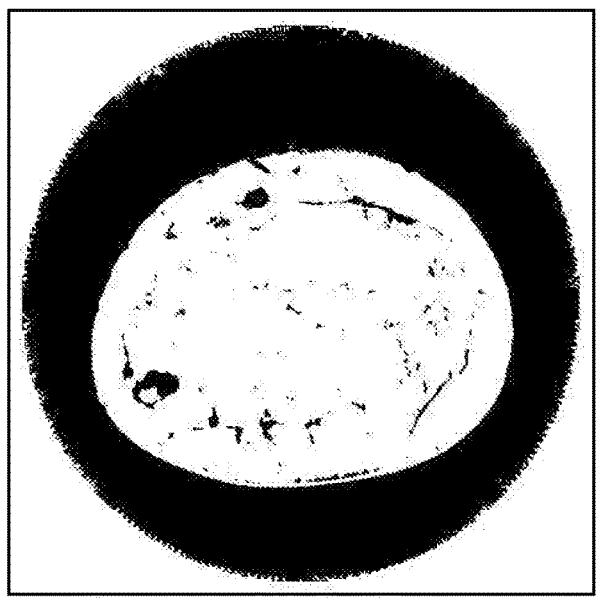
FIG. 4A illustrates an example of a sound speed ultrasound tomography image with a well-circumscribed bilobed fibroadema, in accordance with some embodiments.
Figure 4B:
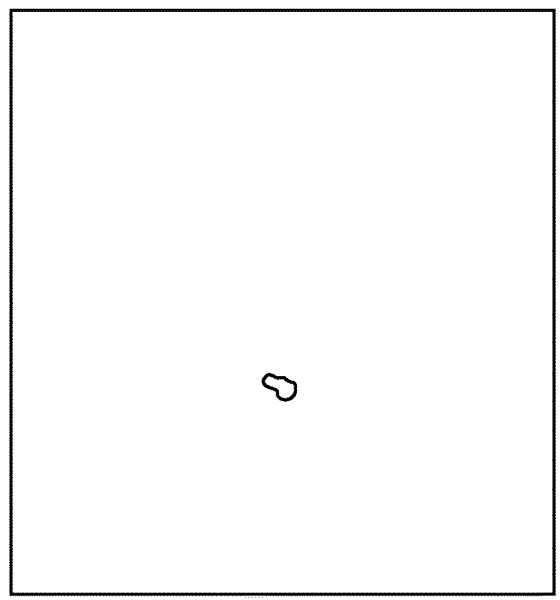
FIGS. 4B and 4C illustrate non-enlarged and enlarged binary masks of a region of interest generated from the image in FIG. 4A, respectively, in accordance with some embodiments.
Figure 4C:
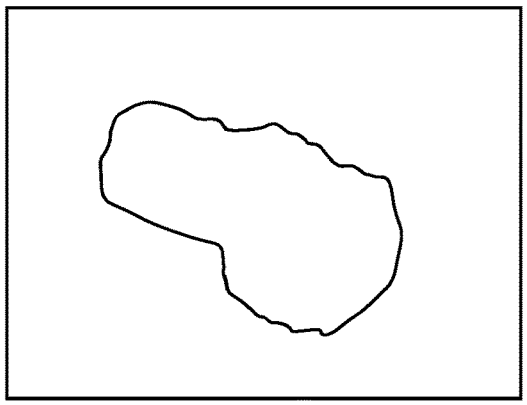
Figure 4D:
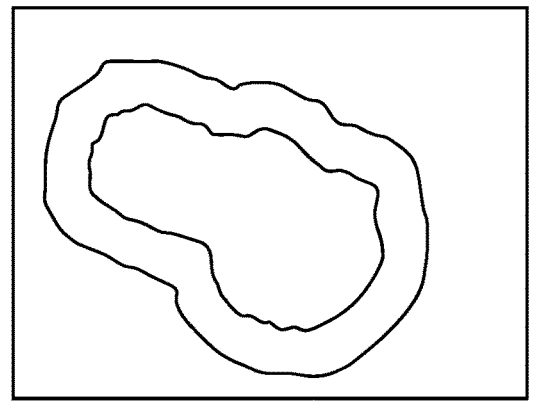
FIG. 4D and FIG. 4E illustrate examples of how an ROI can be expanded to assess features within surrounding peritumoral regions, in accordance with some embodiments.
Figure 4E:
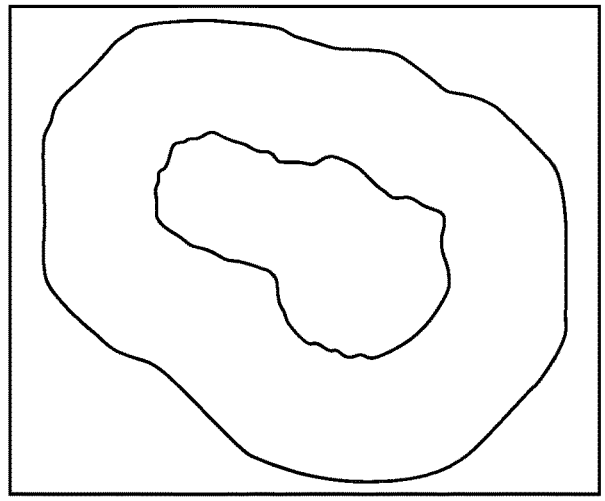
Figure 5A:
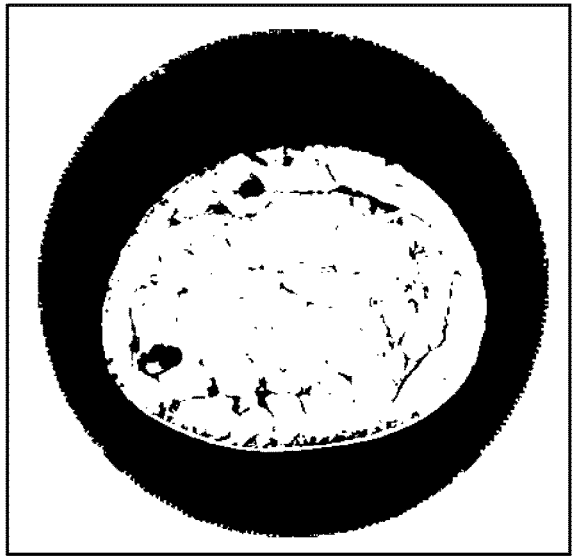
FIG. 5A, FIG. 5B, FIG. 5C, and FIG. 5D illustrate a sound speed image, an edge-edge map of the sound speed image, an edge-spot-spot-edge map of the sound speed image, and the edge-spot-spot-edge map in 4-bit color, respectively, in accordance with some embodiments.
Figure 5B:
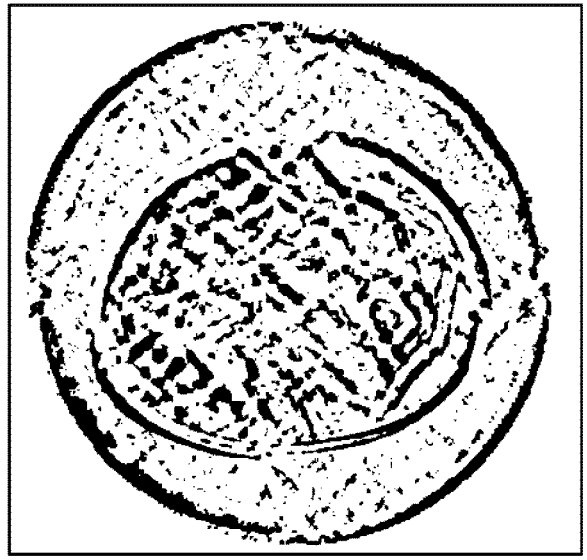
Figure 5C:
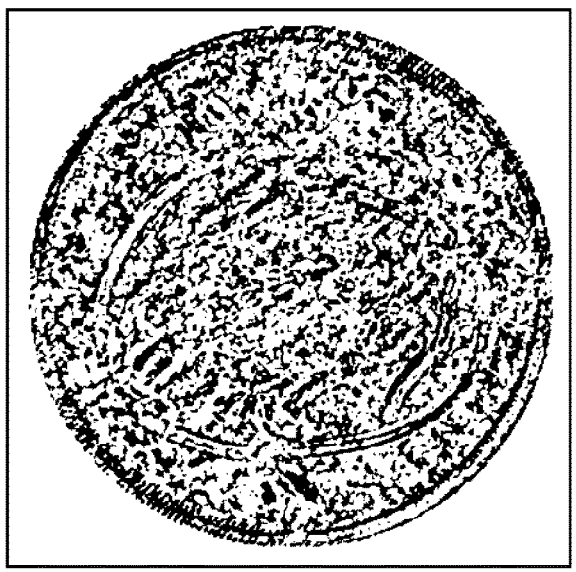
Figure 5D:
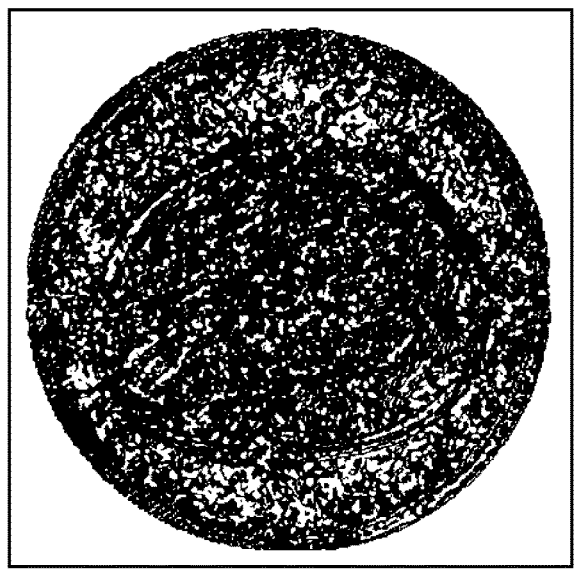

FIG. 4A shows an example of a sound speed ultrasound tomography image with a well-circumscribed bilobed fibroadenoma in the peripheral 8:00 position. In this case, a mask ROI is drawn (manually, semi-automatically, or automatically) around the mass in FIG. 4A to generate a binary mask as seen in FIGS. 4B and 4C (enlarged). The ROI can be expanded to assess features within the surroundings peritumoral region as shown in FIGS. 4D and 4E. In some embodiments, instead of using a detailed ROI as shown in FIGS. 4A-4E, an elliptical ROI encompassing the entirety of the lesion and other surrounding tissue can also be created or morphed from the original ROI.

The time-consuming ROI drawing may be simplified by a simple ellipsoid approximating mass margins or automated by an edge detection process. Disclosed herein is an edge detection process, whereby an algorithm has been trained to utilize data drawn from the multiple image stacks for better definition of a two-dimensional (2D) margin chosen on an optimal representative slice through the mass in conjunction with a radiologist. Thereby, a simple rectangle or other contour (oval, circle, irregular shape, etc) may be drawn surrounding the mass target to initiate the mass boundary detection. The algorithm can be trained to recognize powerful predictors of benign masses. If a smooth curved boundary is detected over a significant portion of that region, a circle or ellipsoid may be completed by the program to emphasize anticipated benign margins along portions that may be more ill-defined. This may help avoid potential inaccurate estimates of irregular boundaries for benign masses since irregular margins are a powerful predictor of malignancy, compared with benign masses. In some cases, a user may be given the choice to accept an edge detected for the region for any further appropriate edits. Alternatively, an irregular boundary may be accepted on any image stack that has further input to eventual machine learning of the probability for malignancy.

Once the 2D ROI has been identified from a slice (e.g., xy axes) through a lesion for mass margin detection, the process can be readily expanded utilizing the multi-parametric process herein which can utilize pixel intensity values from the plurality of imaging modalities to decide the extent of the mass margin. The margins defined by the 2D ROI (which in some cases are additionally accepted by the radiologist) may define characteristics which can then be applied to adjacent slices for a three-dimensional (3D) mass extent. In some embodiments, the algorithm can thus reduce its research of adjacent images to the region originally defined by the initial rectangle on subsequent adjacent images. Applying the characteristics detected within the radiologist defined 2D approximate equatorial image can then be applied to define the effective polar extent of the mass in the Z direction. The 3D extent of the segmented image can thus undergo a segmentation and masking process to generate a 3D ROI. The segments can be binary masks (i.e. a value of 0 if not in the ROI and a value of 1 if in the ROI). The binary mask may define the boundary morphology of the tissue type. In some cases, the mask may not be binary. For example, the mask may be softened of at the lesion margins.

Feature Extraction

In some embodiments, the lesion in a volume of tissue may be characterized from the one or more images in response to a user assessed score. However, in many case, it may be more ideal to not use a user assessed score. Methods and systems herein may be adapted to be used substantially without user input. In some embodiments, the user assessed score may be assessed from an existing classification method such as the BI-RADS criteria, which may be predominantly devoted to assessment of tumor shape, margins, and interaction with adjacent tissue. Such criteria as "shadowing" or "enhanced through transmission" in the BI-RADS may not be applicable ultrasound tomographic methods described herein; however, other criteria may be more sensitively detecting using ultrasound tomography, such as specular reflections of benign mass capsules, or the spiculations or architectural distortions of many cancers. In other embodiments, an adapted user-selected classification system may be implemented, which has been optimized for ultrasound tomographic imaging, such as a margin boundary score. Such a method may be based on a 5-point scale (the margin boundary score) that combines US-BI-RADS criteria for tumor margins as well as peritumoral tissue interaction. Methods of assessing a score may be implemented, at least in part, by way of an embodiment, variation, or example of methods in the incorporated references.

In some embodiments, the systems and methods herein provide a set of prognostic parameters, equivalently herein as features, associated with a ROI. Such a ROI can be a two dimensional ROI. In some cases, such a ROI can correlate with a region which can comprise all or a portion of a tumor or peri-tumor. In some cases, such a ROI can correlate with a region which can be sufficiently near a tumor or peri-tumor.

An ROI can be user selected. In some instances, user selection of an ROI can indicate a starting point, which can be a point or region which may overlap or be in proximity to a tumor or peri-tumor. For example, a user might indicate a ROI as a closed loop, an arc, a circle, a dot, a line, or an arrow.

In some cases, a prognostic parameter can comprise a user-assigned classification of a ROI. Such a user-assigned classification can occur at the same time or at a different time as the determination of the ROI. In some cases, a user-assigned classification can occur after the determination of the ROI. In some case, a user-assigned classification may not be used.

Features may be extracted from a region of a ROI. In some embodiments, features may also be extracted from an expanded region known as the peritumoral region surrounding the ROI. Such expanded region can be generated using various methods. One example method may be to add a uniform distance in each direction. Another example method can include finding the radius of the circle with an equivalent area of the ROI. This radius can be expanded by some multiplicative factor and the difference between the original and expanded radius can be added to each direction of the ROI. Likewise, this method can be modified such that there is a lower or upper threshold for the minimum and maximum radius sizes, respectively. Similarly, such methods can be used to shrink the region of the ROI to generate an inner tumoral ROI.

In some cases, the set of prognostic parameters corresponds to inputs into a tissue classifier model in order to generate model output(s) (e.g., classification or label). In some embodiments, the set of prognostic parameters comprises a plurality of subsets of related feature groupings. In some embodiments, the set of prognostic parameters comprises a user-assigned classification of a region of interest. The user-assigned classification can be a mass boundary score.

A set of prognostic parameters can comprise parameters extracted from an image e.g. a corrected attenuation image, a compounded enhanced reflection image, an enhanced reflection image, or a sound speed image. In some embodiments, a set of prognostic parameters can comprise a description of a mass boundary score, a morphological feature, etc.

A set of prognostic parameters can comprise a parameter of a corrected attenuation image or data set. Such a parameter can be of an ROI, of a tumor or of a peri-tumor. Sometimes, a difference in such a value between a tumor and a peri-tumor can be in a set of prognostic parameters.

In some cases, a set of prognostic parameters of a corrected attenuation image or data set can comprise an average value within a tumor a kurtosis value within a tumor, a difference between a kurtosis values within a tumor and a kurtosis value within a peri-tumor, a standard deviation of a grayscale within a tumor, a gradient of a grayscale image within a tumor, a standard deviation of a gradient within a peri-tumor, a skewness of a gradient within a peri-tumor, a kurtosis of a corrected attenuation within a peri-tumor, a corrected attenuation of an energy within a tumor, a contrast of a grayscale of an image within a peri-tumor, a homogeneity of a grayscale of an image within a peri-tumor, or a difference in contrast of a grayscale within a tumor and within a peri-tumor.

A set of prognostic parameters can include a parameter of a compounded enhanced reflection image or data set. Such a parameter can be of a ROI, of a tumor or of a peri-tumor. Sometimes, a difference in such a value between a tumor and a peri-tumor can be in a set of prognostic parameters.

In some cases, a set of prognostic parameters of a compounded enhanced reflection image or data set can comprise an average grayscale value within a tumor, a kurtosis of a gradient within a tumor, a kurtosis of a gradient within a peri-tumor, a difference between a standard deviation of a gradient within a tumor and a standard deviation of a gradient within a peri-tumor, a homogeneity of an eroded grayscale image within a tumor, an energy of an eroded grayscale image within a peri-tumor, a homogeneity of an eroded grayscale image within a peri-tumor, a gradient of an energy of a grayscale image within a tumor, a correlation of a gradient of a grayscale image within a peri-tumor, a homogeneity of a gradient of a grayscale image within a peri-tumor, a difference between a contrast of a gradient of a grayscale image within a tumor and within a peri-tumor, or a difference between a correlation of grayscale images within a tumor and within a peri-tumor.

A set of prognostic parameters can include a parameter of an enhanced reflection image or data set. Such a parameter can be of a ROI, of a tumor or of a peri-tumor. Sometimes, a difference in such a value between a tumor and a peri-tumor can be in a set of prognostic parameters.

In some cases, the set of prognostic parameters of an enhanced reflection image or data set can comprise a skewness within a tumor, an average grayscale value within a tumor, a skewness within a peri-tumor, a difference between a standard deviation of a gradient within a tumor and a standard deviation of a gradient within a peri-tumor, a difference between kurtosis within a tumor and a kurtosis within a peri-tumor, an average of a gradient within a tumor, a standard deviation of a gradient within a peri-tumor, a skewness of a gradient within a peri-tumor, a kurtosis of a gradient within a peri-tumor, or a homogeneity of an eroded grayscale image within a peri-tumor.

A set of prognostic parameters can include a parameter of a sound speed image or data set. Such a parameter can be of an ROI, of a tumor or of a peri-tumor. Sometimes, a difference in such a value between a tumor and a peri-tumor can be in a set of prognostic parameters.

In some cases, a set of prognostic parameters can include a standard deviation of an eroded grayscale image within a tumor, an average of an eroded grayscale image within a tumor, a standard deviation of an eroded grayscale image within a peri-tumor, a first order entropy of a gradient within a tumor, a first order mean of a gradient within a tumor, a difference between a first order entropy within a tumor and a first order entropy within a peri-tumor, a contrast within a tumor, a correlation within a tumor, a difference in contrast between a tumor and a peri-tumor, or a difference in homogeneity between a tumor and a peri-tumor.

A set of prognostic parameters can comprise one or more of an irregularity of a margin, an average of sound speed values within a tumor, an average attenuation value within a peri-tumor, a contrast texture property of reflection within a peri-tumor, a difference between an average reflection value within a tumor and an average reflection value within a peri-tumor, a contrast texture property of a reflection within a tumor, a first order standard deviation of a sound speed value within a tumor, an average of a reflection value within a tumor, an average of a reflection value within a peri-tumor, a first order average of a reflection value within tumor, a difference between a homogeneity texture property of a reflection within a tumor and within a peri-tumor, a first order average of a sound speed value within a peri-tumor difference between a contrast texture property of an attenuation within a tumor and a contrast texture property of an attenuation within a peri-tumor, a standard deviation of a wavelet detail coefficient of a sound speed margin, a standard deviation of a wavelet detail coefficient of a reflection margin, a histogram of entropy of a wavelet detail coefficient of a reflection margin, a local minimum standard deviation of a wavelet detail coefficient of reflection margin, or a maximum of a standard deviation of a crisp contrast. A set of prognostic parameters can include at least 1, 2, 3, 4, 5, 6, 7, 8, 9, 10, 11, 12, 13, 14, 15, 16, 17, or 18 of these parameters. In some cases, the set of prognostic parameters can comprise other prognostic parameters.

In some embodiments, a set of prognostic parameters can comprise one or a plurality of sound propagation metrics characterizing sound propagation within a tissue. In some embodiments, a sound propagation metric(s) characterizes sound propagation interior to a region of interest, and/or exterior to a region of interest. In some cases, the sound propagation metric(s) characterizes at least one of sound speed, sound attenuation, and sound reflection. In some cases, the sound propagation metric(s) comprises one or more of: a sound speed metric, a reflection metric, an attenuation metric, a user defined score, a morphological metric, and a texture metric.

At a step 250 of the method 200, a plurality of prognostic parameters corresponding to sound propagation are generated from the acoustic rendering. At a step 260 of the method 200, a subset of the plurality of prognostic parameters corresponding to a predictive set of parameters may be generated from the acoustic rendering. Each layer, subset of layers, classification of layers, and/or ROI may have one or many associated quantitative prognostic parameters. Quantitative prognostic parameters may comprise, for example, a mean, a median, a mode, a standard deviation, and volume-averages thereof of any acoustic data type. A quantitative prognostic parameter may be calculated from a combination of data types. For example, a quantitative prognostic parameter may comprise a difference of prognostic parameters between a region in the interior of the ROI and in the exterior of the ROI. In another example, a quantitative prognostic parameter may comprise a difference between regions of interest, layers, classification of layers, etc. A quantitative prognostic parameter may comprise a ratio of a prognostic parameter with, for example, another prognostic parameter, a known biological property, etc. Additionally or alternatively, a quantitative prognostic parameter may be weighted by a spatial distribution. Additionally or alternatively, a quantitative prognostic parameter may be calculated from a volume average of an acoustic data type over, for example, a region of interest, a layer, a plurality of layers, a classification of layers, etc.

Each layer, classification of layers, and/or ROI may have one or many associated qualitative prognostic parameters. One or more qualitative prognostic parameters may be used in combination to generate other qualitative prognostic parameters. Qualitative prognostic parameters may comprise one or a combination of the shape, the sharpness, the architecture and/or other characteristics of the morphology renderings. The qualitative prognostic parameters may characterize any suitable aspect of the biomechanical property renderings. A qualitative prognostic parameter may be converted by a user or a computer into a semi-quantitative prognostic parameter, such as "1" for an indistinct margin and "2" for a sharp margin of the region of interest in the acoustic reflection rendering. As another example, a qualitative prognostic parameter may be converted by a user or a computer to a semi-quantitative parameter such as a value on an integer scale (e.g., 1 to 5) that classifies the degree to which the qualitative aspect is expressed. For instance, margin sharpness of the region of interest in the acoustic reflection rendering may be classified with a reflection index as "1" if it is very sharp, "3" if it is moderately indistinct, or "5" if it is very indistinct.

Qualitative, quantitative, and semi-quantitative prognostic parameters may be combined in order to generate other extended prognostic parameters. These extended prognostic parameters may comprise the existing Breast Imaging Reporting and Data System (BI-RADS), wherein a lesion is characterized on an integer scale from 1 to 5, but may also comprise other extended prognostic parameters comprising acoustic data. The prognostic parameters disclosed herein may be time dependent. The time dependence of one or a plurality of prognostic parameters may comprise a prognostic parameter. Although all of these quantitative and qualitative prognostic parameters may be determined, only a portion of these parameters may be determined.

Table 1 shows example fields for organizing prognostic parameters by region of interest and by classification of region of interest, including fields for the mean (e.g., the volume-average) and standard deviation (e.g., the volume-standard-deviation) of a particular acoustic data types A, B, and C over a volume of tissue. The table also comprises prognostic parameters associated with differences between classifications of layers associated with a region of interest.

| Region | | A | B | C |
|---|---|---|---|---|
| Tumor (T) | Mean | | | |
| | Std. Dev. | | | |
| Peritumoral (P) | Mean | | | |
| | Std. Dev. | | | |

-continued

| Region | A | B | C |
| --- | --- | --- | --- |
| Near peritumoral (nP) | Mean | | |
| | Std. Dev. | | |
| Distant peritumoral (dP) | Mean | | |
| | Std. Dev. | | |
| Relative Peri (T-P) | Mean | | |
| | Std. Dev | | |
| RelNearP (T-nP) | Mean | | |
| | Std. Dev | | |
| Rel DistanP (T-dP) | Mean | | |
| | Std. Dev | | |

The region "tumor" characterizes a set of prognostic parameters associated with acoustic data interior to a region of interest. The region "peritumoral" characterizes a set of prognostic parameters associated with acoustic data exterior to a region of interest. The region "near peritumoral" characterizes a set of prognostic parameters associated with a classification of layers which may be near to the margin boundary of the region of interest and may be exterior to the region of interest. The region "distant peritumoral" characterizes a set of prognostic parameters associated with a classification of layers which may be distant to the margin boundary of the region of interest and may be exterior to the region of interest. The region "Relative Peri" characterizes a set of prognostic parameters associated with the difference between a set of interior prognostic parameters less a set of exterior prognostic parameters. The region "RelNearP" characterizes a set of prognostic parameters associated with the difference between a set of interior prognostic parameters less a set of prognostic parameters which may be associated with a classification of layers, which may be near to the margin boundary of the region of interest and may be exterior to the region of interest. The region "RelDistanP" characterizes a set of prognostic parameters associated with the difference between a set of interior prognostic parameters less a set of prognostic parameters which may be associated with a classification of layers, which may be distant to the margin boundary of the region of interest and may be exterior to the region of interest.

Table 1 also shows example fields for organizing prognostic parameters by various acoustic data types. In some embodiments, individual prognostic parameters may correspond to a statistical metric, such as mean or a standard-deviation, over a volume, such as defined by a region, a layer, or a classification of layers. Such data type may include but are not limited to, for example, the margin boundary score, the mean enhanced reflection (ErfMean), the relative mean of the enhanced reflection interior and exterior to the ROI (ErfRelDist), the standard deviation of the enhanced reflection (Erf_SD), the mean sound speed (SSMean), the relative mean sound speed interior and exterior to the ROI (SSRelDist), the standard deviation of the sound speed (SS_SD), the mean attenuation (AtMean), the standard deviation of the attenuation (At_SD), the mean of the attenuation corrected for the margin boundary score (Corr_At_Mean), and the standard deviation of the attenuation corrected for the margin boundary score (Corr_At_SD).

In some embodiments, the set of prognostic parameters comprises at least one morphological metric of the region of interest. In some embodiments, the morphological metric comprises at least one of a roundness, an irregularity of a shape, an irregularity of a margin, and a smoothness of a margin.

In some cases, a ROI can be described by the propagation of sound within the ROI. Such a description can be in the form of a sound propagation metric. Such a metric can characterize sound propagation within a ROI, such as within a tumor or within a peri-tumor. In some cases, such a metric can characterize sound propagation exterior to an ROI. In some cases, a second sound propagation metric can characterize sound propagation interior or exterior to a ROI. Such a sound propagation metric can comprise an average, a standard deviation, a skewness, or a kurtosis. In some cases, the difference between two sound propagation metrics can be a prognostic parameter.

A prognostic parameter can comprise an average value or derive from a calculation of an average. An average value can be calculated as e.g. a mean, median, or mode. An average value can be determined for a corrected attenuation image, an enhanced reflection image, a compounded enhanced reflection image, or a sound speed image.

A prognostic parameter can comprise a kurtosis value. A kurtosis value can describe or represent the sharpness of a peak of a frequency-distribution curve. In some cases, kurtosis can be calculated as a kurtosis of a gradient of an image such as a grayscale image. Kurtosis can be determined for a corrected attenuation image, an enhanced reflection image, a compounded enhanced reflection image, or a sound speed image.

A prognostic parameter can comprise a standard deviation. In some cases, a standard deviation can be determined as a standard deviation of a gradient of an image, such as a grayscale image. A standard deviation can be determined for a corrected attenuation image, an enhanced reflection image, a compounded enhanced reflection image, or a sound speed image.

In some embodiments, a sound propagation metric can characterize at least one of sound speed, sound attenuation, and sound reflection. For example, a sound propagation metric can comprise a sound speed metric and a sound attenuation metric, a sound speed metric and a sound reflection metric, or a sound attenuation metric and a sound reflection metric. In some cases, a sound propagation metric can comprise a sound speed metric, a sound attenuation metric, and a sound reflection metric.

In some embodiments, a user defined score can be included in the sound propagation metric. In other words, a sound propagation metric can comprise a user defined score as well as a sound speed metric, a sound attenuation metric, or sound propagation metric. For example, a sound propagation metric can comprise a sound speed metric, a sound attenuation metric, and a user defined score. As another example, a sound propagation metric can comprise a sound speed metric, a sound reflection metric, and a user defined score. As another example, a sound propagation metric can comprise a sound attenuation metric and a user defined score. As a further example, a sound propagation metric can comprise a sound attenuation metric, a sound speed metric, a sound propagation metric, and a user defined score.

In some embodiments, a morphological metric can be included in the sound propagation metric. In other words, a sound propagation metric can comprise a morphological metric as well as a sound speed metric, a sound attenuation metric, or sound propagation metric. For example, a sound propagation metric can comprise a sound speed metric, a sound attenuation metric, and a morphological metric. As another example, a sound propagation metric can comprise a sound speed metric, a sound reflection metric, and a morphological metric. As another example, a sound propagation metric can comprise a sound attenuation metric and a morphological metric. As a further example, a sound propagation metric can comprise a sound attenuation metric, a sound speed metric, a sound propagation metric, and a morphological metric.

A prognostic parameter can comprise a contrast. A contrast can be a measure of a difference in signal within a ROI such as a tumor or a peri-tumor.

A prognostic parameter can comprise a homogeneity value. A homogeneity value can be a measure of variation within a ROI such as a tumor or a peri-tumor.

In some embodiments, a set of prognostic parameters comprises at least one texture metric of a ROI. A texture metric can comprise at least one of an edgeness, a grey level co-occurrence matrix, and a Law's texture map.

In some cases, a prognostic parameter can be a parameter of a wavelet of an image. In some cases, a wavelet of an image can represent an image. In some cases, a wavelet can be employed in the analysis of an image. Examples of wavelets can include a continuous wavelet transform of an image or a discrete wavelet transform of an image.

In some embodiments, the features herein may include 10 main classes including: mass boundary score (MBS, morphological features, quantitative features, quantitative features of gradient image(s), first order statistics of normal gray scale, first order statistics of eroded gray scale, first order statistics of gradient gray scale, gray level co-occurrence matrices (GLCM) second order features of normal gray scale, GLCM second order features of eroded gray scale, and GLCM second order features of gradient gray scale. For example, the feature(s) of first order statistics of normal gray scale includes mapping of quantitative values in tumor and peritumoral region to gray scale values defined by min/max of quantitative values in the union of the tumor and peritumoral regions, so that quantitative values are normalized. As another example, the feature(s) of first order statistics of normal gray scale includes mean, standard deviation, skewness, histogram, etc for tumor, peritumoral, or both regions. Yet another examples, the feature(s) of first order statistics of eroded gray scale includes mapping of quantitative values in tumor and peritumoral region to gray scale values defined by min/max of quantitative values in eroded masks of the tumor and peritumoral regions with an erosion radius of 0.66*tumor radius.

In some embodiments, the features extracted from ROIs are order statistics (i.e. mean, variance, skewness, kurtosis, contrast, noise level, signal to noise ratio (SNR), etc.) of the underlying acoustic parameters (the raw pixel value of each image) or the gray/color scale counter parts. In some cases, the texture of the images can be assessed by using order statistics of histograms characterizing the value of gray scale distributions. In some embodiments, features herein include texture features such as first order histogram features. In some embodiments, the features include higher order features which further characterize texture such as gray level co-occurrence matrices (GLCM) and their respective scalar features (energy, entropy, etc.) In some embodiments, the co-occurrence matrix herein is method which compares the intensity of a pixel with its local neighborhood. In some embodiments, the co-occurrence matrix can examine the number of times a particular value (in grey scale) co-occurs with another in some defined spatial relationship. For example, if we loop over every pixel with the tumor ROI, we can ask how many times that pixel's value is a gray scale of 5 and the pixel adjacent to the right of that pixel has a gray scale value of 9. After constructing the co-occurrence matrix, scalar features can be constructed. This includes the energy, entropy, contrast, homogeneity, and correlation.

Definitions for these scalar features can be found, for example, in the following reference, https//www.code.ucs-d.edu/pcosman/glcm.pdf. In some embodiments, the features include higher order features such as Law's Texture Maps, features associated with Wavelet or Fourier analysis, or fractal analysis. In some embodiments, the features herein include texture features. In some embodiments, the edgeness within an image 1 is defined as the number of pixels within the ROI R that are above some threshold E within the image as $$\text{Edgeness} = \sum_{j \in R: I[j] > \epsilon} \frac{1}{N_R} I[j]$$

In some embodiments, the features herein include Law's Texture Energy Measure which relies on applying various local filters to the image. These filters may include but are not limited to an averaging filter, an edge detection filter, a ripple detection filter, and a spot detection filter. The resulting images are then linear combined in various ways to produce a set of nine texture images.

In some embodiments, the features include morphological features that characterize the morphology of the ROIs described above (roundness, irregularity, etc.). In some embodiments, a morphological feature, smoothness of the margin may be determined as the ratio between the areas of the mass to the area of the smallest convex hull containing the segmented mass. the ratio of the tumor area (area defined by the inner light grey contour) and the outer darker grey convex hull area can be the smoothness of margin.

In some embodiments, roundness of the shape may be determined as $$\frac{(\text{maximum length})^2}{\text{area}} \times \frac{\text{pi}}{4}$$

In some embodiments, irregularity of the shape may be determined as $$\frac{(\text{perimeter})^2}{\text{area}} \times \frac{1}{4\pi}$$

In some embodiments, irregularity of the margin may be determined as $$1 - \frac{\text{diameter}' \times \pi}{\text{perimeter}}$$

wherein diameter' is the diameter of a circle with the same area as ROI as $$\sqrt{\frac{4 \times \text{area}}{\pi}}$$

An example of Law's texture maps are seen in FIG. 5. FIG. 5A shows a sound speed image, and FIG. 5B shows an EE (EdgeEdge) map of FIG. 5A; FIG. 5C shows an ESSE map of FIG. 5A, and FIG. 5D shows an ESSE (EdgeSpotSpotEdge) map with 4-bit color.

In some embodiments, the features herein can include fuzziness. Fuzziness can quantify boundary features, e.g., boundary features of a lesion.

In some embodiments, fuzziness can be determined by a method which can comprise flagging margins, such as margins of a lesion.

Once margins are flagged, a wavelet transform can be applied to yield a 2-dimensional wavelet. Polar coordinates can be used for the visualization of a 2-dimensional wavelet image. In some cases, the 2-dimensional wavelet image can be normalized.

A wavelet transform can be applied to the 2-dimensional wavelet image to yield a 1-dimensional wavelet. The 1-dimensional wavelet can be displayed using polar coordinates.

Fuzziness features can comprise a mean, a maximum, a difference between a maximum and a minimum, a standard deviation, or an entropy (e.g. local entropy or whole entropy).

Fuzziness features can be extracted from the 1-dimensional wavelet. Examples of fuzziness features can comprise a wavelet detail of a reflection margin or a sound speed margin. In some cases, a wavelet detail of a sound speed margin can comprise a horizontal detail, a vertical detail, or a diagonal detail. In some cases, a wavelet detail of a reflection margin can comprise a horizontal detail, a vertical detail, or a diagonal detail. In some cases, fuzziness features can comprise an approximation coefficient of a sound speed margin or an approximation coefficient of a reflection margin.

Figure 6:
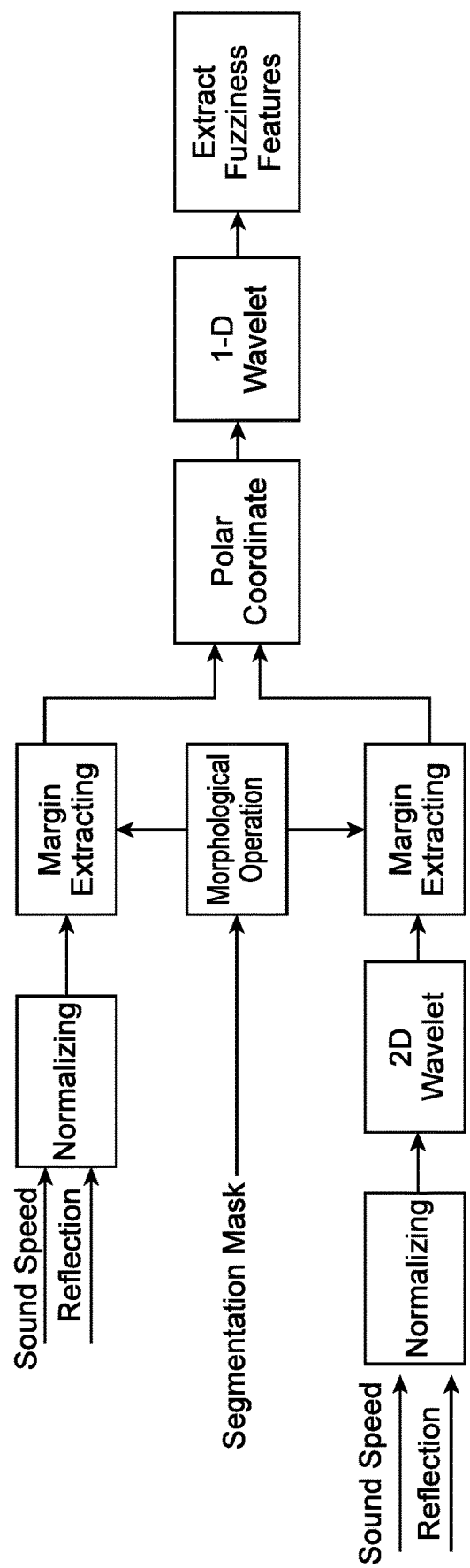
FIG. 6 illustrates an example method for determining fuzziness, in accordance with some embodiments.

In some cases, fuzziness can be determined using a method as shown in FIG. 6. A sound speed image and a reflection image can be used as an input. A segmentation mask (for example, as achieved via segmentation or auto-segmentation) can be also used as an input. The sound speed image and reflection image can be transformed to a 2-dimensional wavelet. Margins can be extracted from the 2-dimensional wavelet of the sound speed image, the 2-dimensional wavelet of the reflection image, the original sound speed image, and the original reflection image. In some cases, the segmentation mask can be sued to perform morphological operations on the images and 2-dimensional wavelets for the margin extraction. Once the margins are extracted, the images and wavelets can be converted to polar coordinates, and transformed to a 1-dimensional wavelet. Fuzziness features can be extracted from the 1-dimensional wavelet.

Figure 7A:
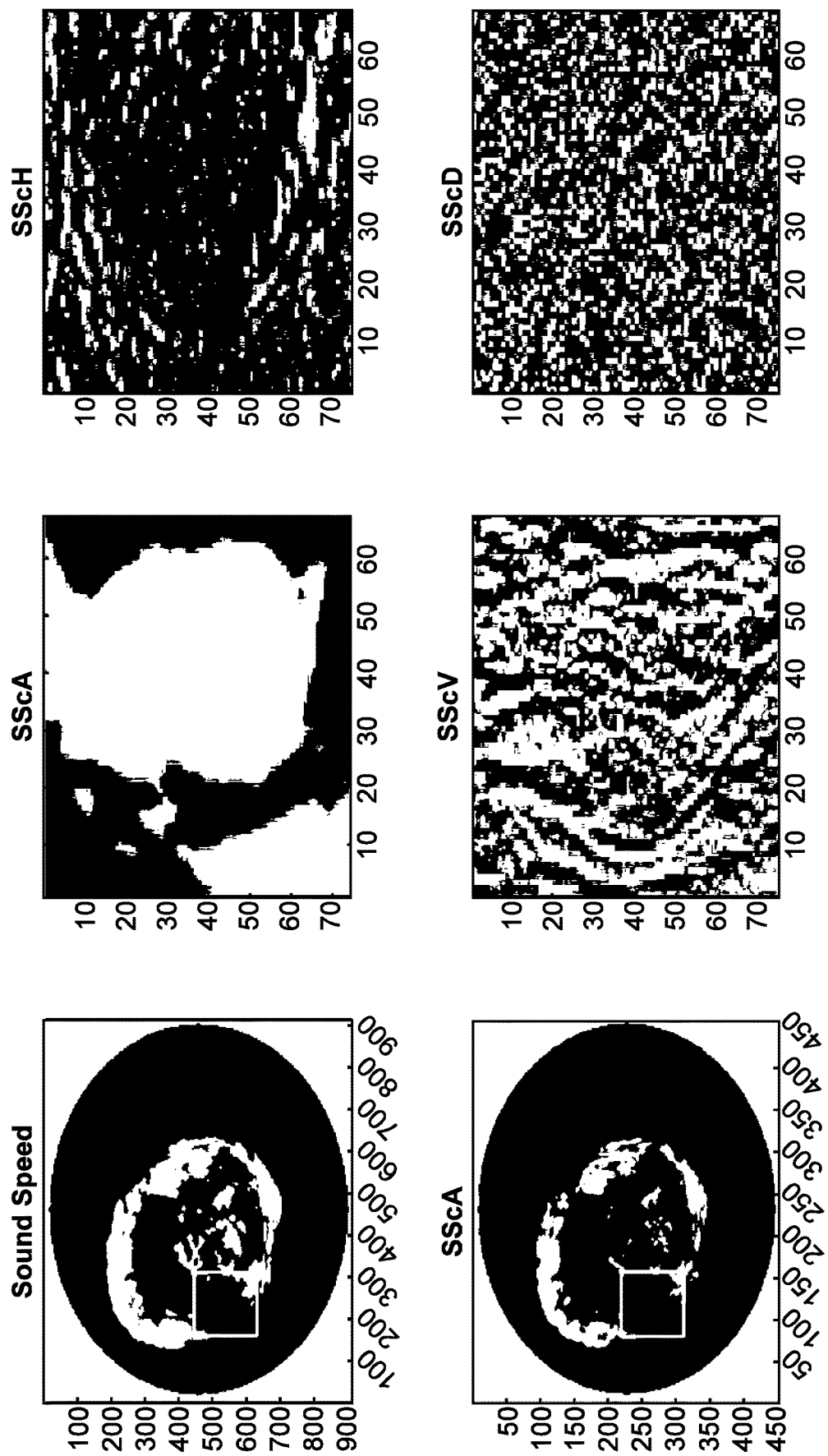
FIG. 7A illustrates an example of a sound speed image and corresponding 2-dimensional wavelets, in accordance with some embodiments.
Figure 7B:
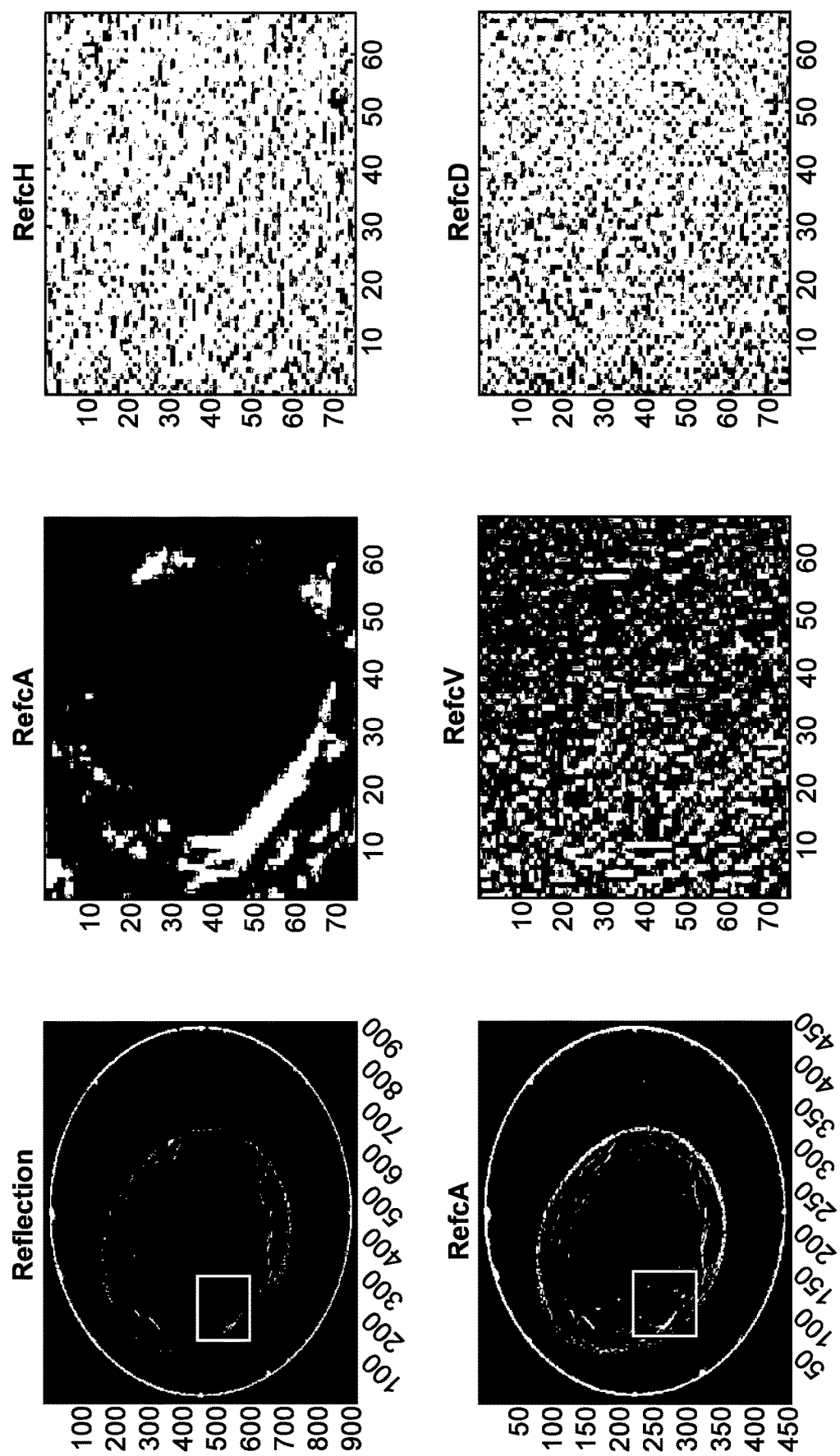
FIG. 7B illustrates an example of a reflection image and corresponding 2-dimensional wavelets, in accordance with some embodiments.

FIG. 7A shows an example of a sound speed images and corresponding 2-dimensional wavelets. FIG. 7B shows examples of reflection images and corresponding 2-dimensional wavelets. In these figures, the top left panel represents the original image, the bottom right panel represents the normalized image, the top middle panel depicts the cA wavelet of the sound speed image, the bottom middle panel represents the cV wavelet of the sound speed image, the top right panel represents cH wavelet of the sound speed image, and the bottom left panel represents the cD wavelet of the sound speed image.

Figure 8:
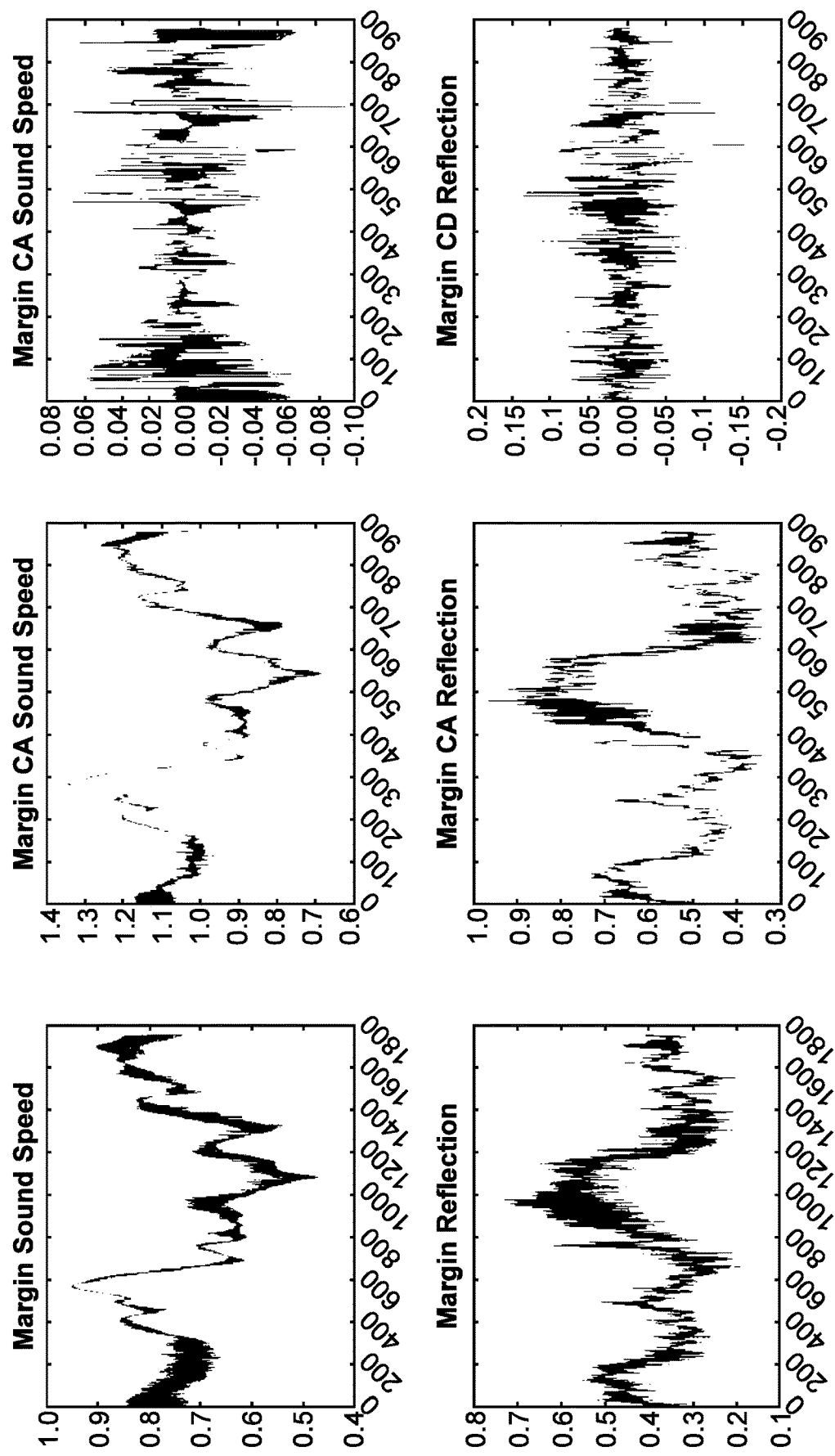
FIG. 8 illustrates wavelets of sound speed images and reflection images, in accordance with some embodiments.

1-dimensional wavelets were determined for the sound speed and reflection images, and are shown in FIG. 8. Wavelets are shown for sound speed images (top) and reflection images (bottom). Wavelets of margin (left), cA wavelet near the margin (middle), and cD wavelet near the margin (right) are shown.

Figure 9A:
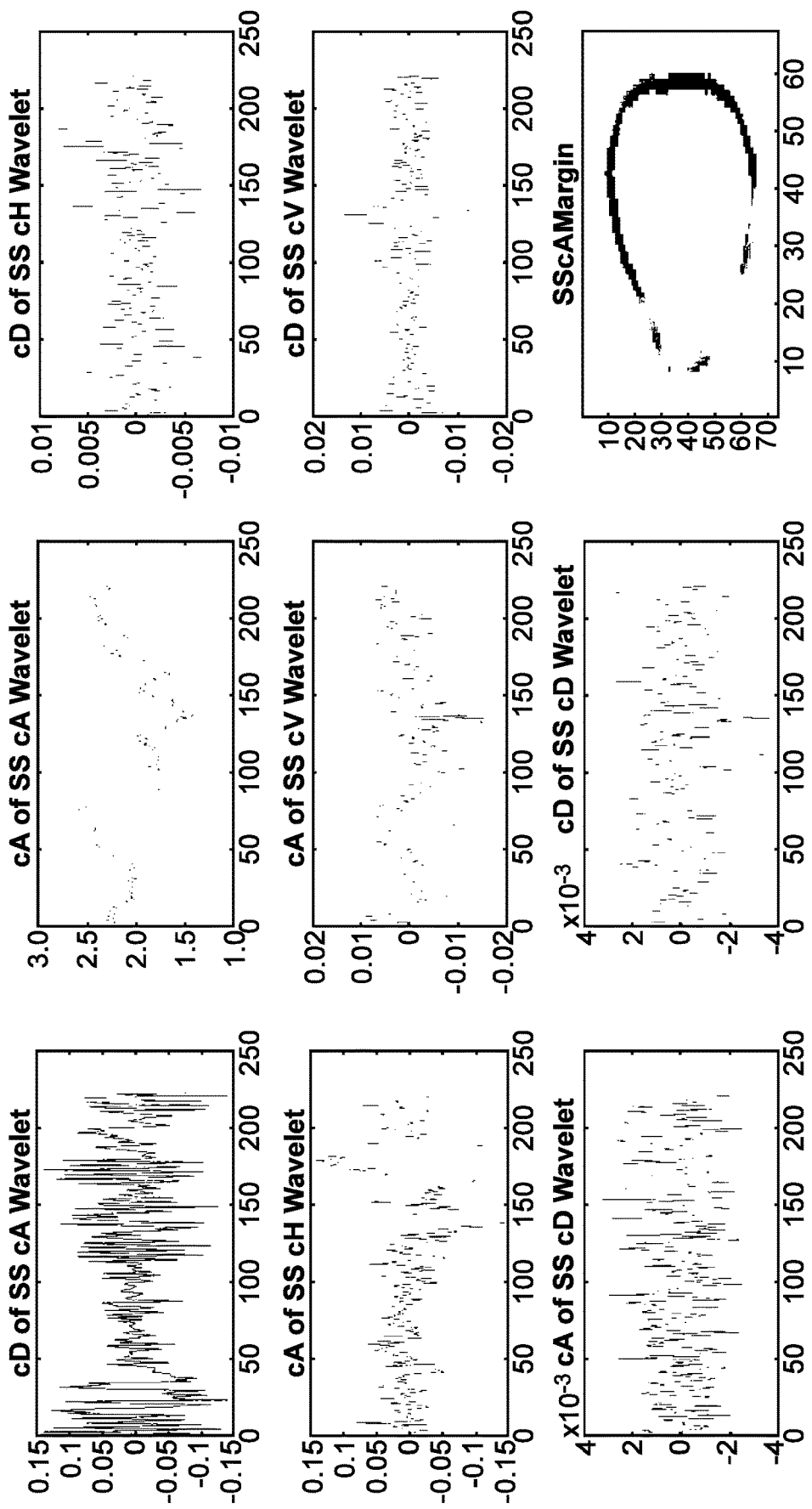
FIG. 9A illustrates 1-dimensional wavelet margins from sound speed wavelet images, in accordance with some embodiments.

1-dimensional wavelet margins from sound speed wavelet images are shown in FIG. 9A. The top right panel depicts the cD of the sound speed cA wavelet, the top middle panel depicts the cA of the sound speed cA wavelet, the top left panel depicts the cD of the sound speed cH wavelet, the middle left panel depicts the cA of the sound speed cH wavelet, the middle panel depicts the cA of the sound speed cV wavelet, the middle right panel depicts the cD of the sound speed cV wavelet, the bottom left panel depicts the cA of the sound speed cD wavelet, the bottom middle panel depicts the cD of the sound speed cD wavelet, and the bottom right panel depicts the sound speed cA margin.

Figure 9B:
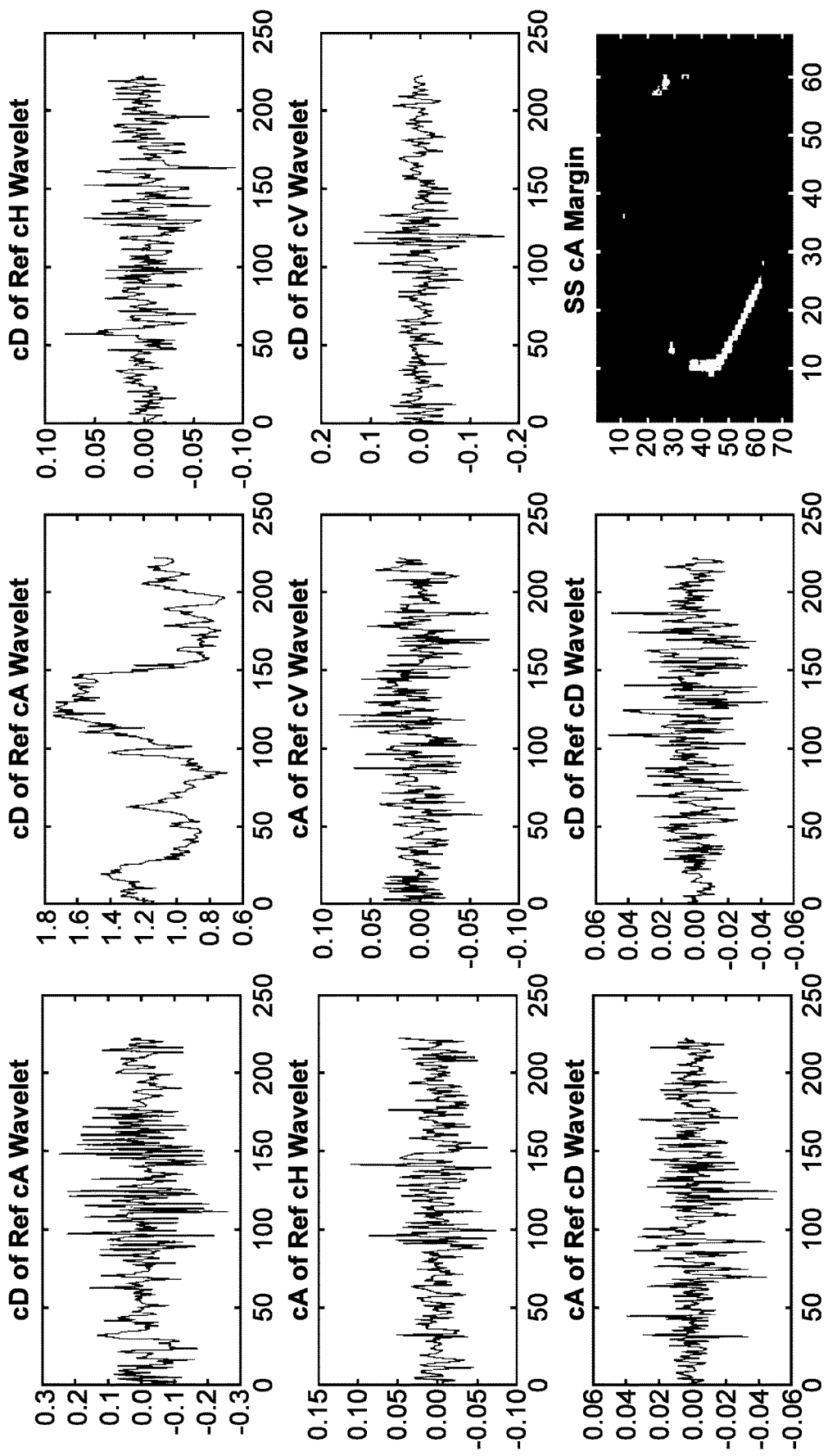
FIG. 9B illustrates 1-dimensional wavelet margins from reflection wavelet images, in accordance with some embodiments.

1-dimensional wavelet margins from reflection wavelet images are shown in FIG. 9B. The top right panel depicts the cD of the sound speed cA wavelet, the top middle panel depicts the cA of the sound speed cA wavelet, the top left panel depicts the cD of the sound speed cH wavelet, the middle left panel depicts the cA of the sound speed cH wavelet, the middle panel depicts the cA of the sound speed cV wavelet, the middle right panel depicts the cD of the sound speed cV wavelet, the bottom left panel depicts the cA of the sound speed cD wavelet, the bottom middle panel depicts the cD of the sound speed cD wavelet, and the bottom right panel depicts the sound speed cA margin.

Including fuzziness as a feature (e.g., in combination with other features used for classification) can improve the area under the curve of a receiver operating characteristic curve, when compared with a result when the features do not include fuzziness. This can be done for lesions which have been manually segmented, auto-segmented, or ellipse-segmented. When fuzziness is included as a feature, the area under the curve can increase by about 0.01, 0.02, 0.03, 0.04, 0.05, 0.06, or 0.07. In some cases, when fuzziness is included as a feature, the area under the curve can increase by at least 0.05, at least 0.06, at least 0.07, at least 0.08, at least 0.09, at least 0.01, at least 0.02, at least 0.03, at least 0.04, or at least 0.05. In some cases, when fuzziness is included as a feature, the area under the curve can increase by at least 1%, at least 2%, at least 3%, at least 4%, at least 5%, at least 6%, or at least 7% compared to when fuzziness is not included.

An algorithm which includes fuzziness as a feature can have a sensitivity of at least 70%, at least 75%, at least 80%, at least 85%, at least 90%, or at least 95%. An algorithm which includes fuzziness as a feature can have a sensitivity of between 70% and 90%, between 80% and 90%, or between 70% and 80%. In some cases, an algorithm which includes fuzziness as a feature can have a specificity of at least 70%, at least 75%, at least 80%, at least 85%, at least 90%, or at least 95%. An algorithm which includes fuzziness as a feature can have a specificity of between 70% and 95%, between 80% and 95%, or between 80% and 95%.

In some embodiments, the features herein can include crispiness. Crispiness can quantify or describe the quickness of a change at a margin, e.g., a margin of a lesion. In some cases, crispiness can quantify the magnitude of a change at a margin.

Figure 10:
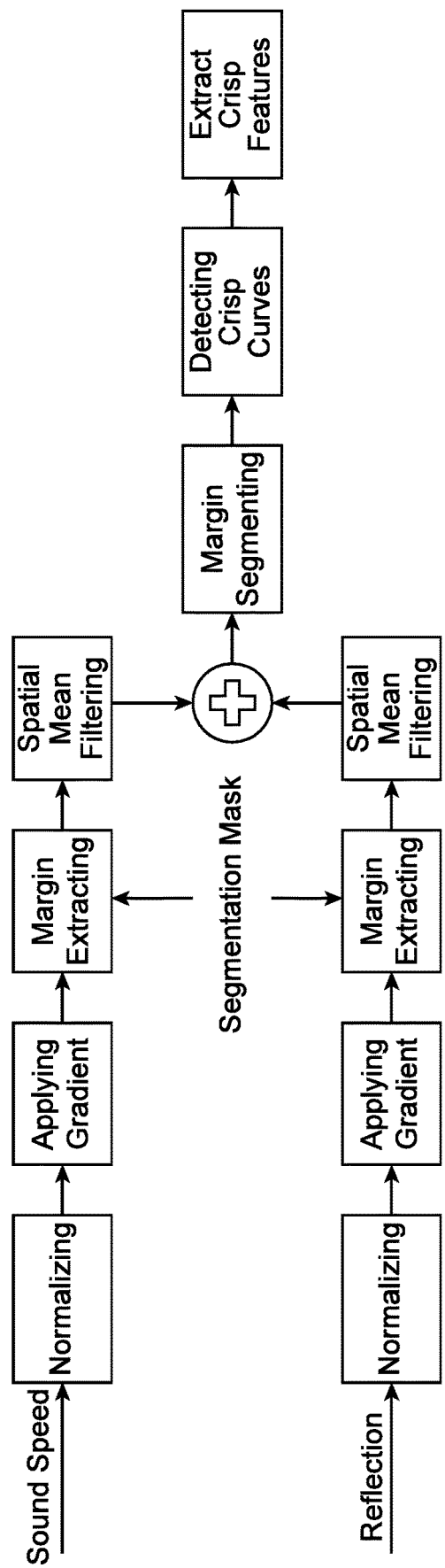
FIG. 10 illustrates an example method for extracting crispness features, in accordance with some embodiments.

A crispiness feature or features can be extracted as shown in FIG. 10. Crispiness can be determined using a sound speed image or for a reflection image. In some cases, crispiness can be determined using both a sound speed image and a reflection image.

If a sound speed image and a reflection image are used to determine crispiness, the first few steps can be similar or parallel for the sound speed and reflection images. First, each image can be normalized by an acceptable normalization method. A gradient can be applied to a normalized image.

After application of a gradient, margin extraction can be performed. For this step, a segmentation mask can be created to facilitate the margin extracting. For example, in some cases the margin extraction can be performed via dilating and eroding. Erosion can remove from the segmentation mask, to yield a mask comprising the margin of a lesion and perhaps not comprising other regions of a lesion. Dilation can add to a segmentation mask, for example to fill in holes or broken areas, or to connect areas separated by spaces. The margin extraction can yield a margin mask.

Figure 11:
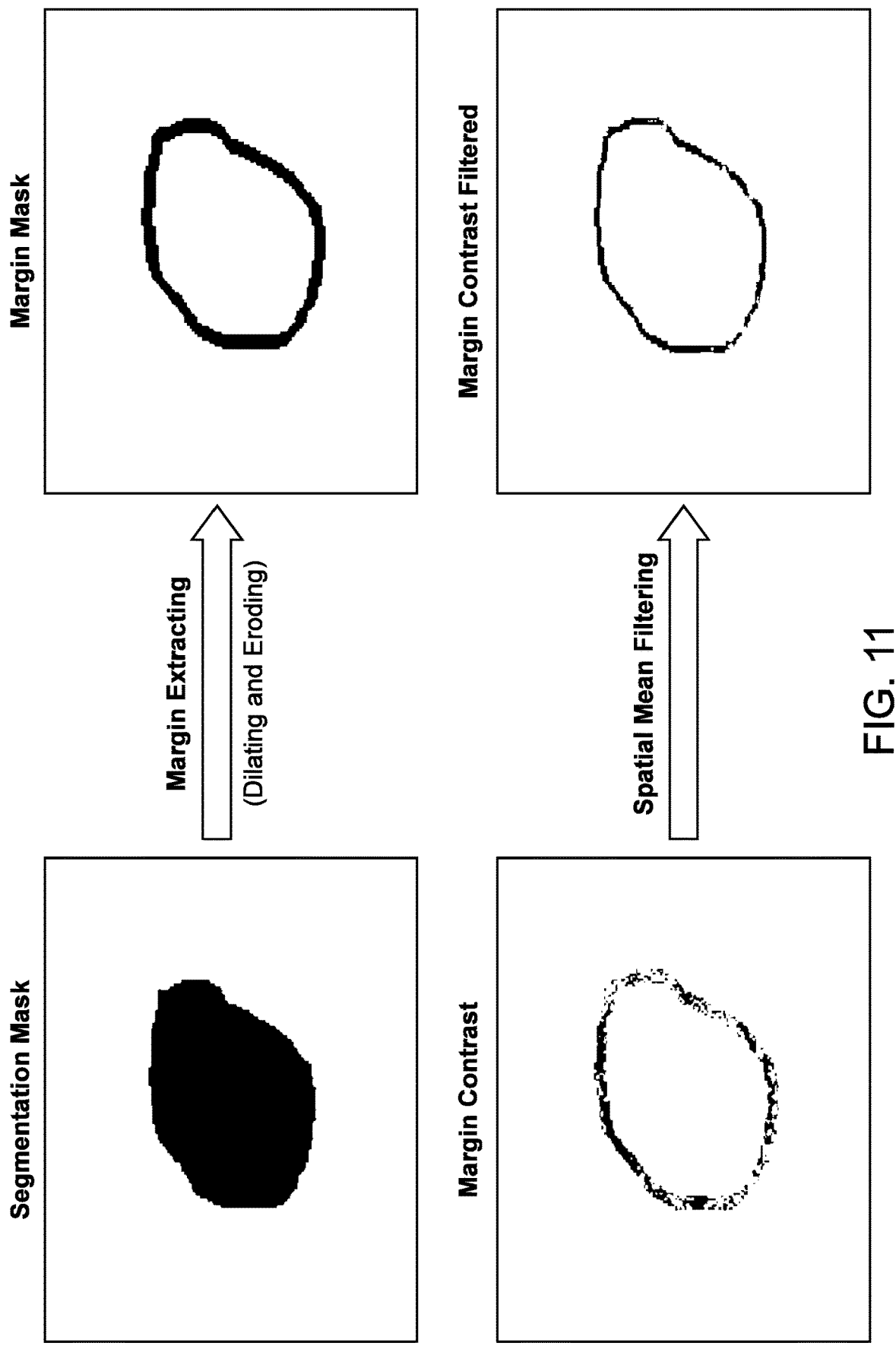
FIG. 11 illustrates an example of margin extraction and spatial mean filtering of a lesion, in accordance with some embodiments.

After margin extraction, spatial mean filtering can be performed. In some cases, this filtering can be performed on a contrast image which has been masked with a margin mask. In some embodiments, a filtered margin contrast image can be achieved. An example of margin extraction and spatial mean filtering of a lesion is shown in FIG. 11.

At this point, in some cases, the sound speed and reflection images can be summed. Margin segmentation can be performed, and one or more crisp curves can be detected. In some cases, detection of one or more crisp curves can define a crisp area. Crisp features can then be extracted.

Crisp features can comprise a mean, a maximum, a difference between a maximum and a minimum, or a variance. Features can be of a pixel value or of a value derived from a pixel value.

A standard deviation of a crisp contrast can be a good feature for discriminating a benign lesion from a malignant lesion. In some cases, including a maximum of a standard deviation of a crisp contrast can improve accuracy of a classification algorithm. In some cases, including a difference between a maximum and a minimum of a standard deviation of a crisp contrast can improve accuracy of a classification algorithm. In some cases, other features of a standard deviation of a crisp contrast can improve accuracy of a classification algorithm.

The slope of crisp margins might be a good feature for discriminating a benign lesion from a malignant lesion. For example, including a crisp angular feature, a skewness slope, or both can improve accuracy of a classification algorithm.

In some cases, crisp features can be a crisp contrast mean, a standard deviation of crisp contrast, contrast derivative (e.g., first derivative or second derivative) at a change point, crisp pixel radius, crisp angular, skewness of a crisp slope, or kurtosis of a crisp slope. Herein, a crisp slope can be the slope of a line fit to the crisp curve in polar coordinates.

In some cases a crisp feature can be a circumscribed feature. A circumscribed feature can be calculated for example using the crisp angular and the crisp pixel radius. In some cases, the variance of the crisp pixel radius can be used to calculate a circumscribed feature. In some cases, a circumscribed feature can be calculated as the ratio of a crisp angular to the variance of a crisp pixel radius.

Figure 12A:
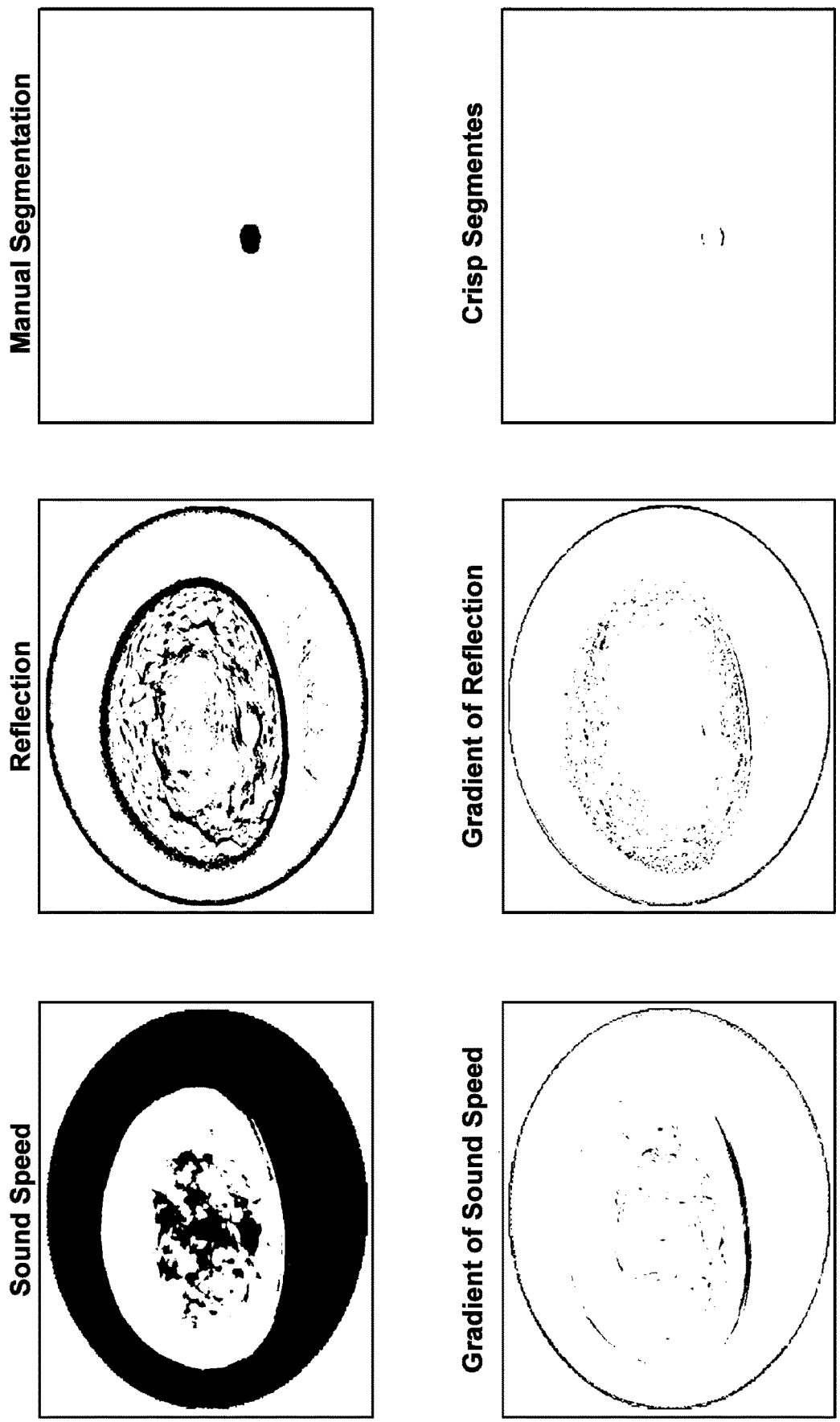
FIG. 12A illustrates the identification of crisp segments of sound and speed reflection images of a breast having a cyst, in accordance with some embodiments.

In FIG. 12A, sound speed and reflection images of a breast having a cyst were acquired, and the gradients of the images were achieved. Segmentation was performed to segment the cyst, and crisp segments were identified, as shown in the bottom right panel.

Figure 12B:
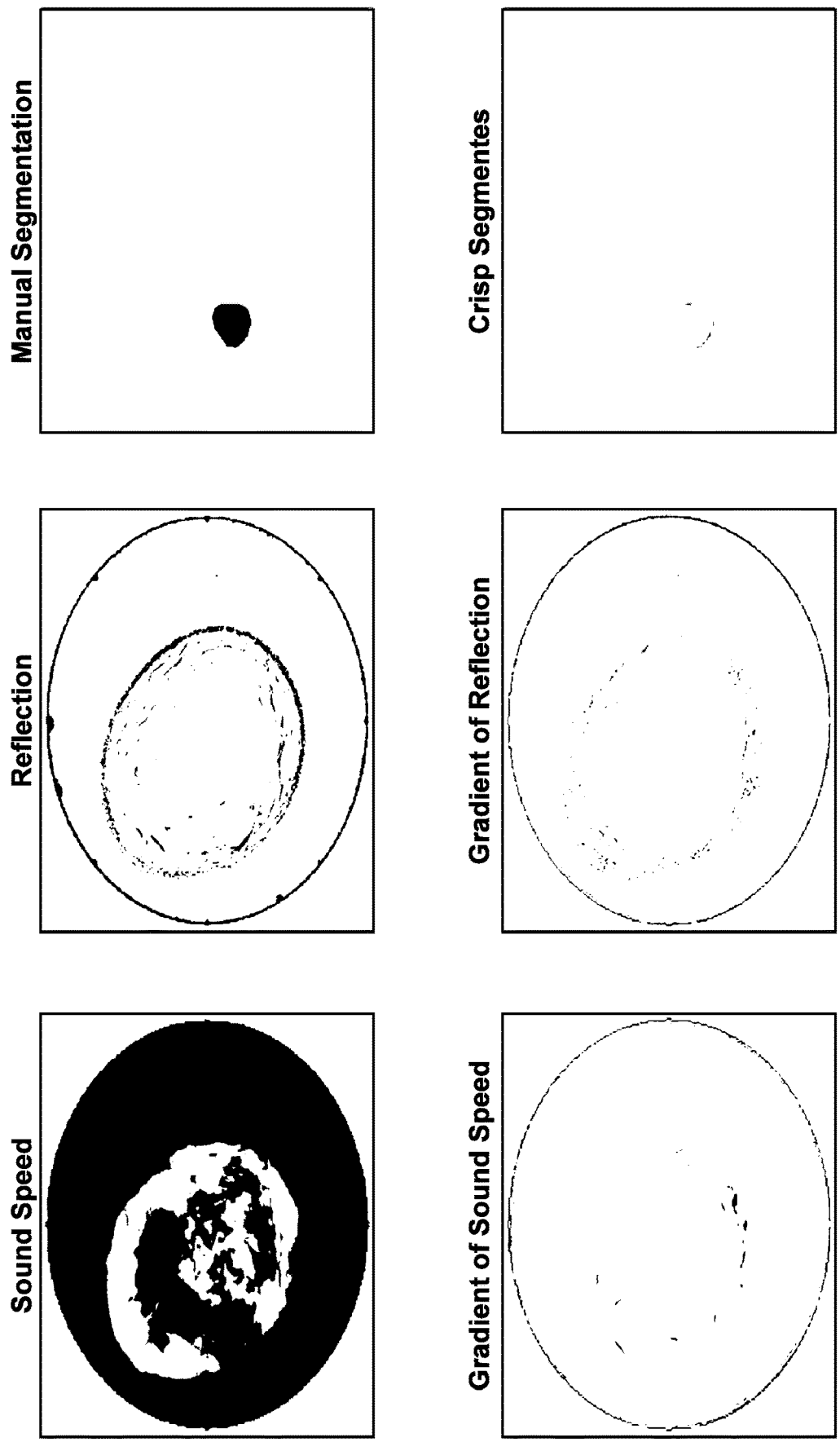
FIG. 12B illustrates the identification of crisp segments of sound and speed reflection images of a breast having a fibroadenoma, in accordance with some embodiments.

In FIG. 12B, sound speed and reflection images of a breast having a fibroadenoma were acquired, and the gradients of the images were achieved. Segmentation was performed to segment the fibroadenoma, and crisp segments were identified, as shown in the bottom right panel.

Figure 12C:
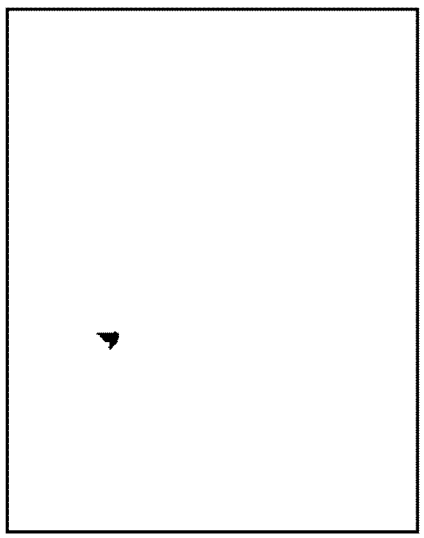
FIG. 12C illustrates the identification of crisp segments of sound and speed reflection images of a breast having a tumor, in accordance with some embodiments.
Figure 12C:
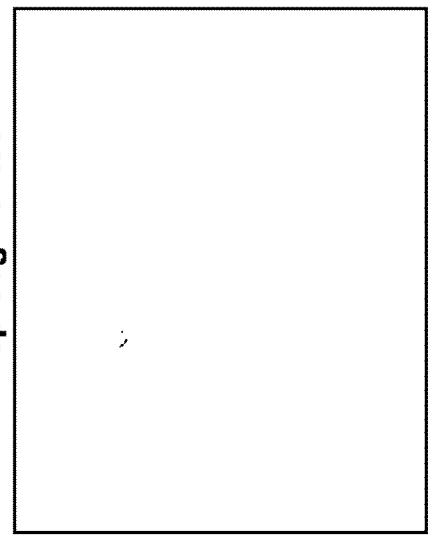
Figure 12C:
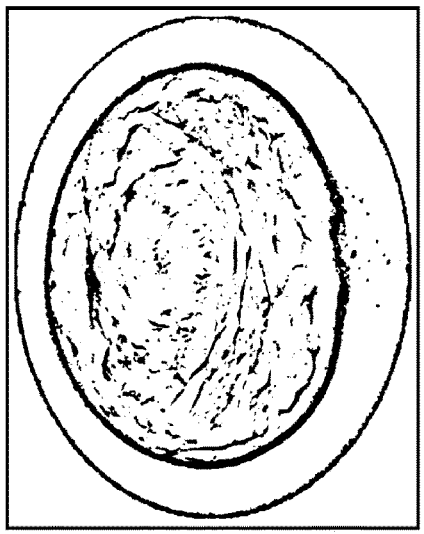
Figure 12C:
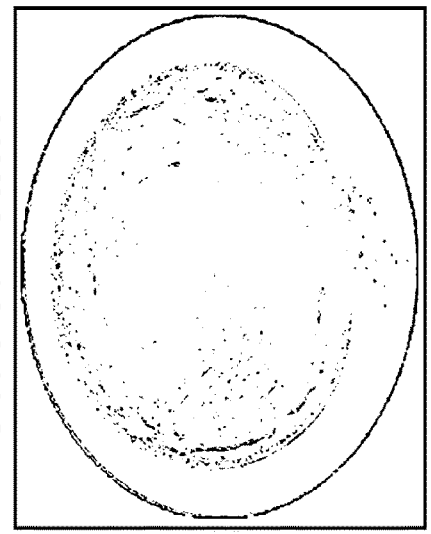
Figure 12C:
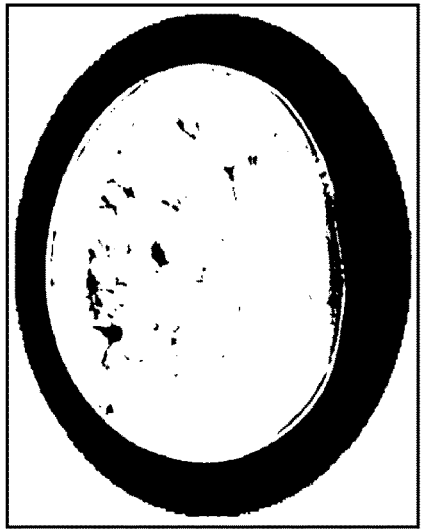
Figure 12C:
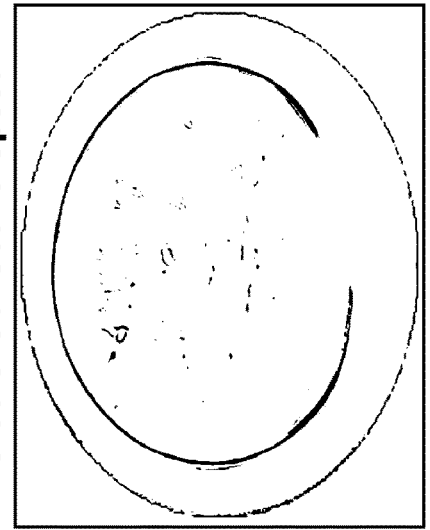

In FIG. 12C, sound speed and reflection images of a breast having a tumor were acquired, and the gradients of the images were achieved. Segmentation was performed to segment the tumor, and crisp segments were identified, as shown in the bottom right panel.

In some embodiments, the features used to characterize a lesion can comprise fuzziness and crispiness.

Including crispiness as a feature (e.g., in combination with other features used for classification) can improve the area under the curve of a receiver operating characteristic curve when compared with a result when the features do not include crispiness. This can be done for lesions which have been manually segmented, auto-segmented, or ellipse-segmented. When crispness is included as a feature, the area under the curve can increase by 0.01. In some cases, the area under the curve can increase by at least 0.05, at least 0.06, at least 0.07, at least 0.08, at least 0.09, or at least 0.01.

An algorithm which includes crispiness as a feature can have a sensitivity of at least 70%, at least 75%, at least 80%, at least 85%, at least 90%, or at least 95%. An algorithm which includes crispiness as a feature can have a sensitivity of between 70% and 90%, between 80% and 90%, or between 70% and 80%. In some cases, an algorithm which includes crispiness as a feature can have a specificity of at least 70%, at least 75%, at least 80%, at least 85%, at least 90%, or at least 95%. An algorithm which includes crispiness as a feature can have a specificity of between 70% and 95%, between 80% and 95%, or between 80% and 95%.

In some cases, crispiness and fuzziness features can both be used. Crispiness and fuzziness can be used in conjunction with other features, such as texture features, morphological features, or statistical features. Features including crispiness and fuzziness can be extracted, selected (e.g., by a machine learning algorithm), and used for the classification of a lesion.

A circularity feature can be added to a feature extraction algorithm comprising crispiness and fuzziness, and can improve the performance of algorithm. A circularity feature can be added by fitting an ellipse to a tumor and calculating how similar the mass is to the ellipse.

A feature extraction algorithm comprising crispiness and fuzziness can experience a change in a classifier which can improve the performance of the algorithm. Such a change can be e.g., from a neural network to a support vector machine. A change can be to another acceptable classifier, such that an optimal classifier is chosen.

For some algorithms, a circularity feature can be added and an optimal classifier can be chosen. Such algorithms can be called "enhanced algorithms."

An enhanced algorithm can yield an improvement over the same algorithm which has not been enhanced. In some cases, an algorithm can have an improvement in the area under the curve of the receiver operating characteristic curve by using such enhancement techniques. In some cases, an algorithm comprising crispiness and fuzziness can have an improvement in the area under the curve of the receiver operating characteristic curve by using such enhancement techniques. An improvement in the area under the curve of the receiver operating characteristic curve due to such enhancements can be at least 0.01, at least 0.05, or at least 0.1. An improvement in the area under the curve of the receiver operating characteristic curve due to such enhancements can be at least 1%, 2%, 3%, 4%, 5%, 6%, 7%, 8%, 9%, or 10%. In some cases, the area under the curve can increase by between 1% and 10%, between 2% and 10%, between 3% and 10%, between 1% and 7%, between 2% and 7%, between 3% and 7%, between 1% and 5%, or between 2% and 5%.

An enhanced algorithm can have a sensitivity of at least 70%, at least 75%, at least 80%, at least 85%, at least 90%, or at least 95%. In some cases, an enhanced algorithm can have a sensitivity of between 70% and 95%, between 70% and 90%, between 70% and 85%, between 70% and 80%, between 75% and 95%, between 75% and 90%, between 75% and 85%, between 75% and 80%, between 80% and 95%, between 80% and 90%, between 85% and 95%, between 85% and 90%, or between 90% and 95%. An enhanced algorithm can have a specificity of at least 70%, at least 75%, at least 80%, at least 85%, at least 90%, or at least 95%. In some cases, an enhanced algorithm can have a specificity of between 70% and 95%, between 70% and 90%, between 70% and 85%, between 70% and 80%, between 75% and 95%, between 75% and 90%, between 75% and 85%, between 75% and 80%, between 80% and 95%, between 80% and 90%, between 85% and 95%, between 85% and 90%, or between 90% and 95%.

In some embodiments, additional features can be extracted from permutations of how the images are contrasted, the differences between the features within the tumor and peritumoral regions, and the imaging type.

In addition to the features that are extracted from the images, a radiologist may also provide a score that assesses the degree of malignancy. In some embodiments, this is a priori information that can be provided to boost the classification accuracy of a machine learning algorithm. Disclosed herein includes a single BI-RADs-like criterion which assesses the degree of heterogeneity in tumor morphology. Such score, called the mass boundary (MB) score rates a tumor on a scale of 1 to 5. A low value reflects a well circumscribed lesion with well-defined margins while a higher score reflects an irregular or spiculated lesion with ill-defined margins extending into the peritumoral region. If greater than ⅔ of the lesion is circumscribed, then a score of 1 is given. If this perimeter is between ⅓ and ⅔, a score of 2 is given. If less than ⅓ of the lesion is circumscribed, then a score of 3 is given. If the lesion is quite irregular, a score of 4 is given. Likewise, if distinct speculations are seen, a score of 5 is given. In some embodiments, the MB score differs somewhat from an overall BI-RADs score in that the MB score classifies only the tumor/peritumoral morphology and is not meant to convey clinical decision of 12-month follow-up (BI-RADs 1 and 2), 6-month follow-up (BI-RADs 3), or recommendation for biopsy (BI-RADs 4 and 5). Indeed, the MB score may likely represent a smoother transition of cancer probability rather than the sharp inflection in probability from <2% with BI-RADs 3 to approximately 10-50% with BI-RADs 4.

In some embodiments, a total number of features in the range from 2 to 10000 may be extracted. In some embodiments, a total number of features in the range from 10 to 1000 may be extracted. In some embodiments, a total number of features in the range from 50 to 500 may be extracted.

In some embodiments, the extracted features comprise a plurality of subsets of related feature groupings or classes. One subset may comprise one or more sound propagation metrics characterizing sound speed, sound attenuation, sound reflection, or their combinations. One subset may include every feature in a single feature class. One subset may include more than one feature in a single feature class. One subset may include features from more than one feature classes. One subset may include fewer numbers of features than the total number of extracted features. In some embodiments, one subset may include all the features that are selected to train the classifier model herein.

In some embodiments, one subset of features may include 2 to 100 features. In some embodiments, one subset of features may include 20 to 80 features. In some embodiments, one subset of features may include 30 to 70 features. In some embodiments, one subset of features may include 40 to 60 features.

Feature Selection

A set of prognostic parameters can be trimmed. After features are extracted from the ROI, the extracted features may be trimmed in a feature selection step. In some cases, this trimming can be aided by a computer processor. In some embodiments, the number of extracted features before trimming may be comparable or greater than the number of patient samples. For example, when multiple imaging modalities are used, both the tumor and peritumoral regions are used, various contrast choices are made, and other permutations are included, the number of features explodes to be much greater than the number of patient samples. In some embodiments, one or more features may represent a dimension in hypothesis space the extracted features determine. However, the "curse of dimensionality" says that one need to have enough samples (patient data) such that the hypothesis space is densely sampled. Thus, in some embodiments, the number of features may be pruned or trimmed.

One can use many different method or various combinations of methods for feature selection. For example, decision trees can be made from subsets of the features such that each subset forms the union of the entire feature space. Training using these individual subsets generates decision trees where the greatest information gain is at the top nodes. The nodes of these trees (e.g., node at the top layers) can be aggregated to keep the most informative features. A univariate or multivariate analysis of the features can be done.

Nonlimiting example methods to accomplish feature selection or trimming includes: simulated annealing, genetic algorithms, forward selection, backward elimination, tree based filtering, and decision tree pruning. In some embodiments, decision tree pruning is used to reduce the dimensionality of the hypothesis space or feature space.

In some embodiments, the features are trimmed or selected based on a method selected from the group consisting of: principle component analysis, multilinear principle component analysis, and decision tree analysis.

A set of prognostic parameters can be trimmed (e.g., by a processor) based on an acceptable method. An acceptable method can be, for example, principle component analysis, multilinear component analysis, decision tree analysis, or using a support vector machine. In some cases, an acceptable method can be selected from the group consisting of principle component analysis, multilinear component analysis, decision tree analysis, and using a support vector machine. In some cases, an acceptable method can be selected from the group consisting of principle component analysis, multilinear component analysis, and decision tree analysis.

In some embodiments, principal component analysis (PCA) is used for feature selection and creation [Computer-aided diagnosis scheme for distinguishing between benign and malignant masses in breast DCE-MRI J Digit Imaging. 2016; 29:388-93], which is incorporated herein by this reference. In some cases, PCA takes as input a data set with many features and examples. It then reduces the number of features by eliminating those features which are not significant. In particular, it may create new features that are linear combinations of existing features. For example, if edgeness and tumor standard deviation are the most important metrics, the PCA procedure may independently identify them and combine them to yield the best possible classification of the data.

In some embodiments, one of the 10 main feature classes herein is selected, thus, one or more features within the selected class are selected. In some embodiment, other methods including but not limited to ICA (independent components analysis), RCA (random components analysis), neural network weight values, and permutations methods disclosed herein.

In some embodiments, machine learning methods such as the application of neural network or other deep learning techniques can be used for feature selection.

In some embodiments, a genetic algorithm can randomly select different features and then produce offspring where some of those features mate with other features. In some embodiments, a feed forward approach can be taken where each single feature is paired with another feature to generate multiple feature pairs. Each of the multiple feature pairs is used to train one or more selected machine learning algorithms using at least part of a training data set, the pair with the greatest machine learning accuracy (e.g., the accuracy may include one or more selected metrics such as specificity, false positive, false negative, sensitivity, PPV, etc) is then combined with each of the remaining features to generate multiple feature trios, each of which can undergo a new round of training and evaluation of accuracy. The trio with the greatest performance then can be combined with each of all the others features to generate multiple groups of four features. Such process may be repeated for a specified number of times or until stopping criteria are met. In some embodiments, a backwards reduction method can be used. All the extracted features, e.g., N features, can be used and a single feature is eliminated at a time to generate N subsets of N−1 features. The group of N−1 features with the poorest machine learning performance is eliminated. Such process may be repeated for a specified times or until stopping criteria are met.

In some embodiments, one or more feature classes for each image are selected and combined together to generate the selected features. For example, one of the feature classes, e.g., morphological features is selected for one of the images. Each feature class may include 10-20 features. The decision tree (e.g., J48) is trained on the selected feature class with at least a part of the training data, and top 2-3 layers of the resulting decision tree which contain the majority of information gain is retained. Repeat this process for more than one feature classes to obtain a number of features (e.g., 2-5 features) of each feature class for training J48 decision tree or other machine learning algorithms. In some embodiments, the top feature classes (e.g., top three) for each image and the corresponding features which appear on the tree nodes. In a particular embodiment, a total number of quantitative/textural features can be reduced to 43 from more than 500 features. If MBS and morphological features are included, it can be a total of 49 features. In some embodiments, each single feature in a decision tree with an optimal accuracy is selected rather than feature at the top layers of each decision tree.

In some embodiments, extracted features or trimmed features are partitioned into subcategories. These subcategories can include but are not limited to: acoustic parameter and textural features obtained using a detailed hand-drawn ROI (R), the same features obtained with a coarse elliptical ROI (RE), quantitative morphological features obtained from the detailed hand-drawn ROI (M), the mass boundary (MB) score, and combinations thereof.

In some embodiments, the training data set contains 161 (93 benign and 68 malignant) samples of breast lesions which includes 38 cysts, 55 fibroadenomas, and 68 cancers. In some embodiments, the training data set may contain any number of samples of breast lesions, the number greater than 10. In some embodiments, the training data set may include any non-zero number of benign samples, cyst samples, fibroadenoma samples, and cancerous samples. In some embodiments, the training set includes a subset of data that is for testing of the machine learning algorithms. The testing subset may be about ½, ⅓, ¼, ⅕, ⅙, or any other portion of the training set. In some embodiments, the training set may remain static or dynamically increasing when there are more data samples becoming available. In some embodiments, the training set may include data samples from different age groups, e.g., young, middle-age, senior groups of patients. In some embodiments, the training set may include data samples from different demographic groups, such as race. In some embodiments, the training set may include data samples from different stages of breast lesions.

A set of prognostic parameters can be trimmed to one of a plurality of subsets of prognostic parameters. In some cases, one of the plurality subsets can comprise one or a plurality of sound propagation metrics characterizing sound speed. In some embodiments, one of the plurality subsets can comprise the one or a plurality of sound propagation metrics characterizing sound attenuation. In some embodiments, one of the plurality subsets can comprise the one or a plurality of sound propagation metrics characterizing sound reflection.

A classifier model can determine a type of tissue having a sensitivity of at least X and a specificity of at least Y. In some cases X can be between 75% and 100%, between 80% and 100%, between 85% and 100%, between 90% and 100%, or between 95% and 100%. In some cases Y can be between 75% and 100%, between 80% and 100%, between 85% and 100%, between 90% and 100%, or between 95% and 100%.

A classifier model can determine a threshold value of one or more prognostic parameters sufficient to classify a tissue. A threshold value can be an upper threshold or a lower threshold. In some cases, a threshold can be a range. For example, if a prognostic parameter is above a lower threshold for a malignant lesion, a lesion might be classified as malignant A classifier model can determine a relative statistical accuracy of one or more prognostic parameters. In some embodiments, a relative statistical accuracy can be a specificity or sensitivity of tissue classification. In some cases, both specificity and sensitivity can be determined. In some cases, specificity, sensitivity, or both can be optimized.

A classifier model can builds a decision tree based on the accuracy of one or more prognostic parameters. A classifier model can build a decision tree based on the accuracy of a subset of prognostic parameters. In some embodiments, a classifier model can determine a threshold value of a subset of prognostic parameters sufficient to classify a tissue using a decision tree.

In some embodiments, the classifier model can determines a threshold value of a subset of prognostic parameters sufficient to classify a tissue. For example, a tissue can be classified as malignant or not malignant. In some cases, a percentage likelihood of malignancy can be determined. In some embodiments, classifier model can be generated using a machine learning technique. In some embodiments, a machine learning technique can comprises a support vector machine. In some embodiments, a support vector machine can comprise LibSVM, MATLAB, SAS, SVMlight, kernlab, scikit-learn, Shogun, Weka, Shark, JKernelMachines, OpenCV or another support vector machine.

In some embodiments, a machine learning technique comprises a decision tree. A decision tree can comprise J48, C4.5, or ID3. In some embodiments, a decision tree can comprise ADABoost or DecisionStump.

A machine learning technique can comprise a neural network. In some embodiments, the machine learning technique comprises k-nearest neighbors, perceptron, feed-forward, radial basis network, deep feed forward, recurrent neural network, long/short term memory, gated recurrent unit, auto-encoder, variational auto encoder, denoising auto encoder, sparse auto encoder, Markov chain, Hopfield network, Boltzmann machine, restricted Boltzmann machine, deep belief network, deep convolutional network, deconvolutional network, deep convolutional inverse graphics network, generative adversarial network, liquid state machine, extreme learning machine, echo state network, deep residual network, Kohonen network, a support vector machine, or a neural Turing machine.

Model Generation

Once features are selected, one or more subcategories of selected features can be put into a vector x. In some embodiments, they are combined with the labels y provided by the user (cyst, fibroadenoma, cancer, etc.) to generate a tuple (x,y). This can be done for each example of the tissue in the training set. If M such examples exist, then the training set S includes $S=\{(x\_1, y\_1), (x\_2, y\_2), \ldots, (x\_M, y\_M)\}$. In some embodiments, the training set is then fed to a machine learning algorithm, e.g., in the form of $f(x)=y$, for fitting or generating a fitted machine learning algorithm. In some embodiments, the machine learning algorithm includes a classifying or regression method. In some embodiments, the machine learning algorithm(s) is used to generate the classifier model $f(x)$ which maps feature(s) x to the corresponding label y or a regression score. In some embodiments, the machine learning algorithm(s) herein combines multiple algorithms. In some embodiments, the machine learning algorithm(s) herein includes multiple algorithms being trained simultaneously and compared for accuracy or performance.

In some embodiments, the classification, label, or type of the tissue include but is not limited to one or more of: a cancerous tumor, a fibroadenoma, a cyst, a nonspecific benign mass, and an unidentifiable mass. In some embodiments, the classification, label, or type of the tissue include but is not limited to malignant or benign.

In some embodiments, the classification, label, or type of the tissue includes 2, 3, 4, 5, 6 or even more different labels or types.

In some embodiments, the training is performed with a specified duration of time to meet clinical need. In some embodiments, the training is performed with a specified duration of time to fit into an existing clinical workflow. In some embodiments, the training is performed without overfitting. In some embodiments, the training is stopped when one or more stopping criteria are met.

In some embodiments, a classifier model, determines a threshold value of one or more prognostic parameters or features sufficient to classify a tissue. In some embodiments, the classifier model determines a relative statistical accuracy or performance of one or more prognostic parameters, such as specificity, sensitivity, or PPV. In some embodiments, the accuracy or performance of the classifier model is determined by one or more metrics including but not limited to sensitivity, specificity, false positive, false negative, duration of time for model training, duration of time for model fitting, computational complexity of model fitting, complexity of model, number of features selected, and number of classes for selected features.

In some embodiments, the classifier model includes a decision tree based on the accuracy of one or more prognostic parameters or subset of prognostic parameters in classifying a tissue or a ROI. In some embodiments, the classifier model determines a threshold value of a subset of prognostic parameters sufficient to classify a tissue using said decision tree.

In some cases, the classifier model determines a threshold value of a said subset prognostic parameters sufficient to classify a tissue, e.g., using a decision tree, or other classifiers.

In some embodiments, the classifier model is generated with a machine learning technique with or without a training set of data. In some embodiments, the training set of data includes image data and classification of corresponding image data or ROIs. In some embodiments, the training set of data includes no classification or label of ROIs.

Figure 13:
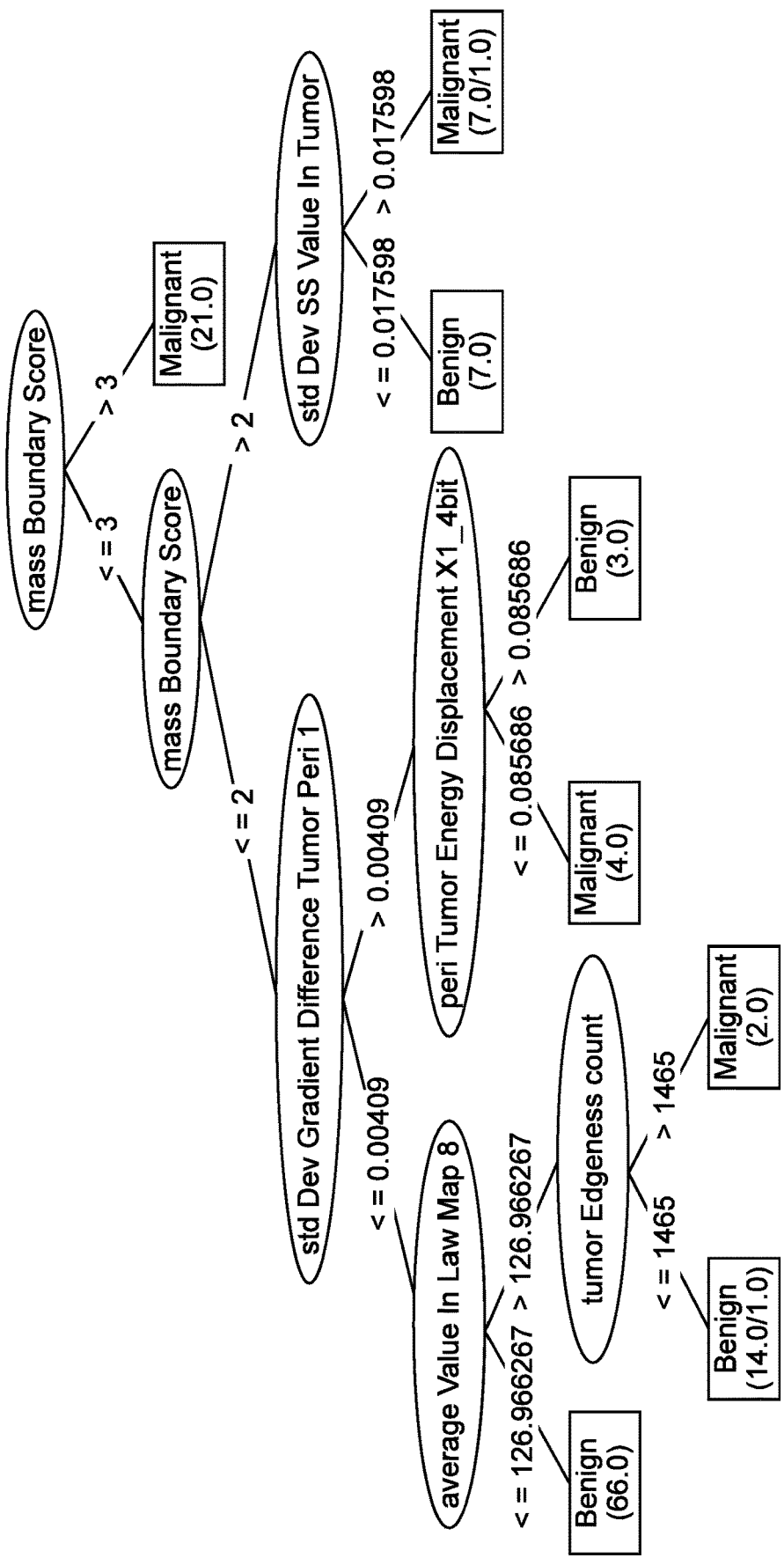
FIG. 13 illustrates a first example of a decision tree, in accordance with some embodiments.

In some embodiments, a decision tree, e.g., J48, C4.5, or ID3 decision tree, is trained on all features, and the trained decision tree is shown in FIG. 13. In some embodiments, the average correct classification±standard deviation is 85.23±3.65%. Other decision trees may be generated after training using no mass boundary score features (FIG. 14), no morphological measures (FIG. 15), or no mass boundary score or morphological measures (FIG. 16). The average correct classification±standard deviation using decision trees is 80.12±3.82%, 85.713±2.61%, and 70.24±5.02%, respectively. In some embodiments, selecting no morphological measures and training a decision tree thereon may advantageously generate a machine learning classifier for existing clinical work flow with good correct classification rate and no need for acquiring additional features that are not included in the current clinical flow, e.g., morphological features.

One of the examples of a decision tree is shown in FIG. 13. First, the MB is determined. If the MB is greater than 3, then the lesion is considered malignant. If the MB is less than 3, more analysis is needed. If the MB is less than 3 but greater than 2, the standard deviation of the sound speed value in the lesion is considered, and if the value is over a given threshold, the lesion is considered malignant. If the MB is less than or equal to 2, then the standard deviation of a gradient difference between a lesion and a peri-lesion can be considered. If the standard deviation of a gradient difference is above a given threshold, the peri-tumor energy displacement is considered. If the energy displacement is below a given threshold, the lesion is considered malignant. If the standard deviation of a gradient difference is below a given threshold, then the average value in a Law map is considered. If the average value is below a given threshold value, then the lesion is considered benign. If the average value is above a given threshold, then the tumor edgeness count can be considered. If the tumor edgeness count is above a given threshold, the lesion is considered malignant. Otherwise, the lesion is considered benign.

Figure 14:
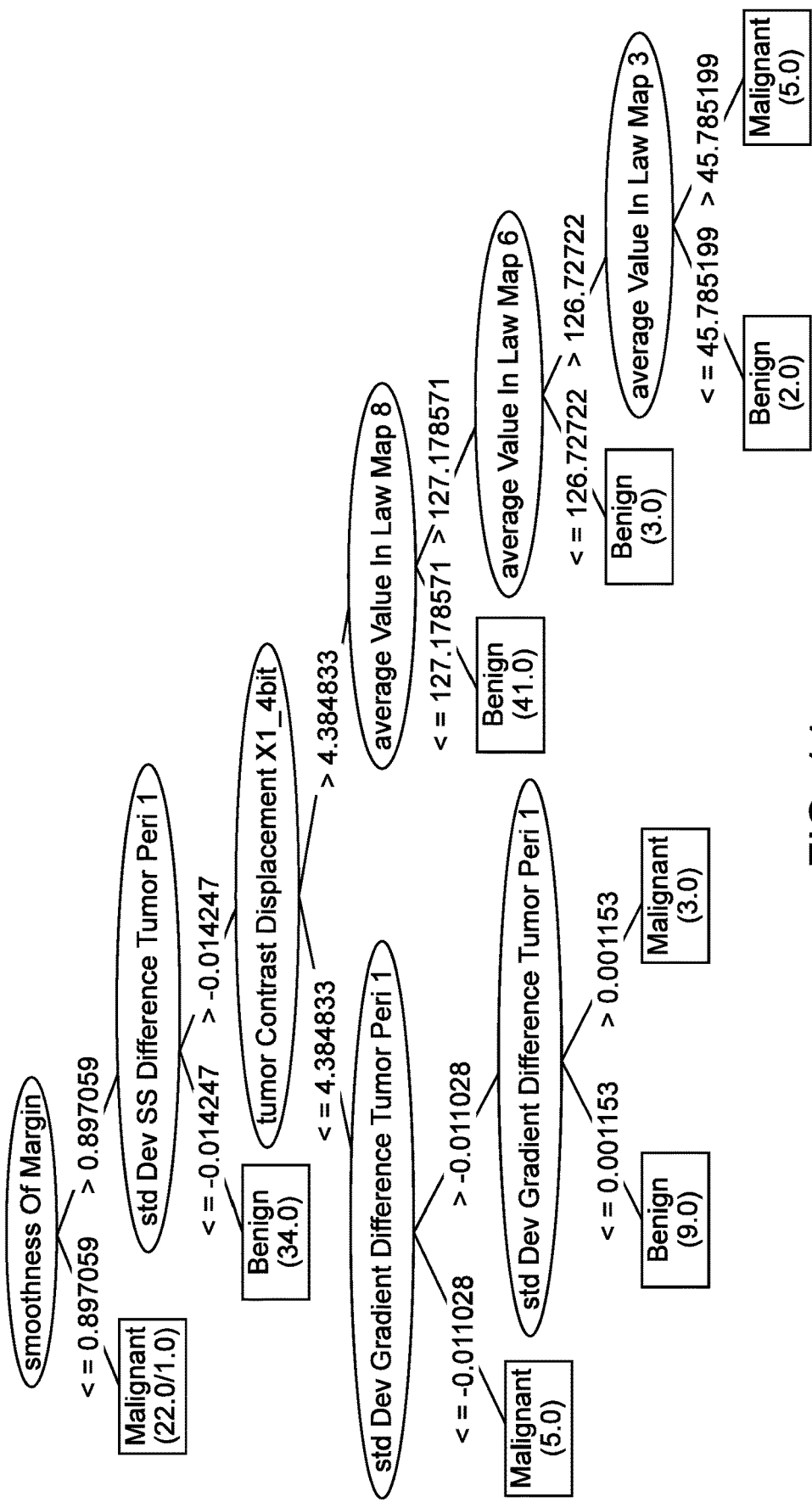
FIG. 14 illustrates a second example of a decision tree, in accordance with some embodiments.

One of the examples of a decision tree is shown in FIG. 14. Here, if the smoothness of a margin of a lesion is below a given threshold, the lesion is considered malignant. If the smoothness of a margin of a lesion is above a given threshold, then the standard deviation of the sound speed difference between the tumor and the peri-tumor is considered. If the standard deviation of a sound speed difference is below a given threshold, the tumor is considered benign; else the tumor contrast displacement is considered. If the tumor contrast displacement is below a given threshold, then the standard deviation of the difference of the gradient of the tumor and peri-tumor are considered. If the standard deviation of the gradient difference is below a given threshold, the lesion is benign; else the lesion is malignant. If the tumor contrast displacement is above a given threshold, then the average value in a Law map is considered. If the average value in a Law map is below a given threshold, the lesion is benign. If the average value in a law map is above a given threshold, then the average value in another Law map is considered. If the average value in the second Law map is less than a given threshold, the lesion is considered benign; else an average value in a third Law map is considered. If the average value of the third Law map is below a given threshold, the lesion can be considered benign; otherwise the lesion is considered malignant.

Figure 15:
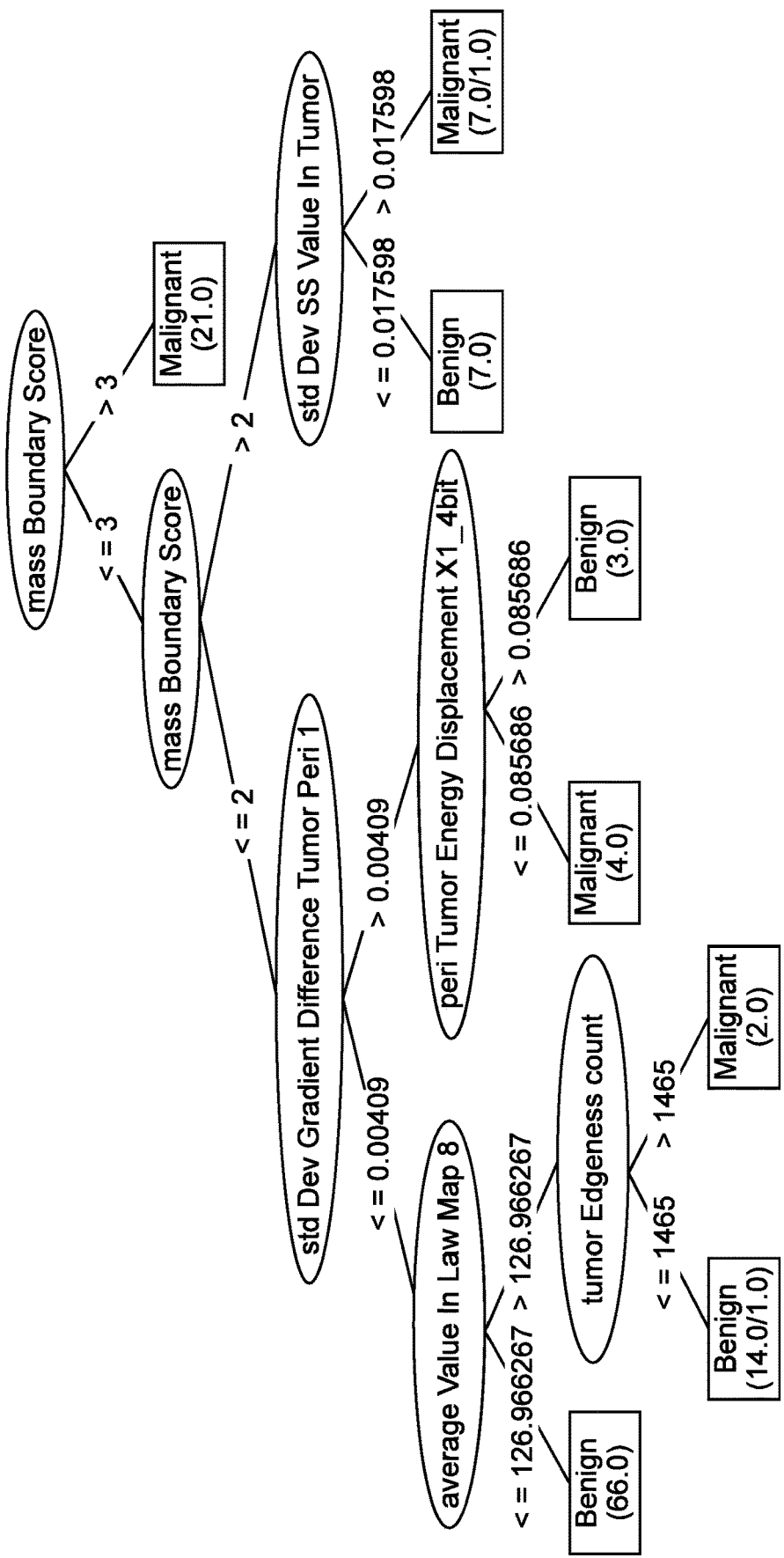
FIG. 15 illustrates a third example of a decision tree, in accordance with some embodiments.
Figure 16:
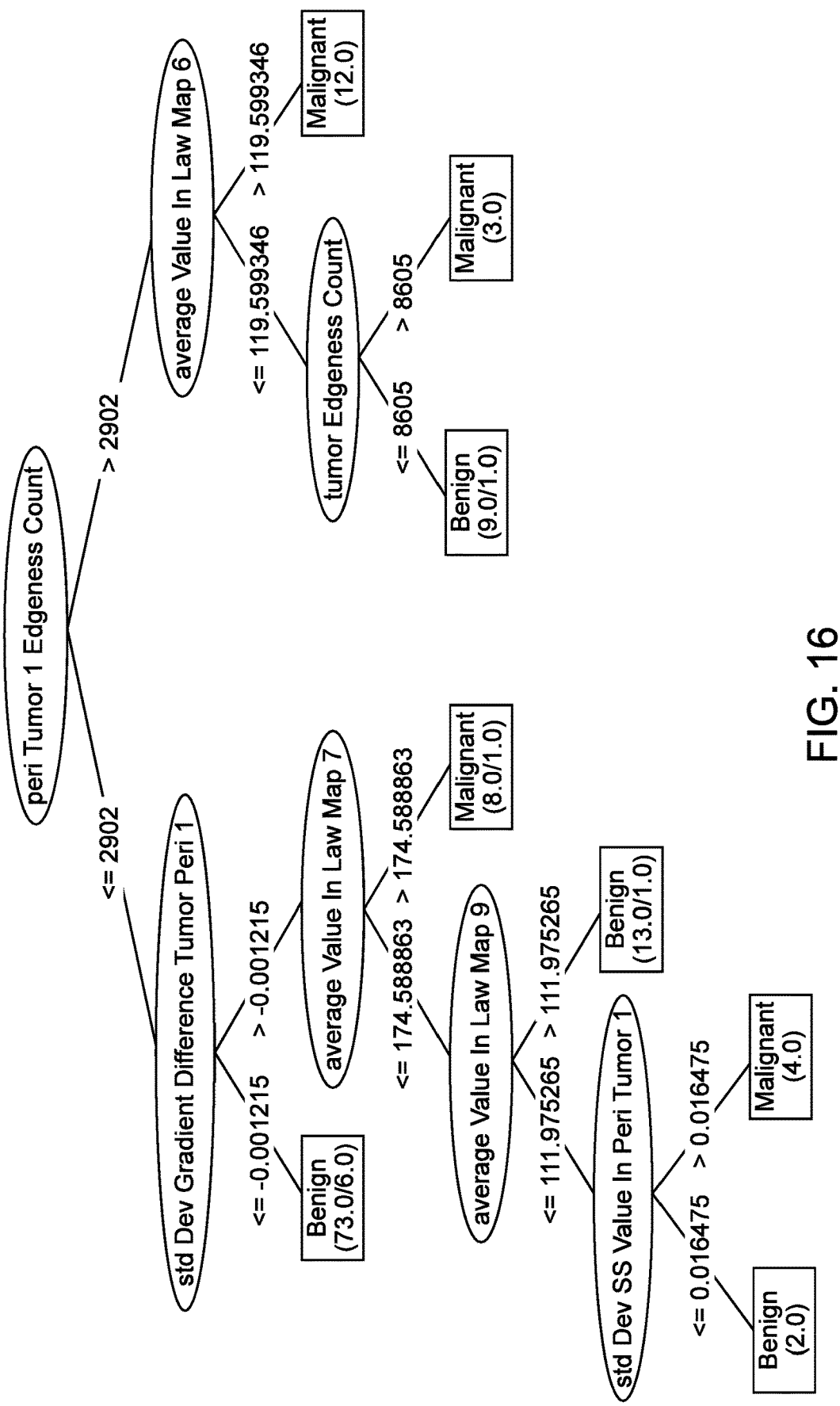
FIG. 16 illustrates an example of a decision tree, in accordance with some embodiments.

One of the examples of a decision tree is shown in FIG. 15. Here the MB is considered first. If the MB is greater than a threshold (here >3), then the lesion can be considered malignant. Else if the MB is greater than a lower threshold (e.g., greater than 2 but less than 3), then the standard deviation of the sound speed value in the lesion can be considered. If the standard deviation of the sound speed is below a threshold, the lesion can be malignant; else the lesion can be benign. If the MB is less than the lower threshold (e.g. less than 2), then the standard deviation of the difference in the gradient between the tumor and the peri-tumor can be considered. If the standard deviation of the gradient difference is below a given threshold, then the average value in a Law map is considered. If the average value in a Law map is below a given threshold, then the lesion can be considered benign. If the average value in a Law map is above a given threshold, then edgeness of a lesion can be considered. If the edgeness is below a given threshold, then the lesion can be considered benign. If the edgeness is above a given threshold, then the lesion can be considered malignant. If the standard deviation of the gradient difference is above a given threshold, then the energy displacement in a peri-tumor can be considered. If the energy displacement is below a given threshold, the lesion can be considered malignant. If the energy displacement is above a given threshold, the lesion can be considered benign.

One of the examples of a decision tree is shown in FIG. 16. Here, the edgeness of a peri-tumor is considered first. If the peri-tumor edgeness id above a given threshold, then the average value in a Law map is considered. If the average value in a Law map is above a given threshold, then the lesion can be considered malignant; else the edgeness count of a lesion can be considered. If the edgeness of a lesion is above a given threshold, the lesion can be considered malignant; else the lesion can be considered benign. If a peri-tumor edgeness is below a given threshold, then a standard deviation of a difference in the gradient between a tumor and a peri-tumor can be considered. If the standard deviation of the gradient difference is less than a given threshold, the lesion can be considered benign; else the average value in a Law map can be considered. If the average value in a Law map is above a given threshold, the lesion can be considered malignant; else the average value in a different Law map can be considered. If the average value in this second Law map is above a given threshold, the lesion can be considered benign; else the standard deviation of the sound speed image at a peri-tumor can be considered. If the standard deviation of the sound speed image at a peri-tumor is above a given threshold, the lesion can be considered malignant; else the lesion can be considered benign.

The systems and methods described herein may use machine learning algorithms for training classification models and/or making classifications (e.g., for labeling benign and malignant breast tissue in images from different imaging modalities. Machine learning algorithms herein may learn from and make classification on unknown data. Data may be any input, intermediate output, previous outputs, or training information, or otherwise any information provided to or by the algorithms.

A machine learning algorithm may use a supervised learning approach. In supervised learning, the algorithm can generate a function or model from training data. The training data can be labeled. The training data may include metadata associated therewith. Each training example of the training data may be a pair consisting of at least an input object and a desired output value. A supervised learning algorithm may require the user to determine one or more control parameters. These parameters can be adjusted by optimizing performance on a subset, for example a validation set, of the training data. After parameter adjustment and learning, the performance of the resulting function/model can be measured on a test set that may be separate from the training set. Regression methods can be used in supervised learning approaches.

In some embodiments, the supervised machine learning algorithms can include but not being limited to neural networks, support vector machines (e.g., Lib SVM), nearest neighbor interpolators, decision trees, boosted decision stump, boosted version of such algorithms, derivatives versions of such algorithms, or their combinations. In some embodiments, the machine learning algorithms can include one or more of: a Bayesian model, decision graphs, inductive logic programming, Gaussian process regression, genetic programming, kernel estimators, minimum message length, multilinear subspace learning, naive Bayes classifier, maximum entropy classifier, conditional random field, minimum complexity machines (MCM), random forests, ensembles of classifiers, and a multicriteria classification algorithm.

In some cases, a machine learning algorithm can be a support vector machine. A support vector machine can be a supervised learning model, which can have associated learning algorithms. Associated learning algorithms can analyze data which can be used for classification of a lesion.

In a support vector machine, each of a set of training samples can be marked as belonging to a category, such as malignant and benign. A support vector machine algorithm can build a model that can assign new examples to one of the categories (e.g., malignant or benign). In some cases, a support-vector machine can be a non-probabilistic binary linear classifier.

A machine learning algorithm may use a semi-supervised learning approach. Semi-supervised learning can combine both labeled and unlabeled data to generate an appropriate function or classifier.

In some embodiments, a machine learning algorithm may use an unsupervised learning approach. In unsupervised learning, the algorithm may generate a function/model to describe hidden structures from unlabeled data (i.e., a classification or categorization that cannot be directed observed or computed). Since the examples given to the learner are unlabeled, there is no evaluation of the accuracy of the structure that is output by the relevant algorithm. Approaches to unsupervised learning include: clustering, anomaly detection, and neural networks.

A machine learning algorithm may use a reinforcement learning approach. In reinforcement learning, the algorithm can learn a policy of how to act given an observation of the world. Every action may have some impact in the environment, and the environment can provide feedback that guides the learning algorithm.

A machine learning algorithm may use a transduction approach. Transduction can be similar to supervised learning, but does not explicitly construct a function. Instead, tries to predict new outputs based on training inputs, training outputs, and new inputs.

A machine learning algorithm may use a "learning to learn" approach. In learning to learn, the algorithm can learn its own inductive bias based on previous experience.

A machine learning algorithm is applied to patient data to generate a prediction model. In some embodiments, a machine learning algorithm or model may be trained periodically. In some embodiments, a machine learning algorithm or model may be trained non-periodically.

As used herein, a machine learning algorithm may include learning a function or a model. The mathematical expression of the function or model may or may not be directly computable or observable. The function or model may include one or more parameter(s) used within a model. For example, a linear regression model having a formula Y=C0+C1x1+C2x2 has two predictor variables, x1 and x2, and coefficients or parameter, C0, C1, and C2. The predicted variable in this example is Y. After the parameters of the model are learned, values can be entered for each predictor variable in a model to generate a result for the dependent or predicted variable (e.g., Y).

Online Use

In some embodiments, the online use pipeline includes images/data that has not been used in offline training. In some embodiments, the online use pipeline involves a user creating an ROI in order to segment the unlabeled images. The peri/inner tumoral region can be generated in a similar fashion as the regions in the offline training. Likewise, features can be extracted from the ROIs in a similar manner as that in offline training.

In some embodiments, the features in online use only include the selected features from offline training. In some embodiments, the features in online use include additional features other than the selected features from offline training.

In some embodiments, the features are then fed to the trained classifier to generate classification, a label or a regression score. In some embodiments, the label and/or regression score is displayed to the user. In some embodiments, the most informative features that correspond to the label/score can be presented to the user.

In some cases, the efficacy of systems and methods herein are evaluated using the sensitivity (SEN), specificity (SPF), and positive predictive value (PPV) of the trained classifiers. The definitions of SEN, SPF, and PPV may not be what they may typically mean for detecting lesions in medical images. Instead, the radiologist has already found the lesion and contoured it. In some embodiments, the classifier labels the region as benign or malignant. In some embodiments, the classifier's SEN, SPF, and PPV thus reflect the ability to properly label the region as benign or malignant. To reduce over-fitting and have a classifier model which generalizes well, it is important to test the classifier on a separate testing set. For testing herein, the data is not explicitly partitioned into a training and testing set. Instead, a stratified shuffle split cross-validation approach is used. Also, the improvement of the classification herein over randomly guessing in SEN, SPF, and PPV are used to better estimate eventual clinical utility. Table 2 shows the improvements in sensitivity (SEN), specificity (SPF), and positive predicative value (PPV) over random guessing when using specific categories of features, wherein such categories of features includes textural features obtained using a detailed hand-drawn ROI (R), the same features but with a coarse elliptical ROI (RE), quantitative morphological features obtained from the detailed hand-drawn ROI (M), and the mass boundary (MB) score.

TABLE 2

| Feature Category | SEN | SPF | PPV |
| --- | --- | --- | --- |
| R | 27.9% | 25.1% | 34.8% |
| RE | 23.6% | 20.8% | 29.4% |
| R + M | 31.0% | 28.3% | 38.9% |
| R + MB | 35.4% | 38.0% | 51.5% |
| RE + MB | 32.5% | 39.1% | 52.9% |

Auto Segmentation

Auto-segmentation can be performed on images, e.g. sound speed images, reflection images, or wafer images. In some cases, where all three image types are available, auto-segmentation can be performed on a sound speed image, on a reflection image, and on a wafer image.

Once an image is obtained, a region of interest can be indicated on the image. In some cases, this region of interest can be drawn on the image. In some cases, a radiologist can draw the region of interest. The region of interest can encompass a lesion, can intersect a lesion, or can be in the vicinity of a lesion. The region of interest can comprise a portion of the image which is not lesion.

Auto-segmentation can be performed using one of three algorithms: Markov Random Field, Gaussian Mixture Model, and Adaptive Fuzzy C-Mean. In some embodiments, all three auto-segmentation algorithms can be performed on an image. In some cases, one of the Markov Random Field, Gaussian Mixture Model, and Adaptive Fuzzy C-Mean algorithms and two other auto-segmentation algorithms can be performed. In some cases, two of the Markov Random Field, Gaussian Mixture Model, and Adaptive Fuzzy C-Mean algorithms can be performed.

A Markov Random Field auto-segmentation can be performed on an image $y=(y_1, \ldots, y_N)$ where each $y_i$ is the intensity of a pixel, and a configuration of labels $X=(x_1, \ldots, x_N)$ where $x_i$ can be inferred. In some cases, the labels X can be binary. The labels X can be obtained, for example as:

$$X^* = \mathrm{argmax}\{P(y/x,\theta)P(x)\}$$

where P(x) is a Gibbs distribution(1/z exp(−ΣV(x))), and P(y/x, θ)=Π$_i$P(y$_i$|x$_i$, θ$_i$) with Gaussian distribution. In addition, the parameters θ can be obtained by an Expectation-Maximization (EM) algorithm with Expectation (E) and Maximization (M) steps.

The E step can calculate a conditional expectation, for example as:

$$Q(\theta|\theta^t) = \Sigma P(x|y,\theta^t) \ln P(x,y|\theta)$$

The M-step can maximize an expectation Q, such as the Q calculated in the E step, to obtain next step of θ parameters, for example as:

$$\theta^{t+1} = \mathrm{argmax}\ Q(\theta|\theta^t)$$

Figure 17:
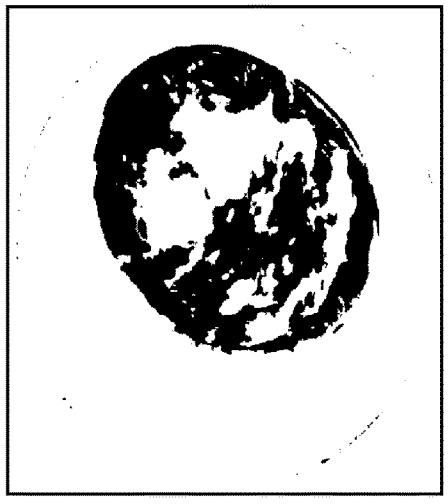
FIG. 17 illustrates the result of applying a Markov random field for auto-segmentation on a sound speed image, on a reflection image, and on a wafer image, in accordance with some embodiments.
Figure 17:
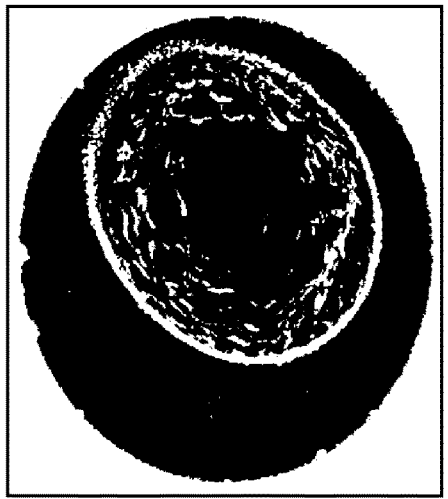
Figure 17:
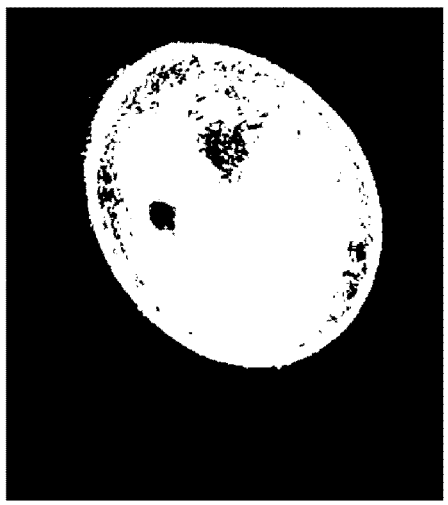
Figure 17:
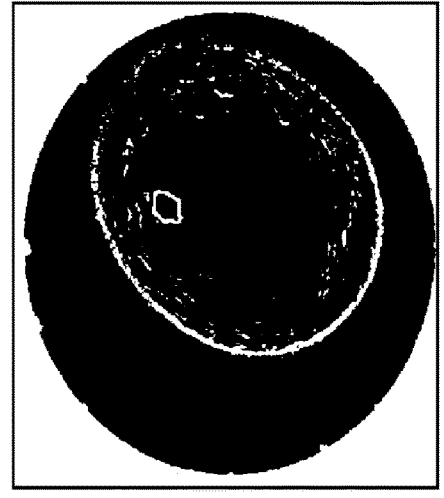
Figure 17:
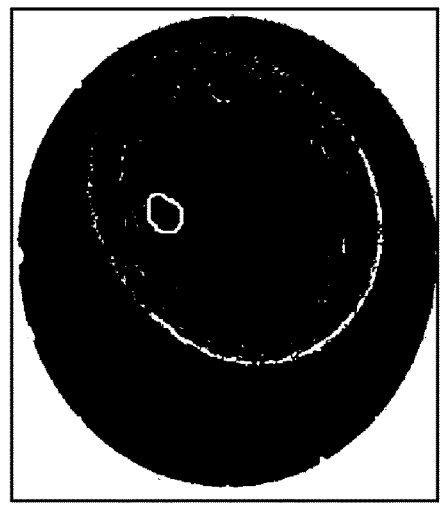
Figure 17:
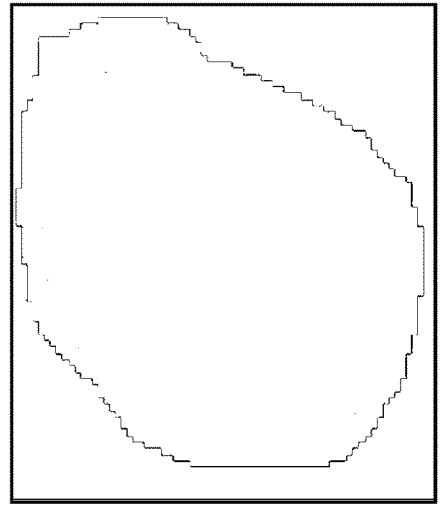

An example of a result of using a Markov random field for auto-segmentation on a sound-speed image, on a reflection image, and on a wafer image is shown in FIG. 17. Panel (a) depicts a sound speed image, panel (b) depicts a reflection image, and panel (c) depicts a Wafer image. Panel (d) depicts a reflection image which has been segmented using a Markov random field. Panel (e) depicts a reflection image which has been manually segmented by a radiologist. Panel (f) depicts a comparison of a mask created from the segmentation (white) to a mask created from the manual segmentation by a radiologist (gray).

A Gaussian Mixture Model auto-segmentation can be performed on an image, for example when it can be assumed that the pixels on the image were generated from a mixture of a finite number of Gaussian distributed components with unknown parameters. In some cases, the parameters of the components can comprise mean, covariance, mixture properties, or a combination thereof. Parameters of the components can be obtained, estimated, or determined using an Expectation-Maximization (EM) algorithm, which can comprise Expectation (E) and Maximation (M) steps. Prior to the E step, values can be initialized. For example, values which might be initialized can include component means, covariance matrix, or mixing properties. The E step can be performed, wherein posterior probabilities of component membership for at least one pixel and up to all pixels can be computed. In some cases, posterior probabilities can be computed for each pixel in a user-selected region of interest. The M step can be performed after the E step. For example, the M step can use one or more component-membership posterior probability weights to calculate features. Features calculated in the M step can include component means, covariance matrix, and mixing properties. In some cases, such features can be determined, calculated, or obtained using an algorithm such as a maximum likelihood algorithm.

After parameters of components are obtained, the probability of membership of one or more pixels is calculated. The probability of membership can be calculated for each pixel in a user-selected region of interest. A pixel having a particular feature can be labeled. In some cases, a pixel having the maximum probability or a probability over a specified threshold can be labeled. In some cases, more than one pixel can be labeled as having a maximum probability or a probability over a specified threshold can be labeled.

Figure 18:
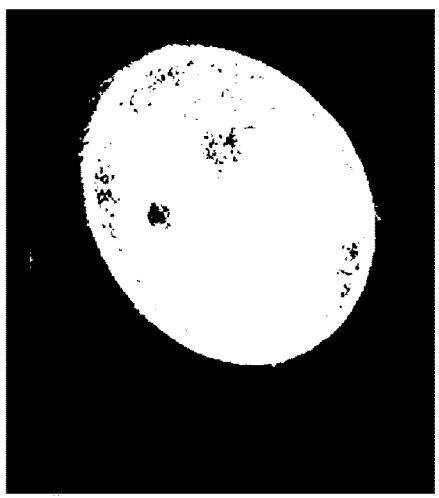
FIG. 18 illustrates the result of applying a Gaussian mixture model for auto-segmentation on a sound speed image, on a reflection image, and on a wafer image, in accordance with some embodiments.
Figure 18:
Figure 18:
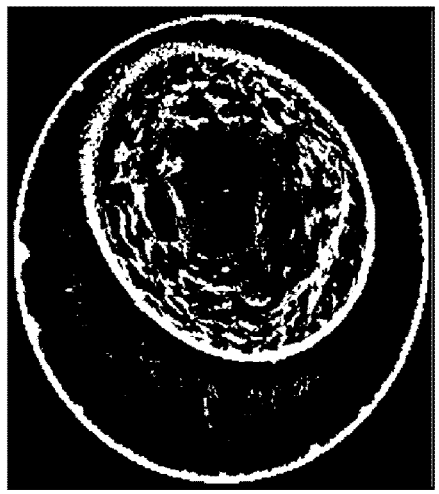
Figure 18:
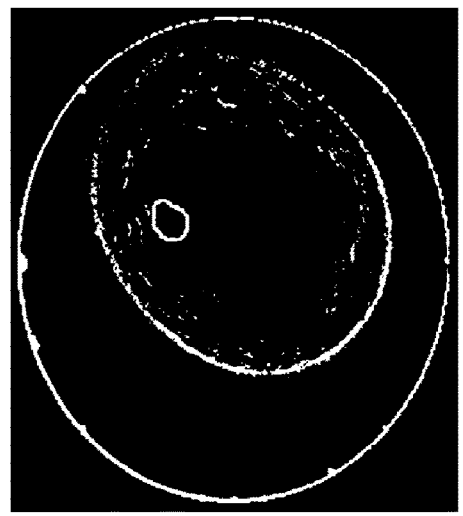
Figure 18:
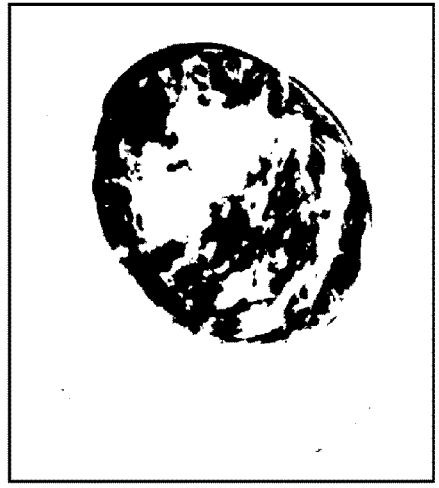
Figure 18:
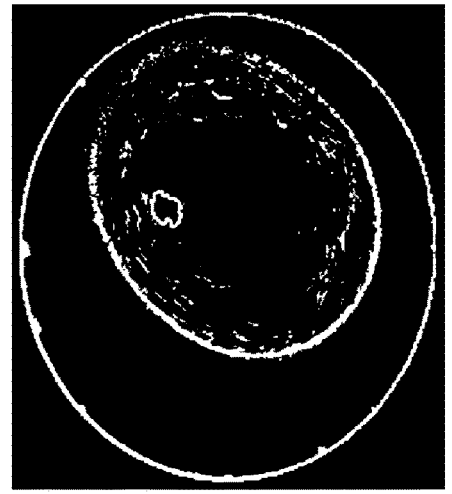

An example of a result of using a Gaussian mixture model on a sound speed image, a reflection image, and a wafer image is shown in FIG. 18. Panel (a) depicts a sound speed image, panel (b) depicts a reflection image, and panel (c) depicts a Wafer image. Panel (d) depicts a reflection image which has been segmented using a Gaussian Mixture Model. Panel (e) depicts a reflection image which has been manually segmented by a radiologist. Panel (f) depicts a comparison of a mask created from the segmentation (white) to a mask created from the manual segmentation by a radiologist (gray).

An adaptive fuzzy C-mean auto-segmentation can be performed on an image y=(y_1, . . . , y_N) where each y_i is the intensity of a pixel. A configuration of labels X= (x_1, . . . , x_N) where x_i are binary can be inferred. The labels can be inferred using a minimization algorithm, for example:

$$J_m = \sum_i^N \sum_j^C u_{ji}^m \|y_i - v_j\|^2 + \frac{a}{N_R} \sum_i^N \sum_j^C u_{ji}^m \sum_{r \in N_i} \|y_r - v_j\|^2$$

where y data can input in m dimensional space, N can be a number of data items, c can be a number of clusters, $u_{ji}$ can be a degree of membership of a $j^{th}$ pixels with respect to a cluster J, $N_R$ can be a cardinality, $y_r$ can represent the neighbor of $y_i$, $N_i$ can be a set of neighbors which can reside in a window around pixel $y_i$, and a can be a parameter which can control an effect of a neighbor's term. In some cases, u can be calculated as:

$$\frac{\left(\|y_i - v_j\|^2 + \frac{a}{N_R} \sum_{r \in N_i} \|y_r - v_j\|^2\right)^{\frac{1}{m-1}}}{\sum_k^c \left(\|y_i - v_k\|^2 + \frac{a}{N_R} \sum_{r \in N_i} \|y_r - v_k\|^2\right)^{\frac{1}{m-1}}}$$

where $x_i$ can be obtained by finding a maximum $u_{ji}$ with respect to the clusters.

Figure 19:
FIG. 19 illustrates the result of applying a fuzzy C-mean for auto-segmentation on a sound speed image, on a reflection image, and on a wafer image, in accordance with some embodiments.
Figure 19:
Figure 19:
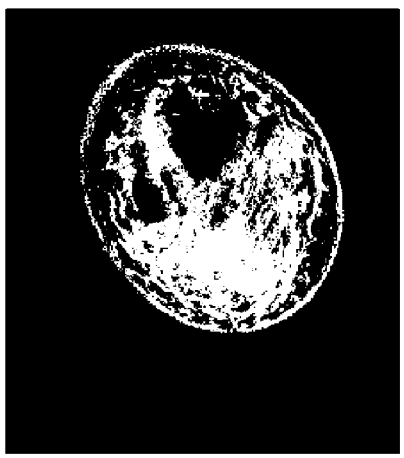
Figure 19:
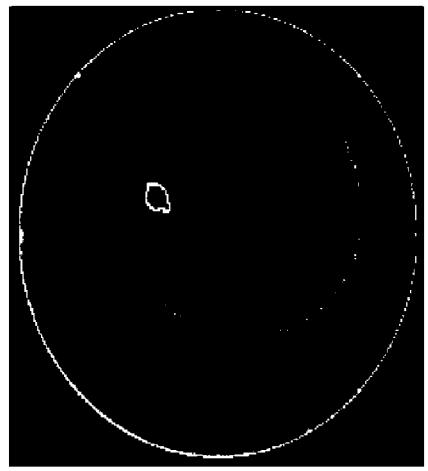
Figure 19:
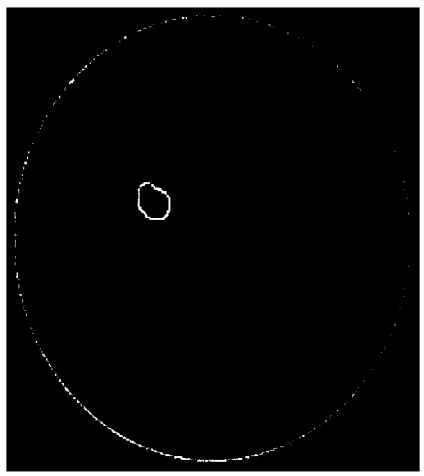
Figure 19:
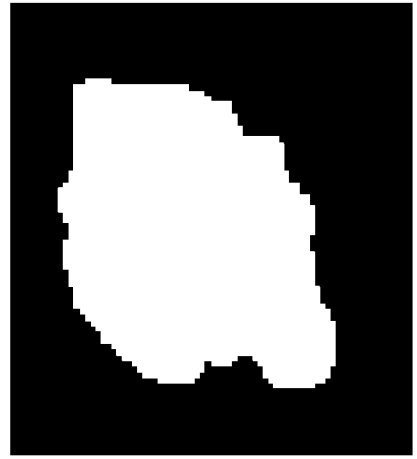

An example of a result of using an adaptive fuzzy C-mean on a sound speed image, a reflection image, and a wafer image is shown in FIG. 19. Panel (a) depicts a sound speed image, panel (b) depicts a reflection image, and panel (c) depicts a Wafer image. Panel (d) depicts a reflection image which has been segmented using an adaptive fuzzy C-mean. Panel (e) depicts a reflection image which has been manually segmented by a radiologist. Panel (f) depicts a comparison of a mask created from the segmentation (white) to a mask created from the manual segmentation by a radiologist (gray).

In some cases, three segmentation methods, typically auto-segmentation methods, can be applied to an image. In some such cases, the three auto-segmentation methods can be Markov Random Field, Gaussian Mixture Model, and Adaptive Fuzzy C-Mean. In some cases, other segmentation or auto-segmentation methods or algorithms can be one of the three segmentation images.

Figure 20:
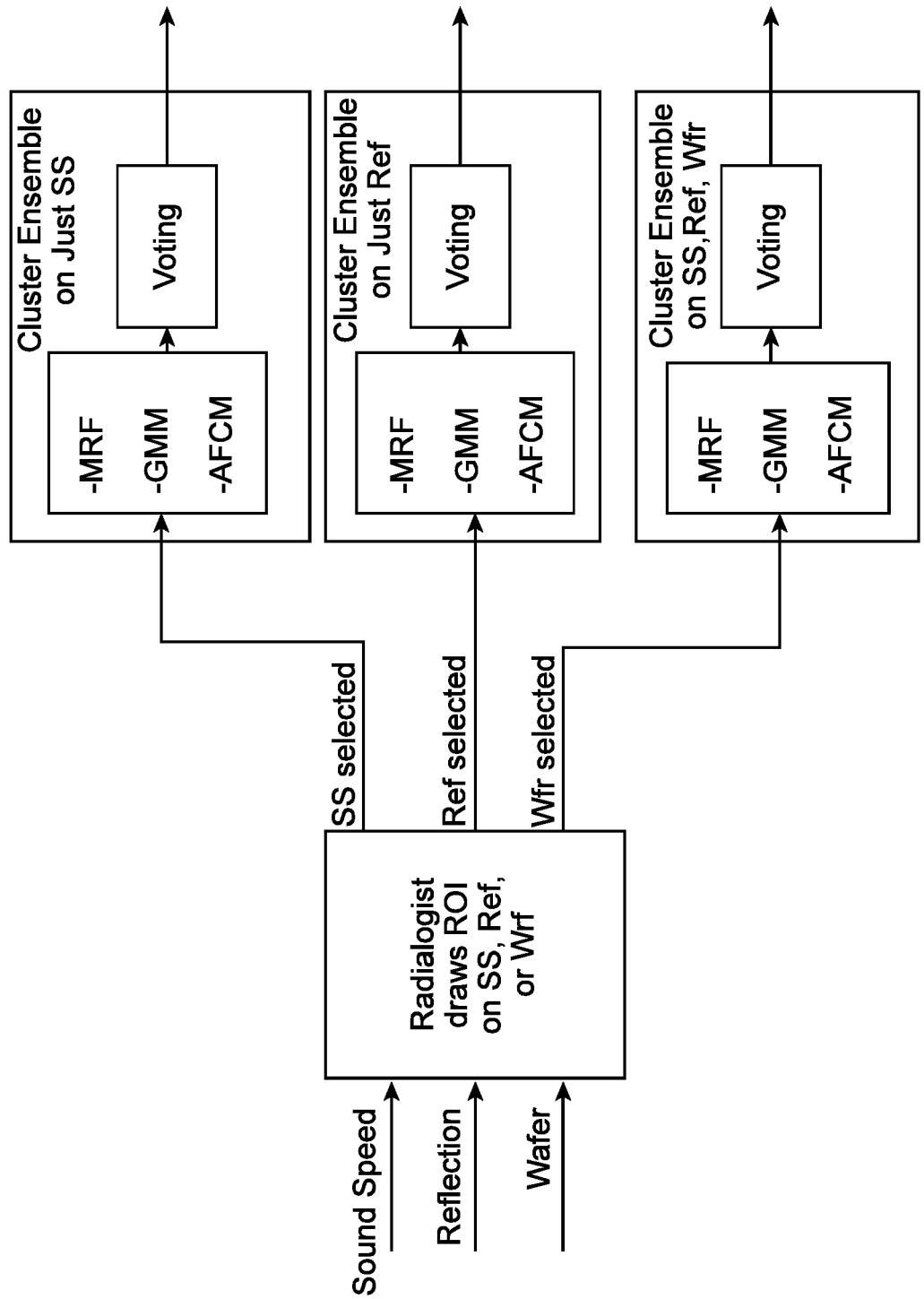
FIG. 20 illustrates a diagram of a pixel-wise voting technique, in accordance with some embodiments.

A pixel-wise voting technique can be applied, for example such that for each pixel, each segmentation result can be considered when determining whether the pixel is a part of a lesion. A pixel-wise voting technique can combine segmentation results of segmentation algorithms, for example, by addition. A diagram of a pixel-wise voting technique is illustrated in FIG. 20.

As an example, masks derived from Markov random field segmentation, Gaussian Mixture Model segmentation, and adaptive fuzzy C-mean segmentation can be acquired. In some cases, the masks can be binary. In such a case, if a pixel has a value of "1" then that pixel may be indicated as part of a lesion, while if a pixel has a value of "0" then that pixel may be indicated as not part of a lesion. The three masks can be added to yield a voting matrix. The voting matrix can comprise pixels having values equal to 0, 1, 2, or 3. In some cases, if a pixel value is 0, then the pixel is not indicated to be part of a lesion in any mask. If a pixel value is 1, then one auto-segmentation algorithm yielded a result indicating that that pixel is part of a lesion. If a pixel value is 2, then two auto-segmentation algorithms yielded results indicating that that pixel is part of a lesion. If a pixel value is 3, then three auto-segmentation algorithms yielded results indicating that that pixel is part of a lesion.

If a pixel value of a voting matrix is at least a threshold value, then that pixel can be considered part of a lesion. In some cases, a threshold value can be 1, in which case a pixel may be identified in only 1 algorithm. In some cases, a threshold value can be 2, in which case a pixel may be identified by 2 of 3 algorithms (e.g., 2 of 3 algorithms agree). In some cases, a threshold value can be 3, in which case a pixel may be identified by all 3 algorithms (e.g., all 3 algorithms agree).

If a pixel is at least a threshold value, in a final mask that pixel can be assigned a value of 1. Otherwise, the pixel can be assigned a value of 0. The final mask can be a mask indicating a location of a lesion which can comprise information from all 3 auto-segmentation algorithms.

A pixel-wise voting technique can be applied to a 2-dimensional image or to a 3-dimensional image. In some cases, a pixel-wise voting technique can be applied to multiple 2-dimensional images of a 3-dimensional region which approximates a 3-dimensional image.

For example, a mask can be created for each segmentation result to yield a Markov random field mask, a Gaussian Mixture Model mask, and an adaptive fuzzy C-mean mask.

Lesion Analysis Tool

Figure 21:
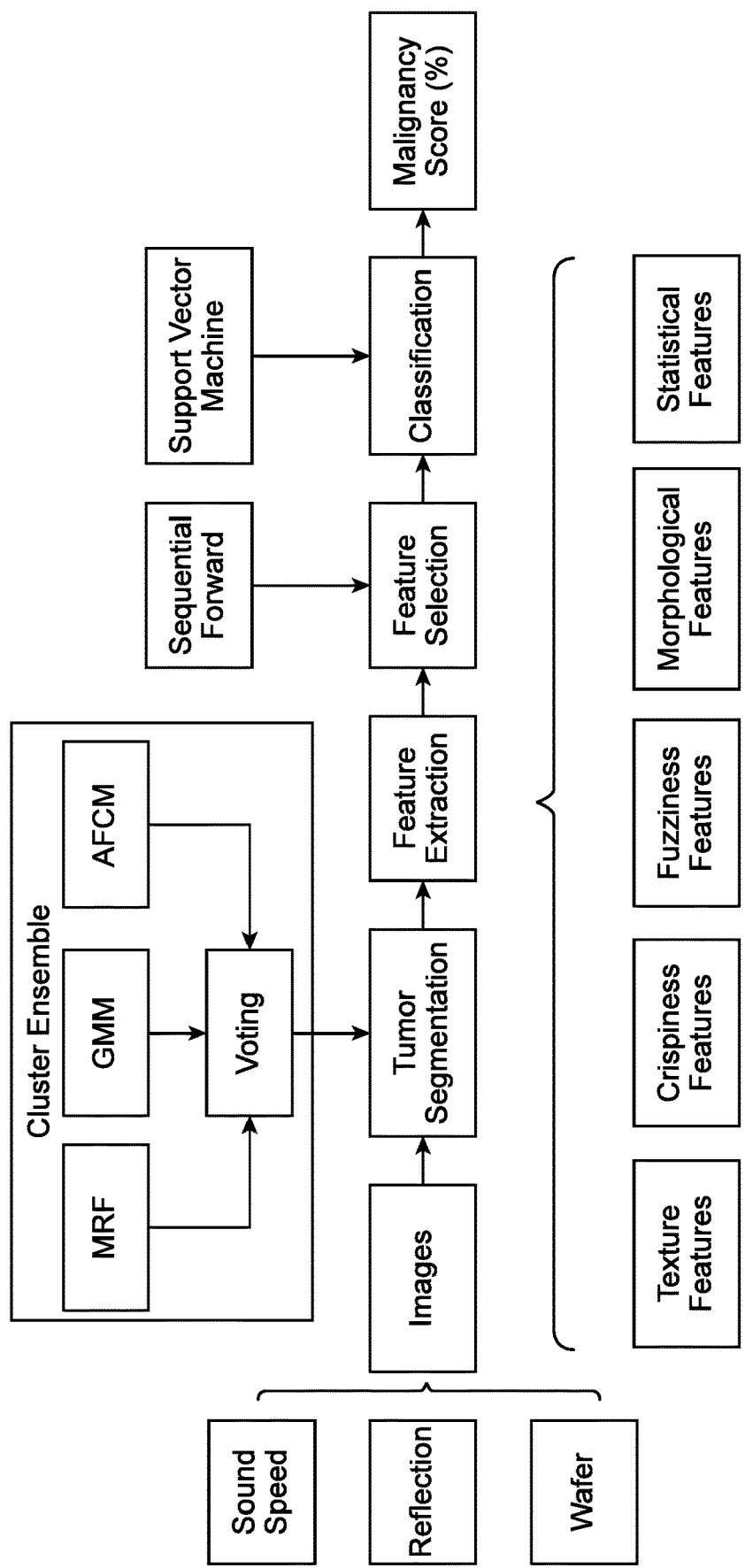
FIG. 21 illustrates a lesion analysis tool algorithm for the classification of a lesion, in accordance with some embodiments.

In some cases, a lesion can be analyzed by an tool, such as the one depicted in FIG. 21 The input image can be a sound speed image, a reflection image, or a wafer image. In some cases, the input can be a sound speed image and a reflection image. In some cases, the input can be a sound speed image and a wafer image. In some cases, the input can be a reflection image and a wafer image. In some cases, the input can be a sound speed image, a reflection image, and a wafer image.

The input images can be segmented as described herein. The segmentation can be performed for example to identify a lesion, e.g. a cancerous lesion or a non-cancerous lesion such as a cyst or fibroadenoma. In FIG. 21, the segmentation is indicated as the "Cluster Ensemble."

Images can be segmented via a Markov random field algorithm (MRF), a Gaussian mixture model algorithm (GMM), or an adaptive fuzzy C-mean algorithm (AFCM). In some cases, an image is segmented by all three algorithms (MRF, GMM, and AFCM) individually. In some cases that all three algorithms are used, a pixel-wise voting technique such as those described herein can be used to determine which pixels belong to the lesion (e.g. tumor).

Once the lesion has been segmented, features can be extracted by acceptable methods, such as those described herein. In some cases, one or more of texture features, crispiness features, fuzziness features, morphological features, or statistical features can be extracted. If more than one feature or type of feature is extracted, then additional features which can be determined using a combination of the extracted features can be calculated or derived.

Features can then be selected. For example, features which can most accurately, precisely, or specifically identify or classify a lesion can be selected. This selection can be achieved by an acceptable algorithm or method, such as a sequential forward selection algorithm. In some cases, sequential forward selection can start with an empty set, and can sequentially add features that maximize an objective function. The algorithm can be repeated until an objective converges to a maximum, or until an objective changes by an amount lower than a threshold value during an iteration. A threshold value here can be a change of less than 5%, less than 1%, less than 0.5%, less than 0.1%, less than 0.05%, or less than 0.01%.

Other algorithms which can be used in lieu of or in combination with a sequential forward selection algorithm can included a branch and bound, approximate image monotonicity with branch and bound, beam search, sequential backward selection, plus-I minus-r selection, bidirectional search, sequential floating selection, random generation plus sequential selection, simulated annealing, or genetic algorithms.

The lesion can be classified. In some cases, the classification can be performed using a supervised learning algorithm. For example, a support vector machine can be used to classify the lesion. The support vector machine can use a labeled data input (e.g., data which can have features identified, and which the malignancy is known) to build a model that can assign new examples to one category or another (e.g., malignant or not-malignant).

In some cases, another supervised learning model such as linear regression, logistic regression, naive Bayes, linear discriminant analysis, decision trees, k-nearest neighbor algorithm, neural networks, or similarity learning can be employed to classify the lesion.

A malignancy score can be presented. A malignancy score can be a score which can indicate the likelihood that a lesion is malignant or cancerous. In some cases, a malignancy score can be expressed as a percentage. Such a malignancy score can range between 0% and 100%. In some cases, a malignancy score of 0% can indicate a 0% chance that a lesion is malignant. In some cases, a malignancy score of 100% can indicate a 100% chance that a lesion is malignant. In some cases, a malignancy score can be x %, where x can be between 0 and 100 inclusive, which can indicate a x % chance that a lesion is malignant.

In some cases, a lesion analysis tool algorithm can have a sensitivity or a specificity. A sensitivity of such a tool can be about 85%. A sensitivity of such a tool can be at least 75%, 80%, 85%, 90%, or 95%. A specificity of such a tool can be about 90%. A specificity of such a tool can be at least 80%, 85%, 90%, or 95%. In some cases, specificity can be at least 35%, at least 40%, at least 50%, at least 60%, at least 70%, at least 80%, or at least 90%.

The selected ROI may be characterized using a classifier model based on a set of prognostic parameters. Set of prognostic parameters may comprise one or many types of acoustic data corresponding to sound propagation in a volume of tissue. Such types of acoustic data includes but is not limited to, for example: quantitative acoustic data (e.g., acoustic sound speed, acoustic attenuation, and acoustic reflection), quantitative morphological data (e.g., an area, diameter, ellipticity, etc. of an ROI), and qualitative morphological data (e.g., a user assessed parameter). Additionally or alternatively, the classifier model may use threshold values of any prognostic parameter and/or multiples of prognostic parameters. A threshold value of a prognostic parameter may be selected from a known value inherent to a lesion type. A threshold value of a prognostic parameter may be selected by a user. A threshold value of a prognostic parameter may be selected based on a computer-implemented algorithm. A selected threshold value and/or combination of threshold values may be optimized by such an algorithm in order to improve characterization of a lesion.

At a step 270 of the method 200, a lesion within the volume of tissue may be characterized using the subset of prognostic parameters. The prognostic parameters may be used within a classifier model in order to classify, predict, or otherwise characterize the region of interest. The analysis may predict whether the region of interest may be a cancerous mass, a benign fibroadenoma, a cyst, another benign finding, an unidentifiable mass (for example, there may be no finding), or any suitable characterization or classification. However, the analysis may additionally and/or alternatively monitor trends of one or more prognostic parameters over time, or for any suitable application. The step of analyzing the prognostic parameter may comprise the analysis of multiple prognostic parameters, which may be quantitative, semi-quantitative, qualitative, and/or extended.

Figure 22A:
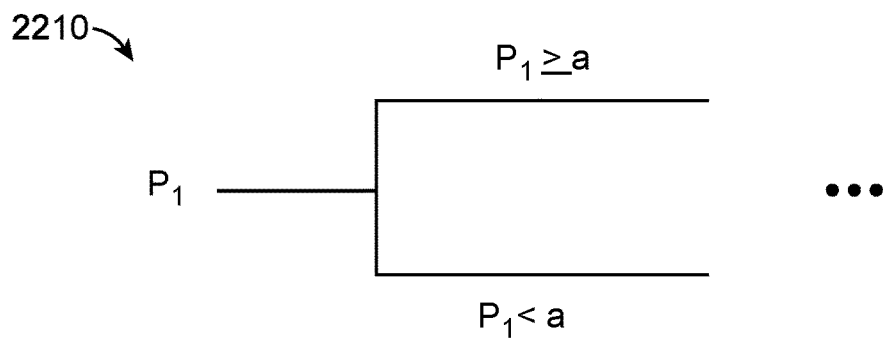
FIG. 22A illustrates an example classifier model comprising a threshold value of a single prognostic parameter, in accordance with some embodiments.

FIG. 22A shows an example classifier model 2210 comprising a threshold value of a single prognostic parameter, in accordance with embodiments. In some embodiments, prognostic parameter $P_1$ may be an extended prognostic parameter comprising a user-selected classification of a margin boundary of a region of interest according to an integer scale. In some embodiments, classifier model 2210 may be based entirely upon qualitative or quantitative prognostic parameters associated with sound propagation in the volume of tissue. In other embodiments, classifier model 2210 may be used in conjunction with another classifier model such as 2220 or 2230, such that the output of one classifier model may be used as a prognostic parameter in the input of another.

In some embodiments, the user-selected classification may be performed by a skilled operator, such as a medical professional, and in other embodiments, the user-selected classification may be aided by a computer implemented method or algorithm. In some embodiments, the classification may be performed in conjunction with observation of a waveform sound speed rendering; however, the classification may be performed using an image or rendering of any acoustic data type, such as the acoustic sound speed, acoustic attenuation, acoustic reflection, and an enhanced image generated from the sound speed, the acoustic attenuation, and the acoustic reflection.

In some embodiments, the user-selected classification may be assessed from an existing classification method such as the BI-RADS criteria, which may be predominantly devoted to assessment of tumor shape, margins and interaction with adjacent tissue. Such criteria as "shadowing" or "enhanced through transmission" in the BI-RADS may not be applicable ultrasound tomographic methods described herein; however, other criteria may be more sensitively detecting using ultrasound tomography, such as specular reflections of benign mass capsules, or the spiculations and/or architectural distortions of many cancers. In other embodiments, an adapted user-selected classification system may be implemented, which has been optimized for ultrasound tomographic imaging. Such a method may be based on a 5-point scale (the margin boundary score) that combines US-BI-RADS criteria for tumor margins as well as peritumoral tissue interaction.

An example use of classifier model 2210 includes a threshold for the operator assessed score at a value a, such that if $P_1 \geq a$ the mass may be diagnosed as cancerous. For example, Example 1 includes clinical data including diagnostic outcomes using the margin boundary score assessed from a waveform sound speed image for prognostic parameter $P_1$ and a threshold value of 3.

Another example use of classifier model 2210 includes a threshold for the operator assessed score at a value a, such that if $P_1 > a$ the mass may be diagnosed as cancerous. Another example use of classifier model 2210 includes a threshold for the operator assessed score at a value a, such that if $P_1 \leq a$ the mass may be diagnosed as cancerous. Another example use of classifier model 2210 includes a threshold for the operator assessed score at a value a, such that if $P_1 < a$ the mass may be diagnosed as cancerous. Another example use of classifier model 2210 includes evaluating a function of the value a and diagnosing the mass as cancerous based on the evaluated function of the value a.

Figure 22B:
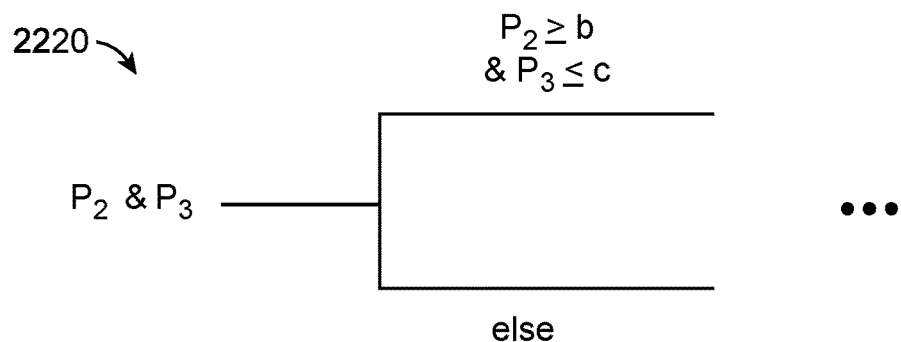
FIG. 22B illustrates an example classifier model comprising a threshold value of an interior prognostic parameter and an exterior prognostic parameter, in accordance with some embodiments.

FIG. 22B shows an example classifier model 2220 comprising a threshold value of an interior prognostic parameter and an exterior prognostic parameter, in accordance with embodiments. In some embodiments, classifier model 2220 may be based entirely upon quantitative prognostic parameters associated with sound propagation in the volume of tissue. In other embodiments, classifier model 2220 may be based upon a combination of quantitative, semi-quantitative, and/or extended prognostic parameters (e.g., a margin boundary score). In other embodiments, classifier model 2220 may be used in conjunction with another classifier model such as 2210 or 930 such that the output of one classifier model may be used as a prognostic parameter in the input of another.

An example use of classifier model 2220 includes a threshold for an interior prognostic parameter $P_2$ at a value b and an exterior prognostic parameter $P_3$ at a value c, such that if $P_2 \geq b$ and $P_3 \leq c$ the mass may be diagnosed as cancerous. For example, Example 1 includes clinical data including diagnostic outcomes using the volume-standard-deviation for the acoustic attenuation for prognostic parameter $P_2$ with a threshold value of 0.0347 and using the volume-average for the sound speed exterior to the region of interest (e.g., in the peritumoral region) for prognostic parameter $P_3$ with a threshold value of 1.51.

Another example use of classifier model 2220 includes a threshold for an interior prognostic parameter $P_2$ at a value b and an exterior prognostic parameter $P_3$ at a value c, such that if $P_2 > b$ and $P_3 > c$ the mass may be diagnosed as cancerous. Another example use of classifier model 2220 includes a threshold for an interior prognostic parameter $P_2$ at a value b and an exterior prognostic parameter $P_3$ at a value c, such that if $P_2 \leq b$ and $P_3 \leq c$ the mass may be diagnosed as cancerous. Another example use of classifier model 2220 includes a threshold for an interior prognostic parameter $P_2$ at a value b and an exterior prognostic parameter $P_3$ at a value c, such that if $P_2 < b$ and $P_3 < c$ the mass may be diagnosed as cancerous. Another example use of classifier model 2220 includes evaluating a function or piece-wise function of two or more variables (b, c, . . . ) and diagnosing the mass as cancerous based on the evaluated function of the two or more variables. For example, example 1 includes clinical data for diagnosing based upon a function of two variables, the volume-standard-deviation of the attenuation and the volume-standard-deviation of the sound speed in the tumoral region.

Figure 22C:
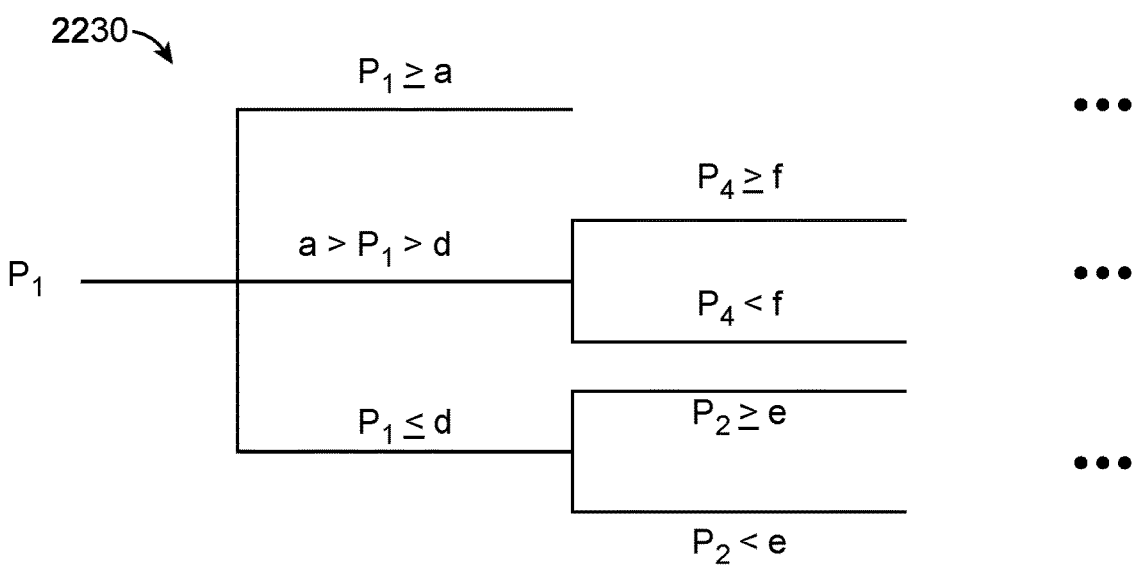
FIG. 22C illustrates an example classifier model comprising a mixed qualitative and quantitative metric for assessing a mass, in accordance with some embodiments.

FIG. 22C shows an example classifier model 2230 comprising a mixed qualitative and quantitative metric for assessing a mass, in accordance with embodiments. In some embodiments, classifier model 2230 may be based entirely upon quantitative prognostic parameters associated with sound propagation in the volume of tissue. In other embodiments, classifier model 2220 may be based upon a combination of quantitative, semi-quantitative, and/or extended prognostic parameters (e.g., a margin boundary score). In other embodiments, classifier model 2230 may be used in conjunction with another classifier model such as 2210 or 2220 such that the output of one classifier model may be used as a prognostic parameter in the input of another.

An example use of classifier model 2230 includes: an operator assessed score $P_1$ with two threshold values at a and d; an interior prognostic parameter $P_2$ at a value e; and a relative prognostic parameter $P_4$ calculated from a difference of an interior and an exterior prognostic parameter at a value f. If the operator assessed score $P_1$ is greater than or equal to a, the mass may be characterized as cancerous. If the operator assessed score of the region of interest is greater than d and less than a, the relative prognostic parameter $P_4$ may be further included in the assessment. If the value of $P_4$ is greater than f the lesion may be characterized as cancerous. If the operator assessed score $P_1$ is less than or equal to d, interior prognostic parameter $P_2$ may be further included in the model. If the value of $P_2$ is greater than or equal to the lesion may be classified as cancerous.

In the above use of classifier 2230, $P_1$ may be the margin boundary score with thresholds at 2 and 4. If the value of $P_1$ is 3, $P_4$ may be a prognostic parameter corresponding to the volume-averaged enhanced reflectance in the tumoral region less the volume-averaged enhanced reflectance in the distant peritumoral region. If the difference is ≥ to −34.6, the mass may be assessed as cancerous. If the $P_1$ is 1 or 2, $P_3$ may be the volume-standard-deviation of the corrected acoustic attenuation in the region of interest. If the standard deviation is >0.15 the cancer may be diagnosed as cancerous. Though classifier models 2210, 2220, and 2230 share prognostic parameters between models, the shared prognostic parameters shown are an example of one possible embodiment, and the example prognostic parameters in each classifier model could be of any acoustic data type, such as those disclosed herein.

Processors

In some embodiments, the platforms, systems, media, and methods described herein include a digital processing device, or equivalent, a processor. In further embodiments, the processor includes one or more hardware central processing units (CPUs) or general purpose graphics processing units (GPGPUs) that carry out the device's functions. In still further embodiments, the digital processing device further comprises an operating system configured to perform executable instructions. In some embodiments, the digital processing device is optionally connected to a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, set-top computers, media streaming devices, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

In some embodiments, the processor includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®. Those of skill in the art will also recognize that suitable media streaming device operating systems include, by way of non-limiting examples, Apple TV®, Roku®, Boxee®, Google TV®, Google Chromecast®, Amazon Fire®, and Samsung® HomeSync®. Those of skill in the art will also recognize that suitable video game console operating systems include, by way of non-limiting examples, Sony® PS3®, Sony® PS4®, Microsoft® Xbox 360®, Microsoft Xbox One, Nintendo® Wii®, Nintendo® Wii U®, and Ouya®.

In some embodiments, the processor includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the processor is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

In some embodiments, the processor includes a display to send visual information to a user. In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In yet other embodiments, the display is a head-mounted display in communication with the processor, such as a VR headset. In further embodiments, suitable VR headsets include, by way of non-limiting examples, HTC Vive, Oculus Rift, Samsung Gear VR, Microsoft HoloLens, Razer OSVR, FOVE VR, Zeiss VR One, Avegant Glyph, Freefly VR headset, and the like. In still further embodiments, the display is a combination of devices such as those disclosed herein.

In some embodiments, the processor includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera or other sensor to capture motion or visual input. In further embodiments, the input device is a Kinect, Leap Motion, or the like. In still further embodiments, the input device is a combination of devices such as those disclosed herein.

Figure 23:
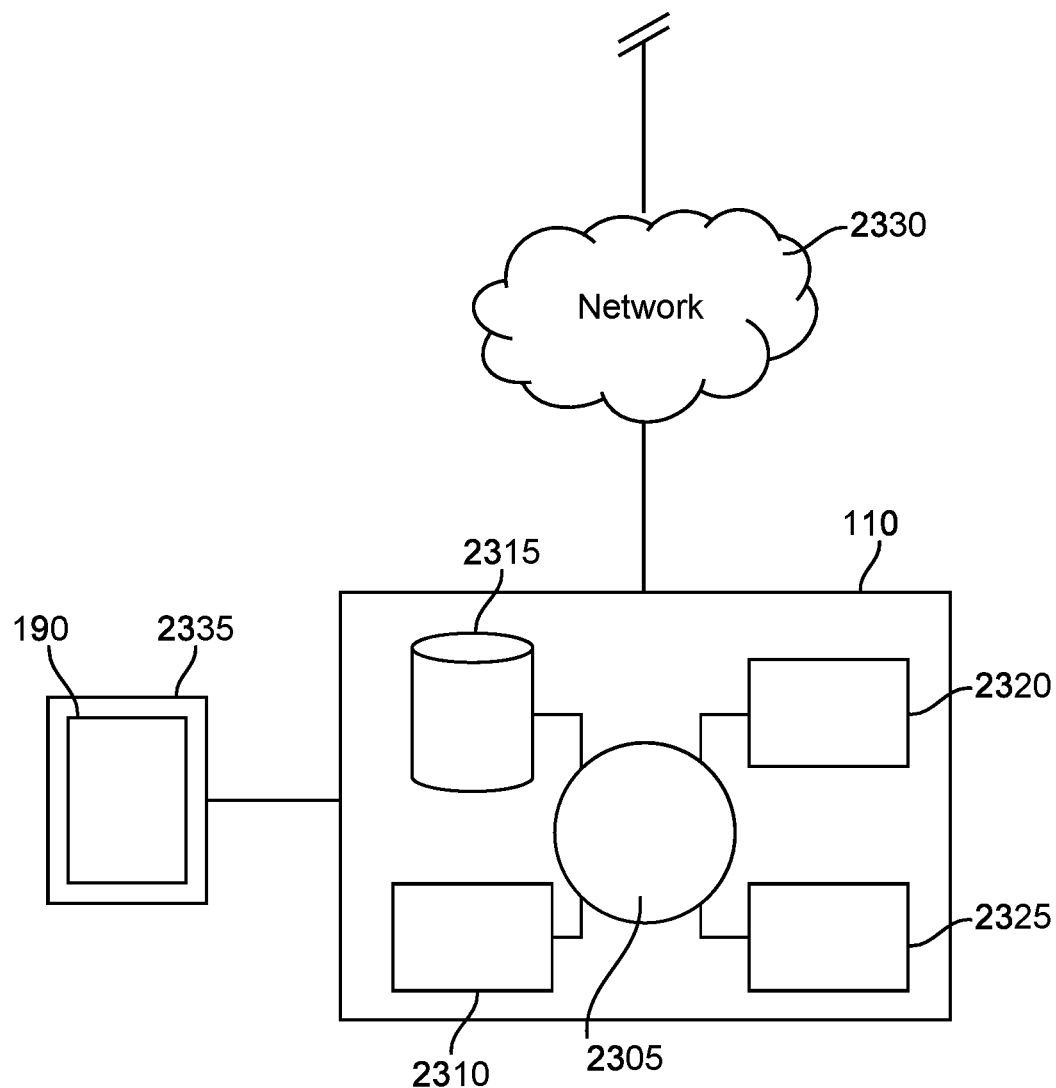
FIG. 23 illustrates an example processor which is programmed or otherwise configured to allow generation of regions of interest, feature extraction, feature selection, classifier model generation or fitting, evaluation of model accuracy, online use of model, etc, in accordance with some embodiments.

Referring to FIG. 23, in a particular embodiment, an example processor 110 is programmed or otherwise configured to allow generation of ROIs, feature extraction, feature selection, classifier model generation or fitting, evaluation of model accuracy, online use of model, etc. The processor 110 can regulate various aspects of the present disclosure, such as, for example, feature selection, ROI generation, feature extraction, etc. In this embodiment, the processor 110 includes a central processing unit (CPU, also "processor" and "computer processor" herein) 2305, which can be a single core or multi core processor, or a plurality of processors for parallel processing. The processor 110 also includes memory or memory location 2310 (e.g., random-access memory, read-only memory, flash memory), electronic storage unit 2315 (e.g., hard disk), communication interface 2320 (e.g., network adapter, network interface) for communicating with one or more other systems, and peripheral devices, such as cache, other memory, data storage and/or electronic display adapters. The peripheral devices can include storage device(s) or storage medium 1265 which communicate with the rest of the device via a storage interface 1270. The memory 2310, storage unit 2315, interface 2320 and peripheral devices are in communication with the CPU 2305 through a communication bus 2325, such as a motherboard. The storage unit 2315 can be a data storage unit (or data repository) for storing data. The processor 110 can be operatively coupled to a computer network ("network") 2330 with the aid of the communication interface 2320. The network 2330 can be the Internet, an internet and/or extranet, or an intranet and/or extranet that is in communication with the Internet. The network 2330 in some cases is a telecommunication and/or data network. The network 2330 can include one or more computer servers, which can enable distributed computing, such as cloud computing. The network 2330, in some cases with the aid of the device 110, can implement a peer-to-peer network, which may enable devices coupled to the device 110 to behave as a client or a server.

Continuing to refer to FIG. 23, the processor 110 includes input device(s) 145 to receive information from a user, the input device(s) in communication with other elements of the device via an input interface 1250. The processor 110 can include output device(s) 1255 that communicates to other elements of the device via an output interface 1260.

Continuing to refer to FIG. 23, the memory 2310 may include various components (e.g., machine readable media) including, but not limited to, a random access memory component (e.g., RAM) (e.g., a static RAM "SRAM", a dynamic RAM "DRAM, etc.), or a read-only component (e.g., ROM). The memory 110 can also include a basic input/output system (BIOS), including basic routines that help to transfer information between elements within the processor, such as during device start-up, may be stored in the memory 2310.

Continuing to refer to FIG. 23, the CPU 2305 can execute a sequence of machine-readable instructions, which can be embodied in a program or software. The instructions may be stored in a memory location, such as the memory 2310. The instructions can be directed to the CPU 2305, which can subsequently program or otherwise configure the CPU 2305 to implement methods of the present disclosure. Examples of operations performed by the CPU 2305 can include fetch, decode, execute, and write back. The CPU 2305 can be part of a circuit, such as an integrated circuit. One or more other components of the device 110 can be included in the circuit. In some cases, the circuit is an application specific integrated circuit (ASIC) or a field programmable gate array (FPGA).

Continuing to refer to FIG. 23, the storage unit 2315 can store files, such as drivers, libraries and saved programs. The storage unit 2315 can store user data, e.g., user preferences and user programs. The processor 110 in some cases can include one or more additional data storage units that are external, such as located on a remote server that is in communication through an intranet or the Internet. The storage unit 2315 can also be used to store operating system, application programs, and the like. Optionally, storage unit 2315 may be removably interfaced with the processor (e.g., via an external port connector (not shown)) and/or via a storage unit interface. Software may reside, completely or partially, within a computer-readable storage medium within or outside of the storage unit 2315. In another example, software may reside, completely or partially, within processor(s) 2305.

Continuing to refer to FIG. 23, the processor 110 can communicate with one or more remote computer systems 1202 through the network 2330. For instance, the device 110 can communicate with a remote computer system of a user. Examples of remote computer systems include personal computers (e.g., portable PC), slate or tablet PCs (e.g., Apple® iPad, Samsung® Galaxy Tab), telephones, Smart phones (e.g., Apple® iPhone, Android-enabled device, Blackberry®), or personal digital assistants.

Continuing to refer to FIG. 23, information and data can be displayed to a user through a display 2335. The display is connected to the bus 2325 via an interface 190, and transport of data between the display other elements of the device 110 can be controlled via the interface 190.

Methods as described herein can be implemented by way of machine (e.g., computer processor) executable code stored on an electronic storage location of the processor 110, such as, for example, on the memory 2310 or electronic storage unit 2315. The machine executable or machine readable code can be provided in the form of software. During use, the code can be executed by the processor 2305. In some cases, the code can be retrieved from the storage unit 2315 and stored on the memory 2310 for ready access by the processor 2305. In some situations, the electronic storage unit 2315 can be precluded, and machine-executable instructions are stored on memory 2310.

Non-Transitory Computer Readable Storage Medium

In some embodiments, the platforms, systems, media, and methods disclosed herein include one or more non-transitory computer readable storage media encoded with a program including instructions executable by the operating system of an optionally networked processor. In further embodiments, a computer readable storage medium is a tangible component of a processor. In still further embodiments, a computer readable storage medium is optionally removable from a processor. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

Computer Program

In some embodiments, the platforms, systems, media, and methods disclosed herein include at least one computer program, or use of the same. A computer program includes a sequence of instructions, executable in the processor's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

Web Application

In some embodiments, a computer program includes a web application. In light of the disclosure provided herein, those of skill in the art will recognize that a web application, in various embodiments, utilizes one or more software frameworks and one or more database systems. In some embodiments, a web application is created upon a software framework such as Microsoft® .NET or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash® Actionscript, Javascript, or Silverlight. In some embodiments, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. In some embodiments, a web application includes a media player element. In various further embodiments, a media player element utilizes one or more of many suitable multimedia technologies including, by way of non-limiting examples, Adobe® Flash®, HTML 5, Apple® QuickTime®, Microsoft® Silverlight®, Java™, and Unity®.

Figure 24:
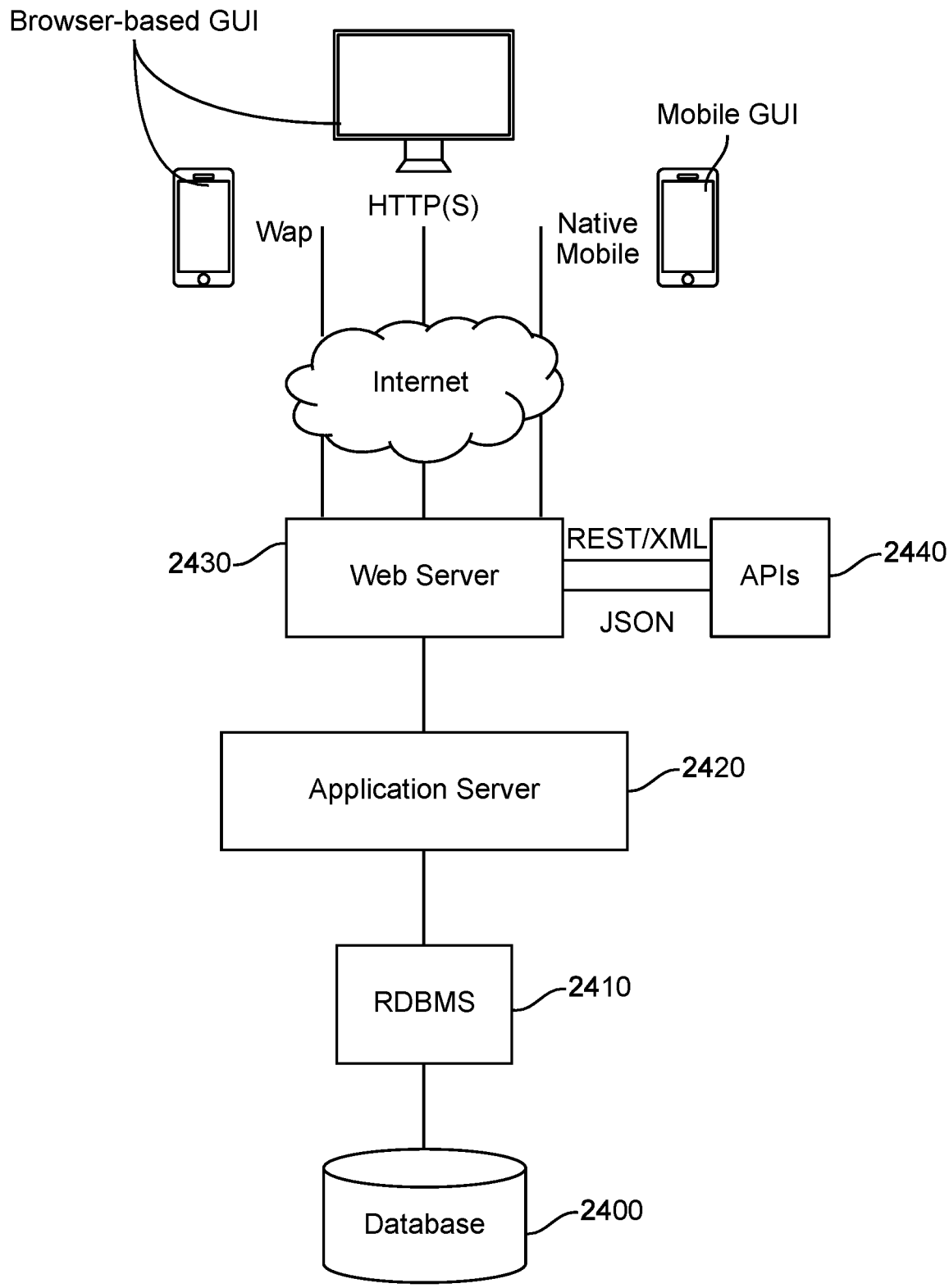
FIG. 24 illustrates an application provision system comprising one or more databases accessed by a relational database management system, in accordance with some embodiments.

Referring to FIG. 24, in a particular embodiment, an application provision system comprises one or more databases 2400 accessed by a relational database management system (RDBMS) 2410. Suitable RDBMSs include Firebird, MySQL, PostgreSQL, SQLite, Oracle Database, Microsoft SQL Server, IBM DB2, IBM Informix, SAP Sybase, SAP Sybase, Teradata, and the like. In this embodiment, the application provision system further comprises one or more application severs 2420 (such as Java servers, .NET servers, PHP servers, and the like) and one or more web servers 2430 (such as Apache, IIS, GWS and the like). The web server(s) optionally expose one or more web services via app application programming interfaces (APIs) 2440. Via a network, such as the Internet, the system provides browser-based and/or mobile native user interfaces.

Figure 25:
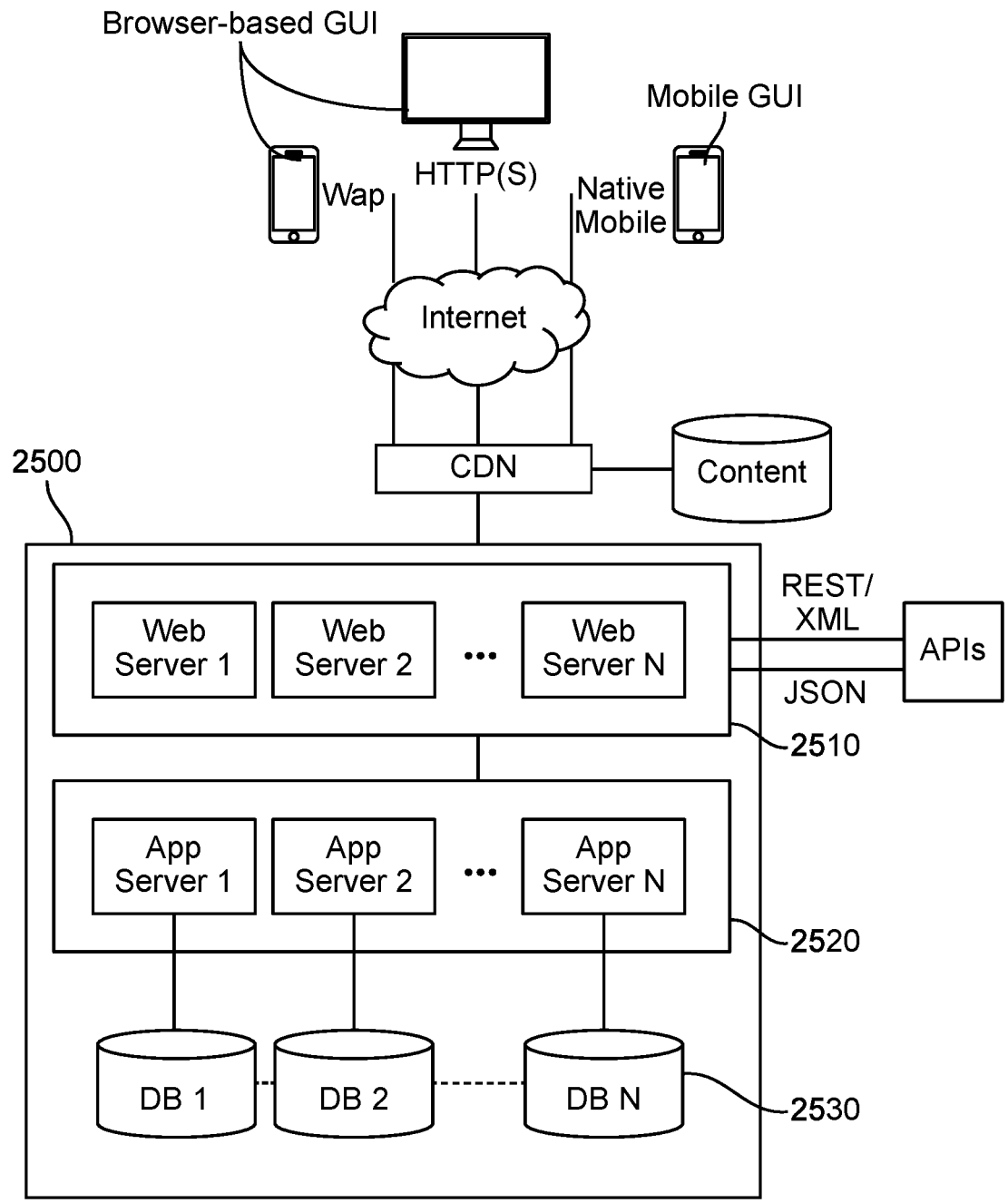
FIG. 25 illustrates an application provision system having a distributed, cloud-based architecture, in accordance with some embodiments.

Referring to FIG. 25, in a particular embodiment, an application provision system alternatively has a distributed, cloud-based architecture 2500 and comprises elastically load balanced, auto-scaling web server resources 2510 and application server resources 2520 as well synchronously replicated databases 2530.

Mobile Application

In some embodiments, a computer program includes a mobile application provided to a mobile processor. In some embodiments, the mobile application is provided to a mobile processor at the time it is manufactured. In other embodiments, the mobile application is provided to a mobile processor via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C#, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Google® Play, Chrome Web Store, BlackBerry® App World, App Store for Palm devices, App Catalog for webOS, Windows® Marketplace for Mobile, Ovi Store for Nokia® devices, Samsung® Apps, and Nintendo® DSi Shop.

Software Modules

In some embodiments, the platforms, systems, media, and methods disclosed herein include software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

Databases

In some embodiments, the platforms, systems, media, and methods disclosed herein include one or more databases, or use of the same. In view of the disclosure provided herein, those of skill in the art will recognize that many databases are suitable for storage and retrieval of raw image data, reconstructed image data, ROIs, training data, label or classification, features, subcategory of features, machine learning algorithms, etc. In various embodiments, suitable databases include, by way of non-limiting examples, relational databases, non-relational databases, object oriented databases, object databases, entity-relationship model databases, associative databases, and XML databases. Further non-limiting examples include SQL, PostgreSQL, MySQL, Oracle, DB2, and Sybase. In some embodiments, a database is internet-based. In further embodiments, a database is web-based. In still further embodiments, a database is cloud computing-based. In other embodiments, a database is based on one or more local computer storage devices.

EXAMPLES

The following illustrative examples are representative of embodiments of the software applications, systems, and methods described herein and are not meant to be limiting in any way.

Example 1

Clinical studies were conducted to develop a method of generating an enhanced image of a volume of tissue and a method for characterizing a volume of breast tissue of a patient. Results are presented from clinical studies that utilize breast imaging that is based on ultrasound tomography, which quantifies tissue characteristics while also producing 3D images of breast anatomy, which methods described herein may include.

Informed consent was obtained from all patients, prospectively recruited in an IRB-approved protocol following HIPAA guidelines. Coronal images were produced by tomographic algorithms for reflection, sound speed and attenuation. All images were reviewed by a board-certified radiologist with more than 20 years of experience in breast imaging and US-technology development. In the first phase of the study, UST images were compared to multi-modal imaging to determine the appearance of lesions and breast parenchyma. In the second phase of the study, correlative comparisons with magnetic resonance (MR) breast imaging were used to establish basic operational capabilities of the ultrasound tomography (UST) system including the identification and characterization of parenchymal patterns, determination of the spatial resolution of UST and an estimate the breast volume that can imaged with UST. The third phase of the study focused on lesion characterization. Region of interest (ROI) analysis was performed on all identified lesions using all three UST image types. Combinations of the ROI generated values were used to characterize all masses in the study.

The studies demonstrated a high degree of correlation of breast tissue structures relative to fat subtracted contrast enhanced MRI and the ability to scan ~90% of the volume of the breast at a resolution of 0.7 mm in the coronal plane. With a scan duration of ~1-3 minutes, no significant motion artifacts were observed. Initial clinical results suggest an ability to characterize lesions using margin boundary scores in combination with sound speed and attenuation parameters.

Figure 26A:
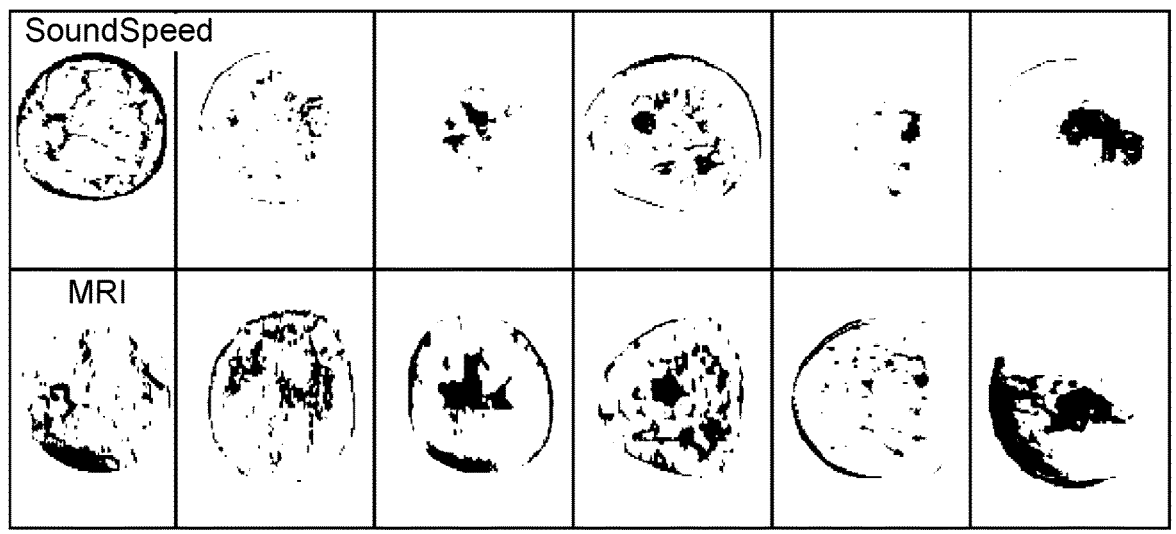
FIG. 26A illustrates a comparison between UST speed of sound and MR contrast enhanced fat subtracted images of representative breast parenchyma, in accordance with some embodiments.

UST and MR imaging was performed within weeks of each other. UST imaging was carried out with the SoftVue system (Delphinus Medical Technologies) and the MR exams with a Philips Achieva 3T system. The resulting image sequences were qualitatively and quantitatively to assess imaging performance of UST. As discussed above, UST images correlate best with MR images. Further inspection shows that of the three UST image types, the sound speed image correlates best with MR. FIG. 26A shows a coronal view comparison between UST speed of sound and MR contrast enhanced fat subtracted images of representative breast parenchyma.

The parenchymal patterns are very similar with the only major difference relating to the shape of the breast. This difference can be explained by the fact that the SoftVue system utilizes water so that buoyancy foreshortens the breast while with MR, gravity lengthens the breast in the AP dimension (e.g., prone). As discussed above, UST images correlate best with MR images. Further inspection shows that of the three UST image types, the sound speed image correlates best with MR, as illustrated in FIG. 26A.

MRI and UST breast volumes were compared using a paired t-test. In the first step, a k-means segmentation algorithm was applied to Ti breast MR images to automatically separate out the non-tissue background. In the second step, the boundary between the breast tissue and the chest wall was drawn manually and the chest wall removed, leaving behind only breast tissue.

In the UST images a semi-automated tool was used to draw a boundary around the breast tissue in each coronal slice and everything outside the boundary removed (water signal). Any slices containing chest wall signal were also removed.

Figure 26B:
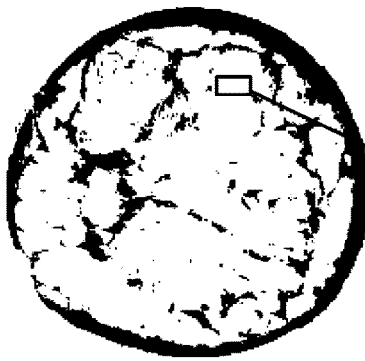
FIG. 26B illustrates estimation of the spatial resolution of UST and MR, in accordance with some embodiments.
Figure 26B:
Figure 26B:
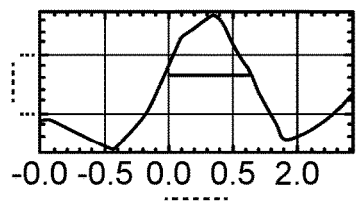

The spatial resolution of each modality was estimated using profile cuts of thin features, using the full-width, half-maximum criterion as shown in FIG. 26B. The results of the spatial resolution analysis are shown in the table below. The spatial resolution was found to be dependent on the reprojection type for both MRI and with UST outperforming MRI in the coronal plane and MRI outperforming UST in the other projections. (However, MR acquisitions with isotropic voxels would show comparable resolution to UST in the coronal plane). The UST image voxels are not isotropic and data acquisition cannot be readily adjusted like MR, such that UST reconstructed in axial and sagittal planes have resolution that approach the 2.5-mm slice thickness at this time.

| Resolution | UST | MRI |
| --- | --- | --- |
| Coronal | 0.7 +/− 0.1 mm | 1.6 +/− 0.3 mm |
| Axial/Sagittal | 2.5 +/− 0.5 mm | 0.8 +/− 0.1 mm |

US-BI-RADS criteria are predominantly devoted to assessment of tumor shape, margins, and interaction with adjacent tissue. However, criteria such as shadowing or enhanced through transmission are not applicable to UST's circular geometry. In addition, UST, operating at 3 MHz, appears more sensitive to the specular reflectors of benign mass capsules, or the spiculations and/or architectural distortions of many cancers. Therefore, we developed a 5-point scale (the margin boundary score) that combined US-BI-RADS criteria for tumor margins, as well as possibilities for peritumoral tissue interaction.

Figure 27:
FIG. 27 illustrates differences in sound speed texture and morphology noted for cysts, fibroadenomas, and cancer, in accordance with some embodiments.

A goal may be to generate textural analyses that may be less operator dependent and serve as appropriate diagnostic aids for a detected mass by simply requiring the radiologist to draw an ellipsoidal ROI. FIG. 27 shows the basic differences in sound speed texture and morphology noted for many cysts, fibroadenomas, and cancer. Based on the margin boundary score's five point scale, a classifier model can be implemented using classifier model 910, wherein a margin boundary score equal to or above a threshold value of three may be diagnosed as cancer. A first table showing the type of lesion, the assessed margin boundary score of the region for the patients surveyed (containing 107 benign lesions and 31 cancers) is shown below:

| SS Margin Boundary | Cancer | Fibro | Cyst | Benign |
| --- | --- | --- | --- | --- |
| 1 | 2 | 32 | 26 | 2 |
| 2 | 1 | 16 | 11 | 8 |
| 3 | 6 | 5 | 3 | 3 |
| 4 | 19 | 0 | 0 | 1 |
| 5 | 3 | 0 | 0 | 0 |
| Total | 31 | 53 | 40 | 41 |

A second summary table showing the diagnostic results is shown below:

| | | | |
| --- | --- | --- | --- |
| Sensitivity | 90% | Total Positive | 28 |
| Specificity | 88.8% | False Positive | 12 |
| PPV | 70% | Total Negative | 95 |
| NPV | 96.9% | False Negative | 3 |
| Accuracy | 90.3% | Total | 138 |

Additionally, masses were characterized by a (i) Margin Boundary score, (ii) reflectivity, (iii) quantitative SS evaluation, and (iv) ATT evaluations. A semi-automatic Region-of-interest (ROI) tool was used to determine the quantitative properties of each mass. After identifying the mass of interest, a simple elliptical ROI may be drawn around the mass. The ROI algorithm then generates 20 radial ellipsoids—10 inside and 10 outside the mass. Quantitative information was then measured for each of the 20 annuli for subsequent analysis. The region of interest (ROI) analysis was performed on all identified lesions using all three UST image types. Combinations of the ROI generated values were used to characterize all masses in the study.

Figure 28A:
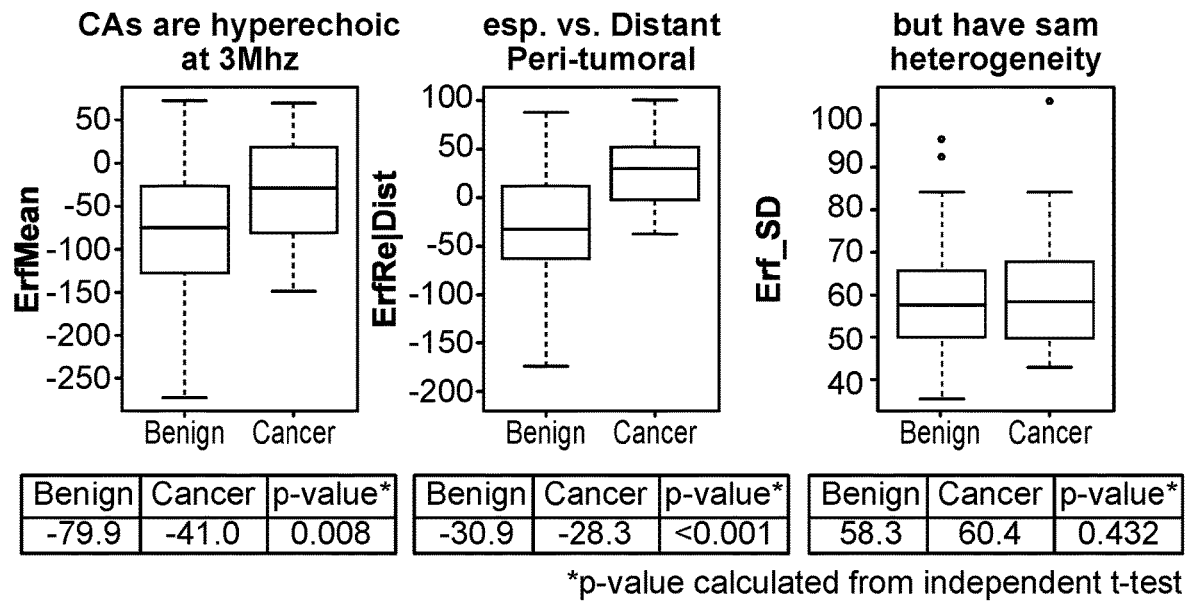
FIG. 28A and FIG. 28B illustrate box plots summarizing first order statistics within the tumoral ROI and comparisons with the surrounding peritumoral region, respectively, in accordance with some embodiments.
Figure 28B:
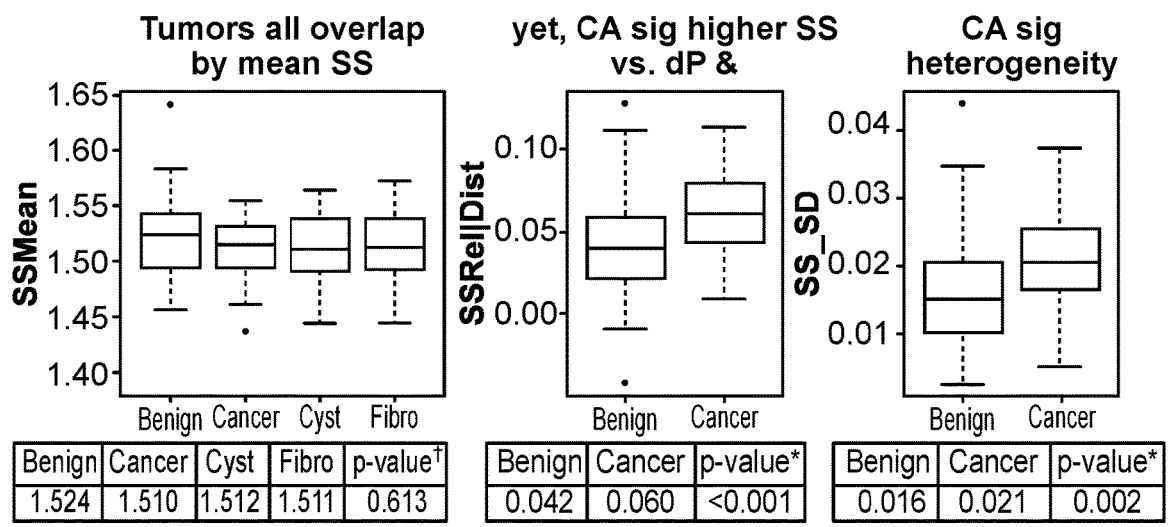

Our recent data highlights the significant impacts of first-order statistics, such as standard deviation, within the tumoral ROI and comparisons with the surrounding peritumoral region. FIGS. 28A-FIG. 28B show box plots summarizing said first order statistics including: the mean enhanced reflection (ErfMean), the relative mean enhanced reflection interior and exterior to the ROI (ErfRelDist), the standard deviation of the enhanced reflection (Erf_SD), the mean sound speed (SSMean), the relative mean sound speed interior and exterior to the ROI (SSRelDist), the standard deviation of the sound speed (SS_SD), the mean attenuation (AtMean), the standard deviation of the attenuation (At_SD), and the standard deviation of the attenuation corrected for the margin boundary score (Corr_At_SD). Each box plot also contains a summary table showing the associated value of the statistic for various types of lesions. The box plots were based on taking the average values for 107 benign lesions and 31 cancers.

Figure 28C:
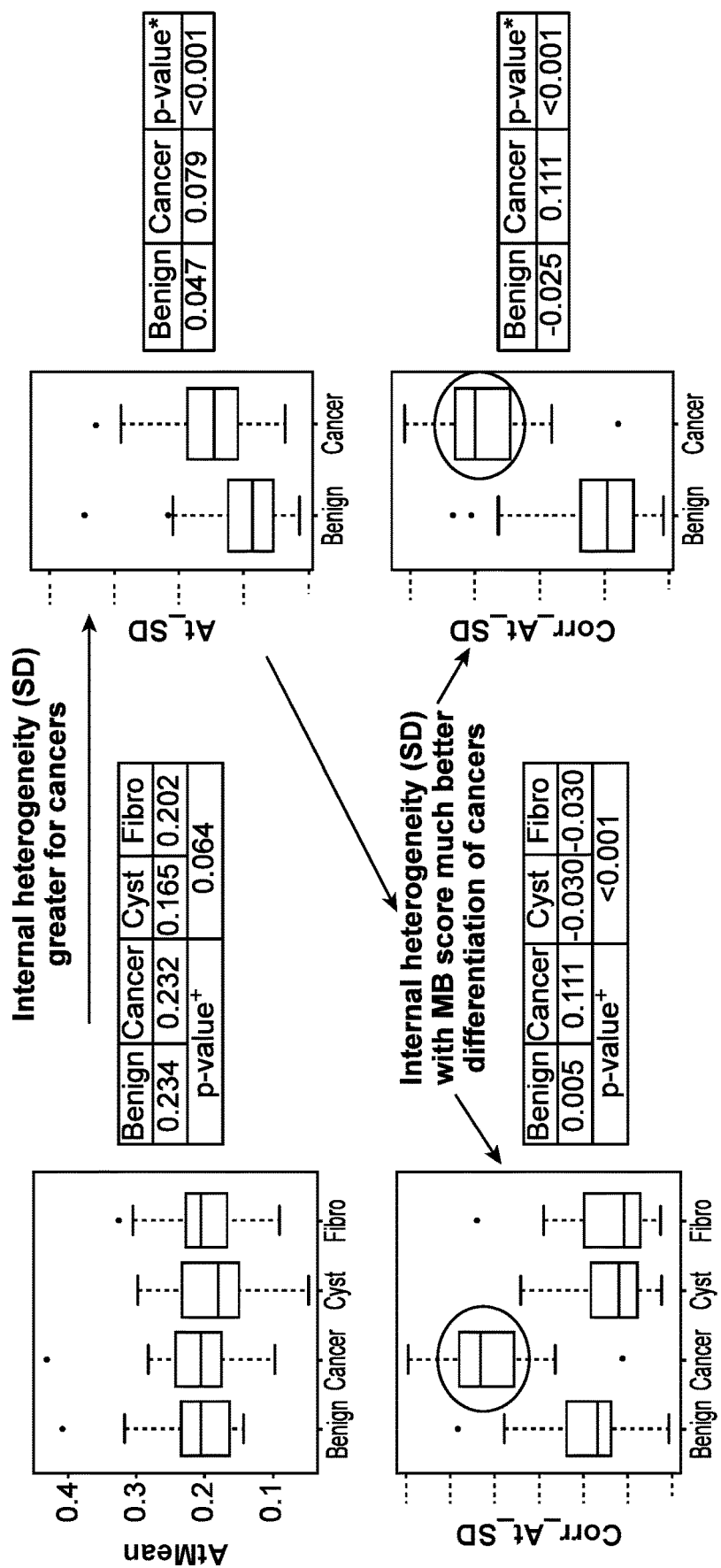
FIG. 28C illustrates differentiation achieved when using a boundary score combined with the first-order statistic of standard deviation, in accordance with some embodiments.

Scatterplots and box plots of the optimal methods were used to illustrate the characterization potential. The box plot in FIG. 28C shows the differentiation achieved when using the boundary score combined with the first-order statistic of standard deviation, a more crude measure of heterogeneity, based upon tumoral ROI extracted from ATT images, which had only slightly higher significance than SS. These ROIs were again obtained by simply drawing an elliptical ROI around the mass and determining the standard deviation within in the ROI.

Figure 29A:
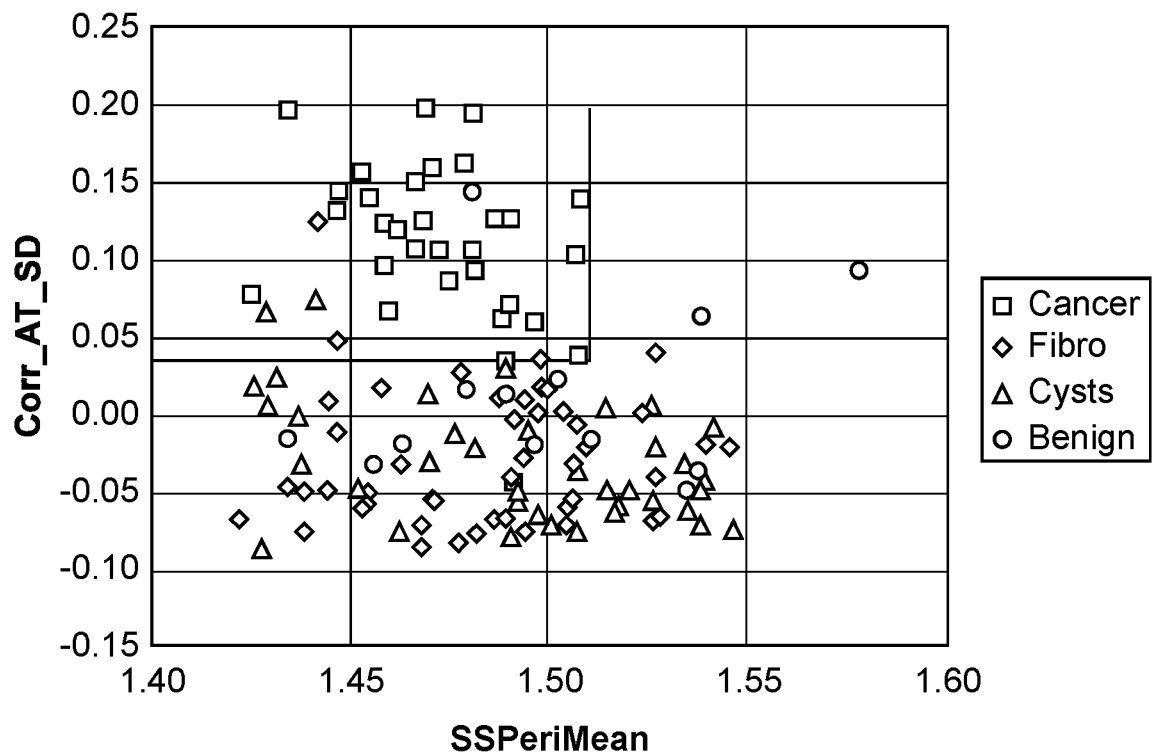
FIG. 29A illustrates a scatter plot of data generated using a classifier method, in accordance with some embodiments.

Upon further investigation, it was found that the SS of the peritumoral mass region (defined by an annular area just outside the mass boundary ROI) further separated the benign masses from cancer. The following data is generated using classifier method 920. A scatter plot based on all of these parameters is shown in FIG. 29A. The scatter plot shows separately the cancers, fibroadenomas and cancers. The cancers are tightly grouped in the top left corner of the plot indicating high boundary scores, high heterogeneity (standard deviation of sound attenuation≥0.0347) and lower peritumoral sound speed (mean sound speed in the peritumoral region≤1.51). By these measures, there was not much separation between cysts and fibroadenomas but significant separation between them and cancer. ROC analysis of the data represented in the scatter plot indicates a PPV of 91% when the sensitivity is 97%. A summary table showing the results is shown below:

| | | | |
| --- | --- | --- | --- |
| Sensitivity | 97% | Total Positive | 30 |
| Specificity | 94.4% | False Positive | 6 |
| PPV | 83% | Total Negative | 101 |
| NPV | 99.0% | False Negative | 1 |
| Accuracy | 96.8% | Total | 138 |

Figure 29B:
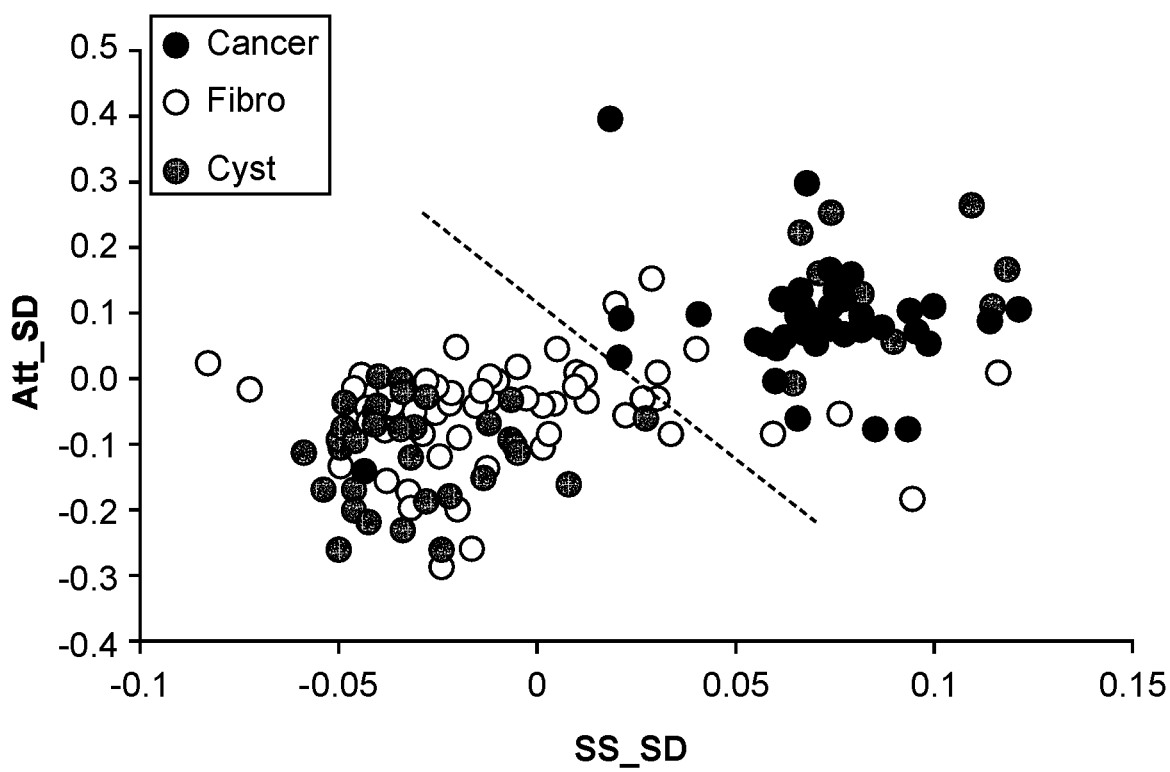
FIG. 29B illustrates patient values for each of two prognostic parameters, in accordance with some embodiments.

FIG. 29B shows a scatter plot based on the standard-deviation of the sound speed within the tumor and the standard-deviation of the attenuation within the tumor. An illustrative example of classifier model 920 using a linear function of the two prognostic parameters is shown by the line drawn through the scatter plot. If patient values for each of the two prognostic parameters plotted in FIG. 29B are above and right of the line, the lesion is diagnosed as cancerous.

This is a subset of data relative to an expanded ongoing study that includes more quantitative margin analyses. This method can also serve as a teaching tool for identifying grossly apparent textural differences within the tumor and surrounding peritumoral region.

Example 2—Combination of Feature Selection and Classifier Model Determines Accuracy of Classification A training data set contains 161 (93 benign and 68 malignant) samples of breast lesions is used to train various machine learning algorithms including J48 decision tree, neural network, AdaBoost (decision Stump), LibSVM algorithms. For J48 decision tree, a single class of features is used to train a tree. For other algorithms, combination of sound speed (SS) features and enhanced reflection (ERF) features are used. The training result for classification with J48 algorithm (with specified criteria, e.g., cross entropy for training) is as follows:

| B | M | ← classified as |
|---|---|---|
| 64 | 29 | B |
| 25 | 43 | M, | wherein B is benign tissue, M is malignant tissue. For neural network with selected parameter ($\alpha=0.2$, $\lambda=0.2$, seed=2), the optimal classification result with J48 algorithm is as follows:

| B | M | ← classified as |
|---|---|---|
| 72 | 21 | B |
| 21 | 47 | M, |

The decision stump algorithm generates a classification result as

| B | M | ← classified as |
|---|---|---|
| 72 | 21 | B |
| 22 | 46 | M, | while support vector machine (C-SVC, radial basis, $\gamma=0$, C=10) yields a classification result as:

| B | M | ← classified as |
|---|---|---|
| 82 | 11 | B |
| 23 | 45 | M. |

In this particular embodiment, combinations of SS and ERF attributes using different machine learning algorithms perform relatively the same or better than using J48 with any single feature class alone. Based on the accuracy, SS and ERF features may be selected with support vector machine to predict classification or label of unknown samples.

Example 3—Detection of Cancerous Lesions In Vivo 307 subjects having breast lesions were imaged as described herein. Of these 307 subjects, 227 subjects had benign lesions, and 80 subjects had cancerous lesions.

Of the subjects having benign lesions, 91 of the subjects had a benign lesion which was a cyst. 51 of the cyst lesions were in heterogenous dense breasts, and 40 of the cyst lesions were in extremely dense breasts. 111 of the subjects had a benign lesion which was a Fibroadenoma, wherein 82 were in heterogenous dense breasts, 28 were in extremely dense breasts, and 1 was in a scattered dense breast. 25 of the subjects had a benign lesion which was another type of lesion, of which 22 were in heterogenous dense breasts and 3 were in extremely dense breasts.

Of the subjects having cancerous lesions, 80 were in scattered dense breasts, 50 were in heterogenous dense breasts, and 11 were in extremely dense breasts.

OCT images were acquired using a breast shaper, and were all reconstructed using the same method.

Figure 30A:
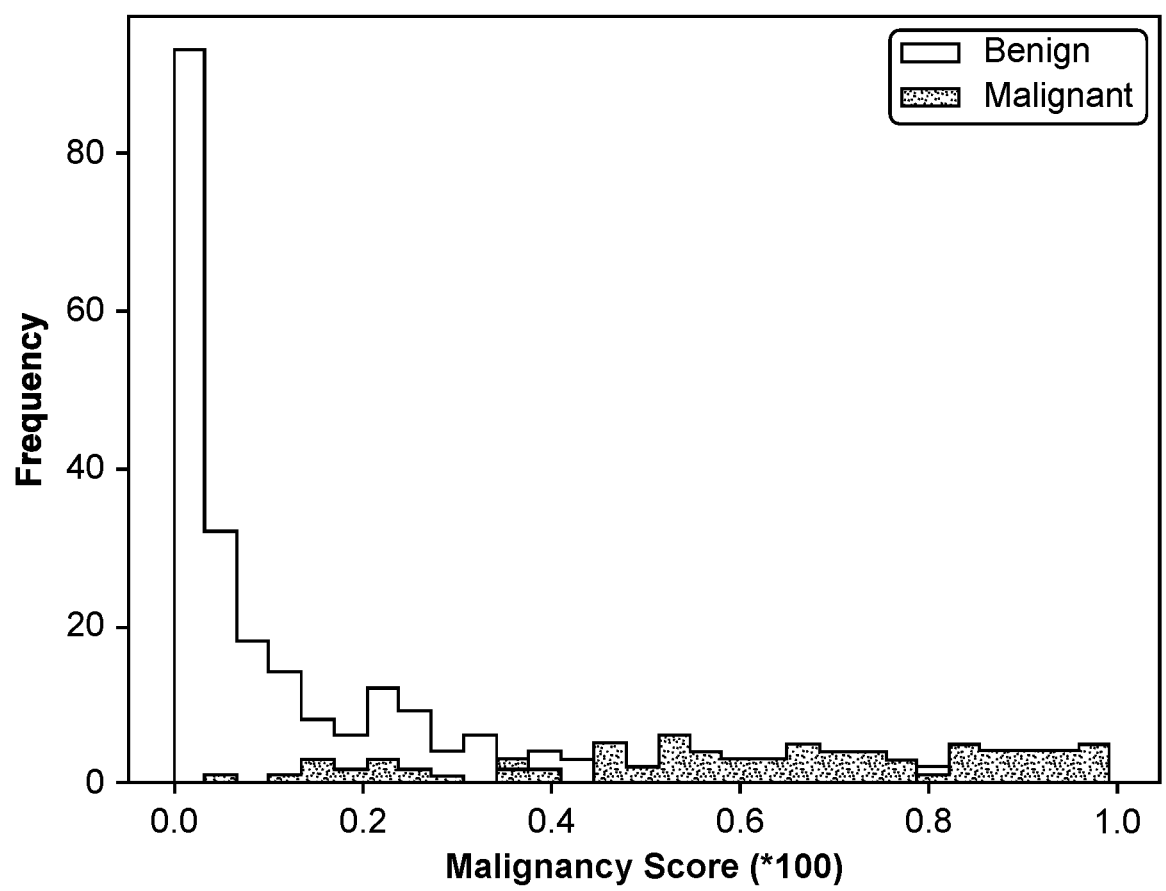
FIG. 30A illustrates a histogram of malignancy scores for lesions analyzed via an auto-segmentation algorithm described herein, in accordance with some embodiments.

Malignancy score was determined for each lesion using a lesion analysis tool algorithm as described herein. The malignancy scores for each lesion were recorded and are displayed in a histogram in FIG. 30A. Both benign malignant tumors are shown. Malignancy score ranged between 0% and 100%.

Figure 30B:
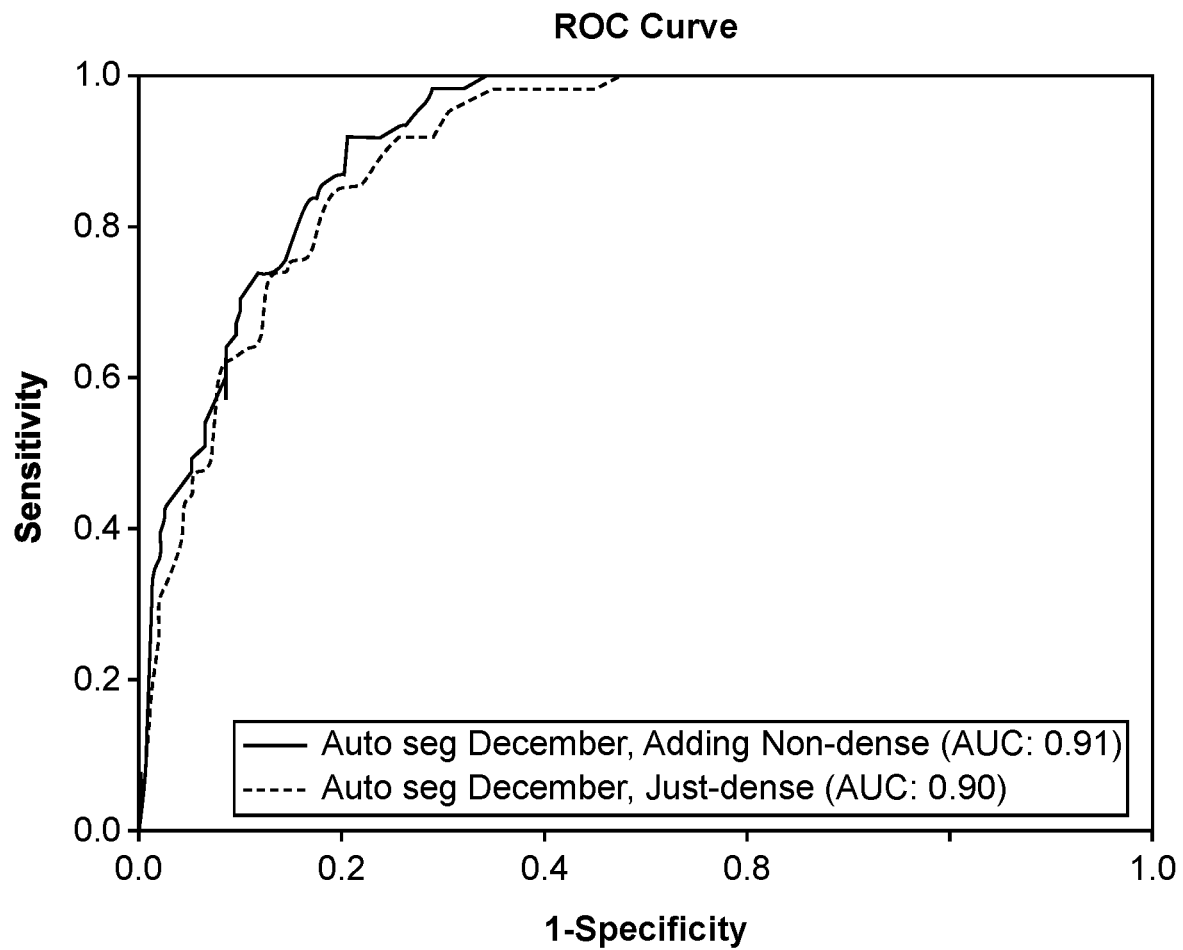
FIG. 30B illustrates receiver operating curves for an auto-segmentation algorithm, in accordance with some embodiments.

The algorithm has been trained with dense cancer or dense and non-dense cancer. The auto-segmentation algorithm was used to segment cancerous lesions, and segmentation was performed. Receiver operating characteristic curves were determined, and are displayed in FIG. 30B. When the algorithm was trained using only dense cancer cases, the area under the curve (AUC) was 0.90. When both dense and non-dense cancer cases were used to train the algorithm, the AUC was 0.91.

While preferred embodiments of the present subject matter have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the subject matter described herein may be employed in practicing the invention.

What is claimed is:

1. A computer implemented method for characterizing a lesion in a volume of tissue, the method comprising:
   receiving a plurality of acoustic renderings, the acoustic renderings comprising a representation of sound propagation through the volume of tissue, wherein the plurality of acoustic renderings comprises at least a transmission rendering and a reflection rendering;
   determining a set of prognostic parameters, wherein the set of prognostic parameters comprises one or a plurality of sound propagation metrics that are derived from the plurality of acoustic renderings; and
   applying a classifier model to classify the volume of tissue, wherein the classifier model is generated from:
     a first classifier configured to assign each prognostic parameter of a plurality of prognostic parameters a predictive value and
     generate the set of prognostic parameters from the plurality of prognostic parameters based on the predictive value of each prognostic parameter of the plurality of prognostic parameters, wherein the first classifier configured to trim the plurality of prognostic parameters based on the predictive value to generate the set of prognostic parameters; and
     a second classifier configured to calculate a score relating to a probability that the lesion is of a classification based on the set of prognostic parameters, wherein said second classifier is a trained classifier trained at least in part on the set of prognostic parameters and a plurality of classified acoustic renderings.

2. The method of claim 1, wherein the lesion comprises a cancer, a fibroadenoma, a cyst, a nonspecific benign mass, or an unidentifiable mass.

3. The method of claim 1, wherein the plurality of acoustic renderings comprises one or more of: (i) a plurality of reflection renderings, (ii) a plurality of transmission renderings, or (iii) at least one reflection rendering and at least one transmission rendering.

4. The method of claim 1, wherein the transmission rendering comprises a sound speed rendering or an attenuation rendering.

5. The method of claim 1, wherein the plurality of prognostic parameters comprises sound speed metrics relating to a region of interest and (i) is based on the region of interest or (ii) comprises a user-assigned classification of the region of interest.

6. The method of claim 5, wherein the region of interest (i) is a user selected region of interest, (ii) is partially selected using the set of prognostic parameters, (iii) comprises a portion of a lesion, or (iv) comprises a two-dimensional region of interest.

7. The method of claim 6, wherein the two-dimensional region of interest is used to generate a three-dimensional region of interest.

8. The method of claim 5, wherein the user-assigned classification is a mass boundary score.

9. The method of claim 1, wherein the set of prognostic parameters comprises at least one member selected from the group consisting of: a morphological metric of the lesion, crispiness, a texture metric of the region of interest, and fuzziness.

10. The method of claim 9, wherein the morphological metric comprises:
(i) at least one of a roundness, an irregularity of a shape, an irregularity of a margin, and a smoothness of a margin;
(ii) the fuzziness of a boundary of the lesion; or
(iii) the crispiness of a margin of the lesion.

11. The method of claim 1, wherein the one or a plurality of sound propagation metrics characterizes one or more of: (i) sound propagation interior to a region of interest or (ii) sound propagation exterior to a region of interest.

12. The method of claim 1, wherein the one or the plurality of sound propagation metrics comprises at least one of a mean, a standard deviation, a skewness, and a kurtosis.

13. The method of claim 1, wherein the one or the plurality of sound propagation metrics characterizes at least one of sound speed, sound attenuation, and sound reflection.

14. The method of claim 1, wherein the one or the plurality of sound propagation metrics comprises one or more members selected from the group consisting of a sound speed metric, a reflection metric, an attenuation metric, a morphological metric, and a user defined score.

15. The method of claim 1, wherein the set of prognostic parameters comprises one or more of: (i) one or a plurality of sound propagation metrics characterizing sound speed, (ii) one or a plurality of sound propagation metrics characterizing sound attenuation, or (iii) one or a plurality of sound propagation metrics characterizing sound reflection.

16. The method of claim 1, wherein the classifier model determines a type of tissue with a sensitivity at least 85% and a specificity of at least 84%.

17. The method of claim 1, wherein the classifier model determines: (i) a threshold value of one or more prognostic parameters sufficient to classify a tissue, (ii) a relative statistical accuracy of one or more prognostic parameters, (iii) a threshold value of the set of prognostic parameters sufficient to classify a tissue, or a combination thereof.

18. The method of claim 1, wherein the classifier determines a likelihood that the lesion is a malignant lesion.

19. The method of claim 1, wherein the trained classifier is generated using a machine learning technique.

* * * * *